United States Patent
Wittenberg et al.

(10) Patent No.: US 10,381,881 B2
(45) Date of Patent: Aug. 13, 2019

(54) ARCHITECTURE OF PORTABLE ELECTRONIC DEVICES WITH WIRELESS CHARGING RECEIVER SYSTEMS

(71) Applicant: Apple Inc., Cupertino, CA (US)

(72) Inventors: Michael B. Wittenberg, Sunnyvale, CA (US); Makiko K. Brzezinski, Santa Clara, CA (US); Stefan A. Kowalski, La Honda, CA (US); Christopher S. Graham, San Francisco, CA (US); Morgan T. McClure, San Francisco, CA (US); Erik G. de Jong, San Francisco, CA (US); Trevor J. Ness, Santa Cruz, CA (US); Peter J. Kardassakis, Mountain View, CA (US); Jayesh Nath, Milpitas, CA (US); Adam T. Clavelle, San Francisco, CA (US); Rex Tyler Ehman, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/122,766

(22) Filed: Sep. 5, 2018

(65) Prior Publication Data
US 2019/0074729 A1 Mar. 7, 2019

Related U.S. Application Data

(60) Provisional application No. 62/554,945, filed on Sep. 6, 2017.

(51) Int. Cl.
*H01F 27/42* (2006.01)
*H01F 37/00* (2006.01)
(Continued)

(52) U.S. Cl.
CPC .............. *H02J 50/40* (2016.02); *A61B 5/681* (2013.01); *H02J 7/025* (2013.01); *H02J 50/10* (2016.02); *H02J 50/80* (2016.02); *H02J 50/90* (2016.02)

(58) Field of Classification Search
None
See application file for complete search history.

(56) References Cited

U.S. PATENT DOCUMENTS

| 3,646,562 A | 2/1972 | Acker et al. |
| 5,814,900 A | 9/1998 | Esser et al. |
| (Continued) |

FOREIGN PATENT DOCUMENTS

| EP | 2950416 | 12/2015 |
| GB | 2431301 | 4/2007 |
| (Continued) |

OTHER PUBLICATIONS

U.S. Appl. No. 16/122,787, First Action Interview Pilot Program Pre-Interview Communication, dated Feb. 21, 2019, 4 pages.
(Continued)

*Primary Examiner* — Alfonso Perez Borroto
*Assistant Examiner* — Esayas G Yeshaw
(74) *Attorney, Agent, or Firm* — Kilpatrick Townsend & Stockton LLP

(57) ABSTRACT

Embodiments disclosed herein describe a wireless power receiving system for an electronic device includes: a first inductor coil configured to receive power primarily at a first frequency and from magnetic fields propagating in a first direction; and a second inductor coil configured to receive power primarily at a second frequency and from magnetic fields propagating in a second direction, wherein the first frequency is different than the second frequency.

20 Claims, 31 Drawing Sheets

(51) Int. Cl.
*H01F 38/00* (2006.01)
*H02J 50/40* (2016.01)
*H02J 50/10* (2016.01)
*H02J 7/02* (2016.01)
*H02J 50/90* (2016.01)
*H02J 50/80* (2016.01)
*A61B 5/00* (2006.01)

(56) References Cited

U.S. PATENT DOCUMENTS

| | | |
|---|---|---|
| 6,300,920 B1 | 10/2001 | Pertl et al. |
| 2002/0055763 A1 | 5/2002 | Zarinetchi et al. |
| 2003/0011527 A1 | 1/2003 | Kokorin et al. |
| 2004/0051617 A1 | 3/2004 | Buswell |
| 2007/0228833 A1* | 10/2007 | Stevens ............... H02J 5/005 307/45 |
| 2008/0074112 A1 | 3/2008 | Abe et al. |
| 2008/0079420 A1* | 4/2008 | Hrubes ............... G01D 5/202 324/207.16 |
| 2008/0303479 A1* | 12/2008 | Park ............... H02J 7/025 320/108 |
| 2010/0289341 A1 | 11/2010 | Ozaki et al. |
| 2011/0115735 A1* | 5/2011 | Lev ............... G06F 1/1616 345/173 |
| 2011/0127951 A1* | 6/2011 | Walley ............... H02J 7/025 320/108 |
| 2011/0164471 A1* | 7/2011 | Baarman ............... H02J 7/025 368/10 |
| 2012/0032632 A1* | 2/2012 | Soar ............... H01F 38/14 320/108 |
| 2012/0112552 A1 | 5/2012 | Baarman et al. |
| 2012/0200169 A1* | 8/2012 | Urano ............... H02J 5/005 307/104 |
| 2013/0049484 A1 | 2/2013 | Weissentern et al. |
| 2014/0143933 A1* | 5/2014 | Low ............... G04C 10/00 2/170 |
| 2014/0232330 A1 | 8/2014 | Robertson et al. |
| 2015/0015180 A1 | 1/2015 | Weinstein et al. |
| 2015/0123604 A1 | 5/2015 | Lee et al. |
| 2015/0195009 A1 | 7/2015 | Wang et al. |
| 2015/0326028 A1* | 11/2015 | Suzuki ............... H02J 7/025 307/104 |
| 2015/0371768 A1 | 12/2015 | Graham et al. |
| 2016/0064137 A1 | 3/2016 | Perez et al. |
| 2016/0111887 A1 | 4/2016 | Jeong |
| 2017/0047635 A1* | 2/2017 | Wolentarski ......... H04B 1/3838 |
| 2017/0133880 A1* | 5/2017 | Wakisaka ............... H02J 50/80 |
| 2018/0062430 A1* | 3/2018 | Matsumoto ............... H02J 7/00 |

FOREIGN PATENT DOCUMENTS

| | | |
|---|---|---|
| WO | 0059069 | 10/2000 |
| WO | 0180360 | 10/2001 |
| WO | 2009026253 | 2/2009 |
| WO | 2015191203 | 12/2015 |
| WO | 2015199044 | 12/2015 |

OTHER PUBLICATIONS

European Patent Application No. 18192974.6, Extended European Search Report, dated Jan. 16, 2019, 7 pages.

* cited by examiner

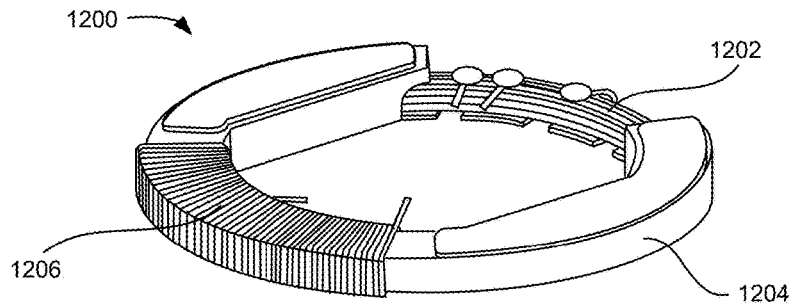
FIG. 12A
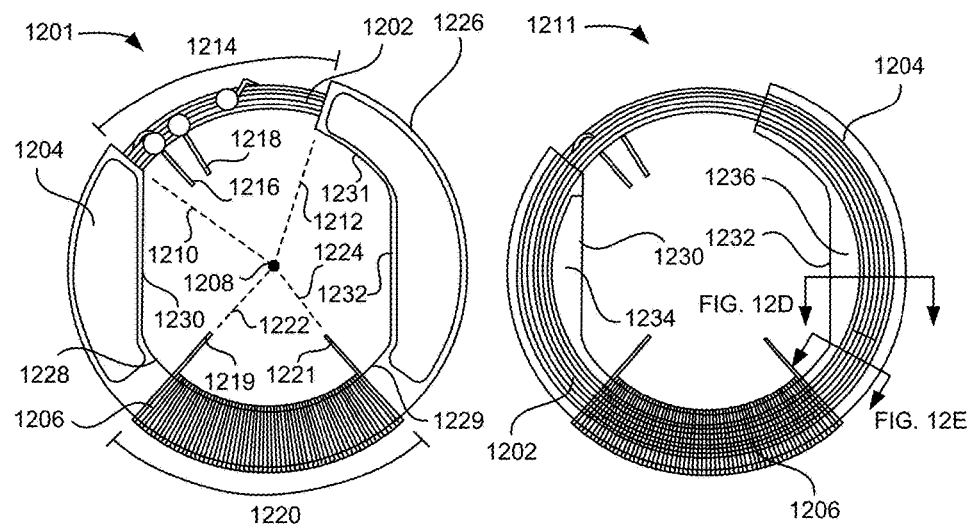
FIG. 12B  FIG. 12C
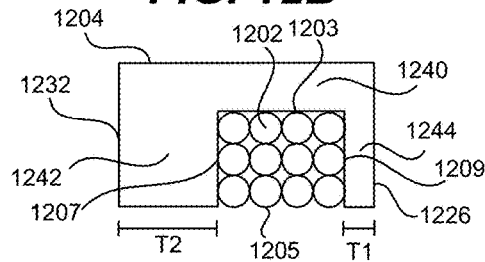  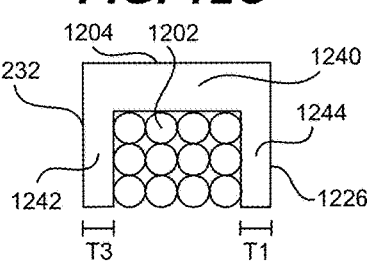
FIG. 12D  FIG. 12E

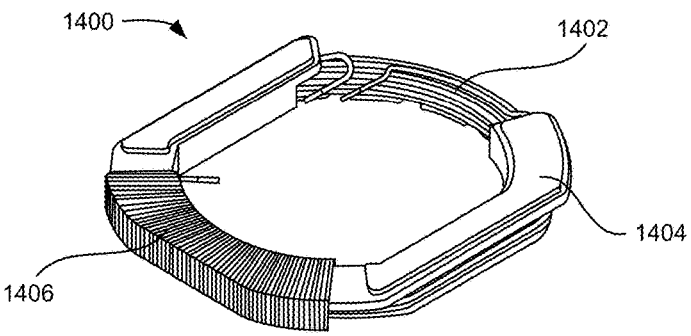
FIG. 14A
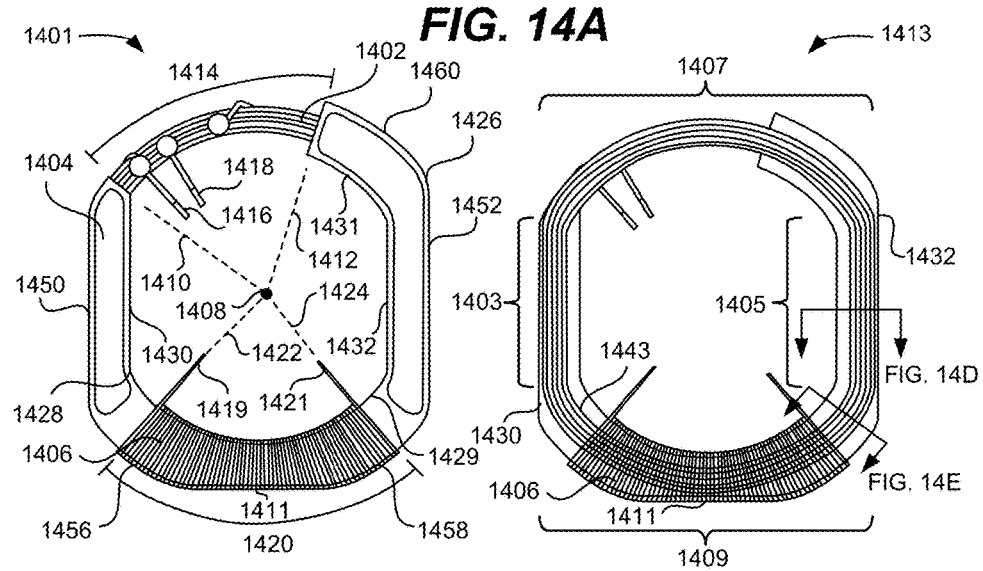
FIG. 14B    FIG. 14C
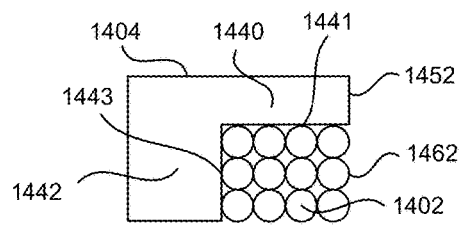    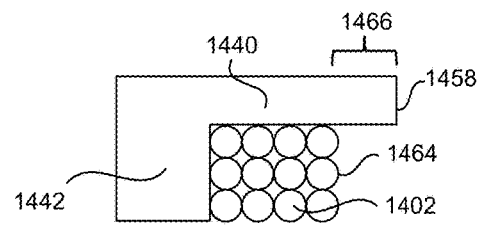
FIG. 14D    FIG. 14E

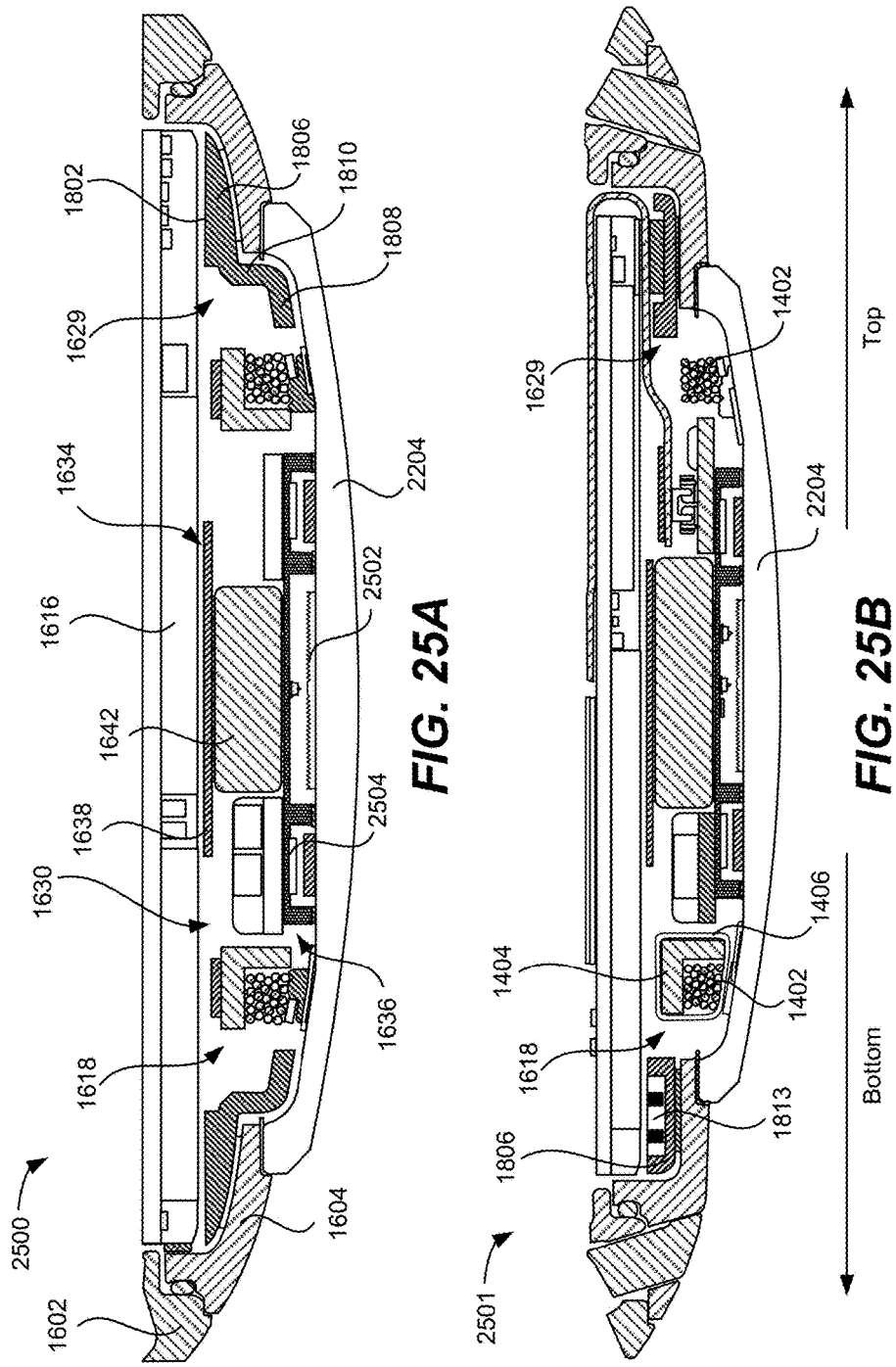

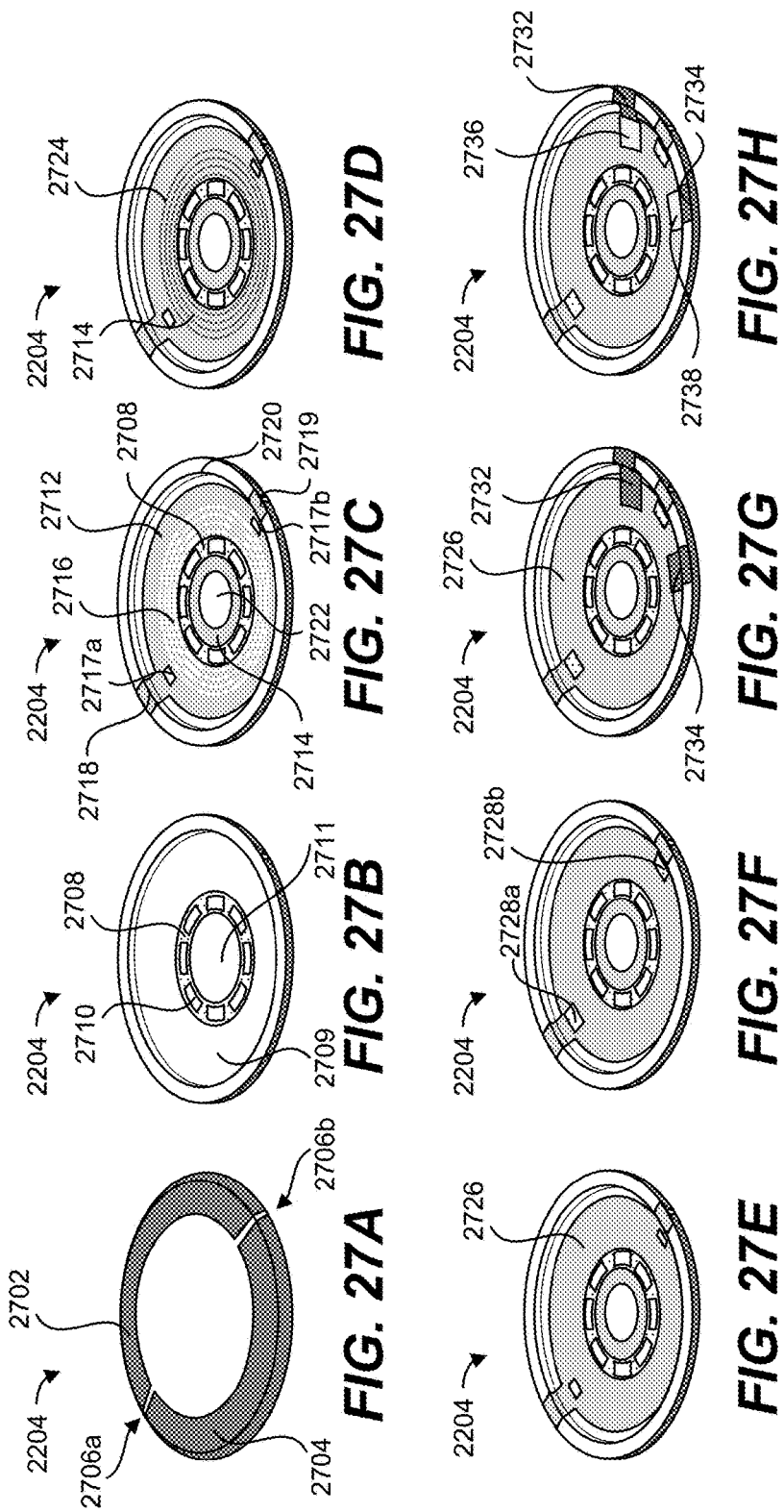

ARCHITECTURE OF PORTABLE ELECTRONIC DEVICES WITH WIRELESS CHARGING RECEIVER SYSTEMS

CROSS-REFERENCES TO RELATED APPLICATIONS

This application is a non-provisional patent application of and claims the benefit to U.S. Provisional Patent Application No. 62/554,945, filed Sep. 6, 2017 and titled "Wireless Charging Receiver Systems For Portable Electronic Devices,", and is related to the following concurrently filed and commonly assigned U.S. Non-Provisional patent applications: U.S. patent application Ser. No. 16/122,787, filed Sep. 5, 2018, entitled "Single-Structure Wireless Charging Receiver Systems having Multiple Receiver Coils"; U.S. patent application Ser. No. 16/122,799, filed Sep. 5, 2018, entitled "Antenna Integration for Portable Electronic Devices having Wireless Charging Receiver Systems"; and U.S. patent application Ser. No. 16/122,811, filed Sep. 5, 2018, entitled "Multiple-Structure Wireless Charging Receiver Systems having Multiple Receiver Coils", the disclosures of which are herein incorporated by reference in their entirety for all purposes.

BACKGROUND

Portable electronic devices (e.g., mobile phones, media players, smart watches, and the like) operate when there is charge stored in their batteries. Some portable electronic devices include a rechargeable battery that can be recharged by coupling the portable electronic device to a power source through a physical connection, such as through a charging cord. Using a charging cord to charge a battery in an electronic device, however, requires the portable electronic device to be physically tethered to a power outlet. Additionally, using a charging cord requires the portable electronic device to have a connector, typically a receptacle connector, configured to mate with a connector, typically a plug connector, of the charging cord. The receptacle connector typically includes a cavity in the portable electronic device that provides an avenue within which dust and moisture can intrude and damage the device. Furthermore, a user of the portable electronic device has to physically connect the charging cable to the receptacle connector in order to charge the battery.

To avoid such shortcomings, portable electronic devices have been configured with receiver coils that can receive power from a wireless charging device without the need for a charging cord. For example, some portable electronic devices can be recharged by merely resting the device on a charging surface of a wireless charging device. A transmitter coil disposed below the charging surface may produce a time-varying magnetic field that induces a current in a corresponding receiver coil in the portable electronic device. The induced current can be used by the portable electronic device to charge its internal battery.

Some existing portable electronic devices configured to receive wireless power have a number of disadvantages. For instance, some portable electronic devices require that it be placed in a very confined charging region on a charging surface of a wireless charging device in order to receive power. If the portable electronic device is placed outside of the charging region, the portable electronic device may not wirelessly charge or may charge inefficiently and waste power. Additionally, some portable electronic devices are configured to charge from only one type of wireless charging device. Thus, these portable electronic devices can only charge at one frequency and require the use of a specific type of wireless charging device. This limits the ease at which the portable electronic device can be wirelessly charged.

Furthermore, portable electronic devices, especially wearable portable electronic devices such as smart watches and the like, are designed to be compact so that they do not interfere with a user's mobility in his or her day-to-day activities. Having this compact design constrains the size limitations of internal components within the portable electronic device. As the functionality of the portable electronic devices increases, a larger number of electronic components will need to be housed within the portable electronic device, where some components will require larger amounts of space than other electronic components. Finding the right balance between size requirements of each internal component and its proper operation is difficult to achieve for such compact portable electronic devices.

SUMMARY

Some embodiments of the disclosure provide a wireless power receiver system for a portable electronic device. The wireless power receiving system can be configured to receive charge from various wireless charging devices and can fit within a compact enclosure of the portable electronic device along with an antenna configured for wireless (e.g., radio wave) communication. In some embodiments, the portable electronic device can be a smart watch that has a receiver system designed to include at least two different receiver coils for receiving wireless power from different wireless charging devices. The portable electronic device can have a compact footprint while having the ability to charge from multiple wireless charging devices, thereby easing the way in which the portable electronic device can receive power to charge its battery.

In some embodiments, a portable electronic device according to the disclosure includes a housing, an antenna, a wireless charging receiver system and a sensor module. The housing can include a top portion including a display and a bottom portion including a window where the bottom portion is configured to mate with the top portion to form an internal cavity. The antenna can be disposed within the internal cavity and include an antenna element and a conductive antenna body coupled to a bottom surface of the antenna element. The antenna can include an opening disposed at the center of the antenna and defined by an inner edge of the antenna. The wireless charging receiver system can be disposed within the internal cavity and the antenna opening and include a primary coil having an inner diameter and an outer diameter, a ferromagnetic shield covering a portion of at least two surfaces of the primary coil, and a secondary coil wound about overlapping portions of the primary coil and the ferromagnetic shield. The sensor module can be disposed within the internal cavity and the inner diameter of the primary coil and include at least one sensing device configured to measure a parameter of an environment external to the portable electronic device.

A portable electronic device according to some embodiments includes a housing, a spacer, a wireless charging receiver system, a sensor module, an alignment module and an electromagnetic shield layer. The housing can include a top portion including a display and a bottom portion including a window where the bottom portion is configured to mate with the top portion to form an internal cavity and the window includes a plurality of ink layers coated on portions of an inner surface and an outer surface of the window. The spacer can be disposed within the internal cavity and comprise a non-conductive material, the spacer can include an opening disposed at the center of the spacer and defined by an inner edge of the spacer. The wireless charging receiver system can be disposed within the internal cavity and the opening and include a primary coil having an inner diameter and an outer diameter, a ferromagnetic shield covering a portion of at least two surfaces of the primary coil, and a secondary coil wound about overlapping portions of the primary coil and the ferromagnetic shield. The sensor module can be disposed within the internal cavity and the inner diameter of the primary coil and include at least one sensing device configured to measure a parameter of an environment external to the portable electronic device. The alignment module can be coupled to the sensor module and include an alignment magnet and a DC shield attached to a top surface of the alignment magnet, and the electromagnetic shield layer can be positioned between the wireless charging receiver system and the window of the bottom portion of the housing.

In some embodiments a wireless charging system is provided. The system can include a first wireless charging transmitter and a wireless charging receiver. The wireless charging transmitter can include: a first housing having a first charging surface; and at least one first transmitter coil formed of a plurality of turns of stranded wire disposed within the first housing and below the charging surface, the at least one first transmitter coil configured to generate first time-varying magnetic fields through and above the first charging surface. The wireless charging receiver can include: a housing having a top portion including a display and a bottom portion including a window where the bottom portion is configured to mate with the top portion to form an internal cavity; an antenna disposed within the internal cavity and including an antenna element and a conductive antenna body coupled to a bottom surface of the antenna element where the antenna includes an opening disposed at the center of the antenna and defined by an inner edge of the antenna; a wireless charging receiver system disposed within the internal cavity and the antenna opening, the wireless charging receiver system including a primary receiver coil having an inner diameter and an outer diameter and configured to receive the first time-varying magnetic fields generated by the at least one first transmitter coil, a ferromagnetic shield covering a portion of at least two surfaces of the primary receiver coil, and a secondary receiver coil wound about overlapping portions of the primary receiver coil and the ferromagnetic shield; and a sensor module disposed within the internal cavity and the inner diameter of the primary receiver coil, the sensor module comprising at least one sensing device configured to measure a parameter of an environment external to the portable electronic device.

In some embodiments a wireless charging receiver system is provided that includes a primary coil, a ferromagnetic shield and a secondary coil. The primary can coil can be formed of a plurality of turns of stranded wire wound about a primary axis and configured to receive wireless power from time-varying magnetic fields generated at a first frequency and in a first direction. The ferromagnetic shield can be disposed over at least two adjacent surfaces of the primary coil and over a portion of the entire circumference of the at least two adjacent surfaces such that an annular segment of the primary coil is uncovered by the ferromagnetic shield, and the secondary coil can be formed of a plurality of turns of stranded wire wound about a secondary axis disposed along a circumference centered around the primary axis, the secondary coil covers overlapping portions of the ferromagnetic shield and the primary coil and is configured to receive wireless power from time-varying magnetic fields generated at a second frequency different from the first frequency and in a second direction different from the first direction.

Some additional embodiments pertain to an antenna for an electronic device. The antenna can include a non-conductive antenna element having a bottom surface, a conductive body attached to the bottom surface of the non-conductive antenna element and at least one capacitor. The non-conductive antenna element can include: a first planar top level comprising an outer edge; a first planar bottom level comprising an antenna opening and an inner edge; and a first step region disposed between the first top level and the first bottom level, the first step region coupling the first top level with the first bottom level and having a circular profile. The conductive body can attached conform to the non-conductive antenna element and include: a second planar top level below the first planar top level and a slit that divides a section of the conductive body into two parts; a second planar bottom level below the first planar top level; and a second step region disposed beside the first step region. The at least one capacitor can be disposed on the first planar top level and electrically coupled between the two parts of the conductive body and can be configured to electrically couple the two parts together when the conductive body is exposed to electrical signals at a first frequency and electrically disconnect the two parts from one another when the conductive body is exposed to magnetic fields at a second frequency different from the first frequency.

Some embodiments pertain to a portable electronic device that includes a housing having a top portion and a bottom portion configured to mate with the top portion to form an internal cavity. The portable electronic device can further include an antenna as described herein.

In some additional embodiments, a wireless charging receiver system is provided that includes: a primary coil formed of a plurality of turns of stranded wire wound about a primary axis and configured to receive wireless power from time-varying magnetic fields generated at a first frequency and in a first direction; a primary ferromagnetic shield disposed on a top surface of the primary coil; a pair of secondary ferromagnetic structures disposed coplanar with one another and positioned apart from the primary ferromagnetic shield, the pair of secondary ferromagnetic structures include a first ferromagnetic structure and a second ferromagnetic structure; and a secondary coil including a first sub-coil and a second sub-coil, each sub-coil formed of a plurality of turns of stranded wire wound about a center portion of respective first and second ferromagnetic structures, and configured to receive wireless power from time-varying magnetic fields generated at a second frequency different from the first frequency and in a second direction different from the first direction.

Some embodiments pertain to a portable electronic device that includes a housing having a top and bottom portions and defining an internal cavity and a wireless charging receiver system as described herein disposed within the internal cavity.

A better understanding of the nature and advantages of embodiments of the present invention may be gained with reference to the following detailed description and the accompanying drawings.

BRIEF DESCRIPTION OF THE DRAWINGS

FIG. 12A is a perspective view illustration of an exemplary wireless charging receiver system 1200 whose primary and secondary receiving elements are formed as a single structure, according to some embodiments of the present disclosure.

FIG. 12B is a top-down illustration of the wireless charging receiver system shown in FIG. 12A, according to some embodiments of the present disclosure.

FIG. 12C is a bottom-up illustration of the wireless charging receiver system shown in FIG. 12A, according to some embodiments of the present disclosure FIGS. 12D-12E are simplified cross-sectional illustrations of a ferromagnetic structure across different planes through its extended region shown in FIGS. 12A-12C, according to some embodiments of the present disclosure.

FIG. 14A is a perspective view illustration of an exemplary wireless charging receiver system whose primary and secondary receiving elements are formed as a single structure but altered to minimize its size, according to some embodiments of the present disclosure.

FIG. 14B is a top-down illustration of the wireless charging receiver system shown in FIG. 14A, according to some embodiments of the present disclosure.

FIG. 14C is a bottom-up illustration of the wireless charging receiver system shown in FIG. 14A, according to some embodiments of the present disclosure.

FIGS. 14D-14E are simplified cross-sectional illustrations of the ferromagnetic structure across different planes through the straight segment shown in FIGS. 14A-14C, according to some embodiments of the present disclosure.

FIG. 25A is a cross-sectional view illustration of the assembled portion shown in FIG. 19 across the horizontal cut line, according to some embodiments of the present disclosure.

FIG. 25B is a cross-sectional view illustration of the assembled portion shown in FIG. 19 across the vertical cut line, according to some embodiments of the present disclosure.

FIGS. 27A-H are a series of illustrations showing how an internal surface of a window can be coated with different layers in a second configuration, according to some embodiments of the present disclosure.

DETAILED DESCRIPTION OF THE INVENTION

Embodiments of the disclosure describe a portable electronic device that is configured to receive charge from various wireless charging devices and that can fit within a compact enclosure along with an antenna configured for wireless communication. The portable electronic device can be a wearable portable electronic device, such as a smart watch, that has a receiver system designed to include at least two different receiver coils for receiving wireless power from different wireless charging devices. The manner in which the portable electronic device receives power from each wireless charging device can be different from each other.

As an example, each receiver coil can be configured to operate at a specific frequency based on the operating frequency of a wireless charging device from which it receives power. For instance, one receiver coil can be configured to operate at a first frequency, and the other receiver coil can be configured to operate at a second frequency that is different than the first frequency. As another example, each receiver coil can be configured to operate according to different alignment constraints. For instance, one receiver coil can operate when the portable electronic device is substantially aligned with a wireless charging device, whereas the other receiver coil can operate when the portable electronic device is placed upon any region of a broad charging surface. Furthermore, each receiver coil can be configured to receive magnetic field that is propagating in a specific direction. For instance, one receiver coil can be configured to receive magnetic field propagating in a vertical direction, while the other is configured to receive magnetic field propagating in a horizontal direction.

Accordingly, the portable electronic device can receive power from various wireless charging devices, thereby increasing the ease at which the portable electronic device can be charged. Aspects and features of embodiments of such a portable electronic device are discussed in further detail herein.

I. Portable Electronic Device

Figure 1:
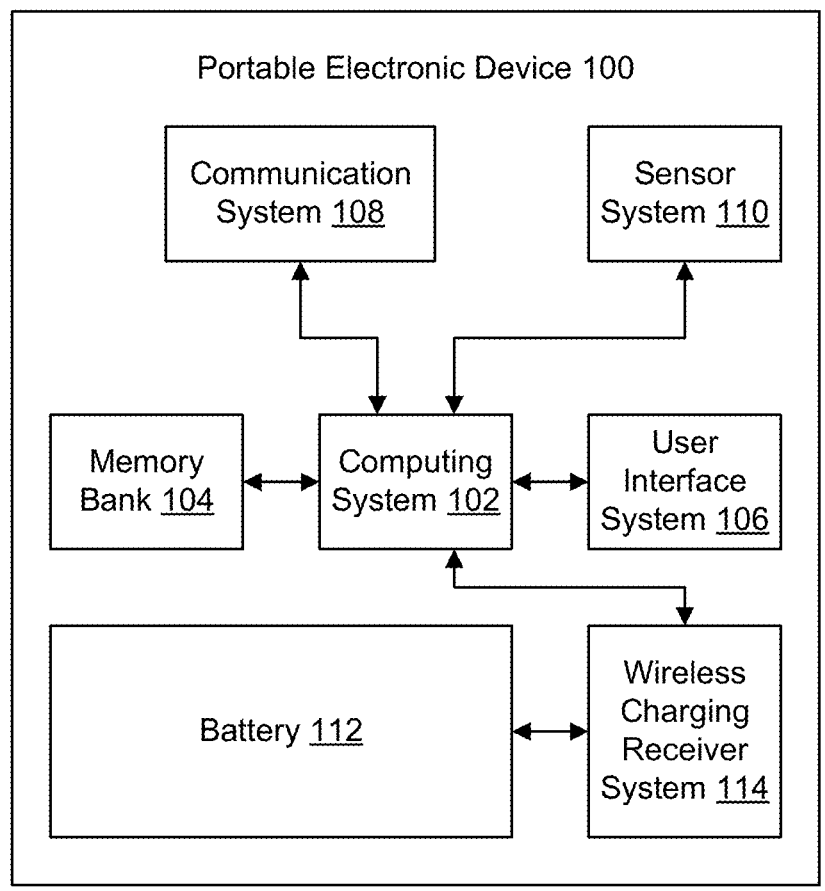
FIG. 1 is a block diagram illustrating an exemplary portable electronic device, according to some embodiments of the present disclosure.

A portable electronic device is an electronic device that can operate without being coupled to a power grid by running on its own locally stored electrical power. FIG. 1 is a block diagram illustrating an exemplary portable electronic device 100, according to some embodiments of the present disclosure. Device 100 includes a computing system 102 coupled to a memory bank 104. Computing system 102 can execute instructions stored in memory bank 104 for performing a plurality of functions for operating device 100. Computing system 102 can be one or more suitable computing devices, such as microprocessors, computer processing units (CPUs), graphics processing units (GPUs), field programmable gate arrays (FPGAs), and the like.

Computing system 201 can also be coupled to a user interface system 106, communication system 108, and a sensor system 110 for enabling electronic device 100 to perform one or more functions. For instance, user interface system 106 can include a display, speaker, microphone, actuator for enabling haptic feedback, and one or more input devices such as a button, switch, capacitive screen for enabling the display to be touch sensitive, and the like. Communication system 108 can include wireless telecommunication components (e.g., antenna components for radio frequency telecommunication), Bluetooth components, and/or wireless fidelity (WiFi) components for enabling device 100 to make phone calls, interact with wireless accessories, and access the Internet. Sensor system 110 can be one or more sensor modules, as will be discussed further herein, that include light sensors, accelerometers, gyroscopes, temperature sensors, heart rate sensors, electrocardiography (EKG) sensors, and any other type of sensor that can measure a parameter of an external entity and/or environment.

All of these electrical components require a power source to operate. Accordingly, portable electronic device 100 also includes a battery 112 for discharging stored energy to power the electrical components of device 100. To replenish the energy discharged to power the electrical components, portable electronic device 100 includes a wireless charging receiver system 114. According to some embodiments of the present disclosure, wireless charging receiver system 114 can be configured to wirelessly receive power from an external source, such as a wireless charging device. For instance, wireless charging receiver system 114 can be one or more inductive receiver coils configured to receive power from one or more transmitter coils in a wireless charging device. The wireless charging device can generate a time-varying magnetic field that interacts with and generates a corresponding current in wireless charging receiver system 114. The generated current can be used to provide energy to battery 112 for replenishing its energy storage so that battery 112 can be discharged at a later time to operate portable electronic device 100 when it is not connected to an external power supply.

In some embodiments, portable electronic device 100 is a consumer electronic device that can perform one or more functions for a user. For instance, portable electronic device 100 can be a smart phone, wearable device, smart watch, tablet, personal computer, and the like.

II. Wireless Charging Receiver System for a Portable Electronic Device

According to some embodiments of the present disclosure, a wireless charging system for a portable electronic device can include at least two receiver coils for receiving power from different wireless charging devices. Each receiver coil can be configured to receive power according to different charging constraints and parameters, such as alignment constraints and operating frequency, that are defined by the particular wireless charging device from which it receives power.

Figure 2:
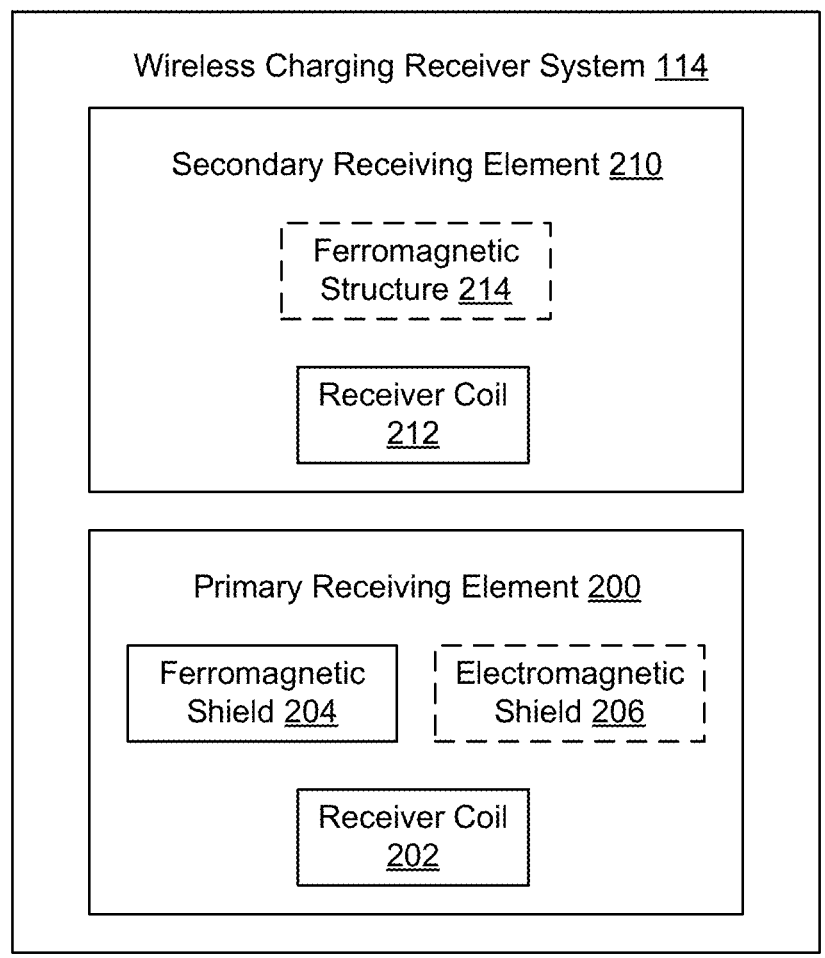
FIG. 2 is a block diagram illustrating the inner components of a wireless charging receiver system, according to some embodiments of the present disclosure.

FIG. 2 is a block diagram illustrating the inner components of wireless charging receiver system 114, according to some embodiments of the present disclosure. Wireless charging receiver system 114 can include two elements: a primary receiving element 200 and a secondary receiving element 210, for receiving power from different wireless charging devices. Each element can include a receiver coil and at least one element can include a shield or structure for redirecting the flow of magnetic field and/or for capturing stray electric fields.

In some embodiments, primary receiving element 200 can include a primary receiver coil 202, a primary ferromagnetic shield 204, and an optional electromagnetic shield 206 that are tuned to maximize the efficiency of power transfer from a wireless charging device that is specifically designed to provide power to portable electronic device 100. Thus, primary receiver coil 202 can be configured to receive power according to an alignment constraint and operating frequency defined by the wireless charging device, as discussed herein with respect to FIG. 3A.

Figure 3A:
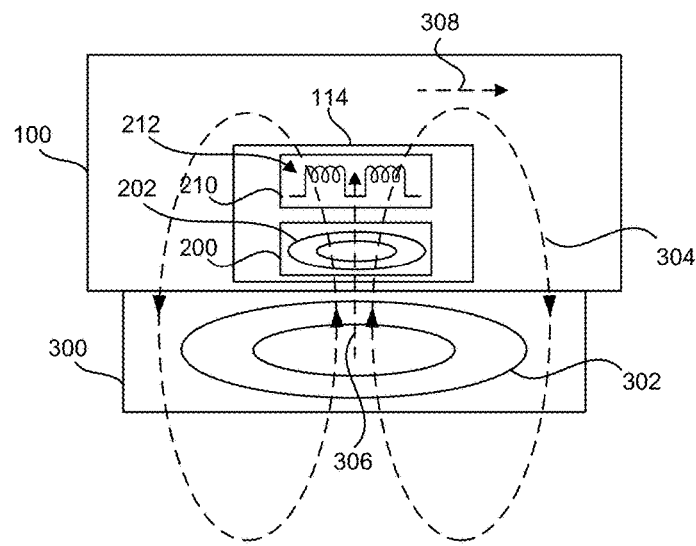
FIG. 3A is a block diagram of a portable electronic device placed against a wireless charging device that is specifically designed to provide wireless power to the portable electronic device, according to some embodiments of the present disclosure.

FIG. 3A is a block diagram of portable electronic device 100 placed against a wireless charging device 300 that is specifically designed to provide wireless power to portable electronic device 100, according to some embodiments of the present disclosure. Wireless charging device 300 includes a transmitter coil 302 that is configured to generate a time-varying magnetic field 304 at a primary frequency, and provide power to a receiving device when it is substantially aligned with a receiver coil in the receiving device. Thus, in some embodiments, primary receiver coil 202 in device 100 is configured to operate at the primary frequency and to receive power when it is substantially aligned with transmitter coil 302. As an example, primary receiver coil 202 can receive power from time-varying magnetic field 304 at a primary frequency of between 6 to 7 MHz, particularly approximately 6.78 MHz in some embodiments, and when its axis is aligned with the axis of transmitter coil 302.

During operation of transmitter coil 302, time-varying magnetic field 304 can propagate along field loops around transmitter coil 302 as shown in FIG. 3A. The direction of propagation can include vertical components 306 and horizontal components 308 as time-varying magnetic field 304 propagates along the field loops. By being able to substantially align with transmitter coil 302, primary receiver coil 202 can receive power from vertical components 306 of transmitter coil 302. Thus, primary receiver coil 202 can be configured to receive magnetic field propagating in the vertical direction. For instance, primary receiver coil 202 can have a central axis that is parallel to the vertical direction such that magnetic field propagating in the vertical direction can induce a corresponding current in primary receiver coil 202. Field propagating with a degree of horizontal movement 308 may not substantially pass through the inner diameter of primary receiver coil 202 and thus may result in little to no generation of power in primary receiver coil 202.

With reference back to FIG. 2, unlike primary receiving element 200, a secondary receiving element 210 can include a secondary receiver coil 212 and an optional secondary ferromagnetic structure 214 that are configured to receive power from a wireless charging device that is designed to provide power to a several different types of electrical devices. For instance, receiver coil 212 can be configured to receive power from a wireless charging mat that has a broad charging surface for charging different types of devices, including portable electronic device 100. Thus, secondary receiver coil 212 can be configured to receive power according to the alignment constraint and operating frequency defined by the wireless charging device. As will be discussed further herein, for embodiments where the primary and secondary receiving elements 200 and 210 are formed as separate structures, secondary receiving element 210 may include ferromagnetic structure 214, and in embodiments where the primary and secondary receiving elements 200 and 210 are formed as a single structure, secondary receiving element 210 may not include ferromagnetic structure 214.

Figure 3B:
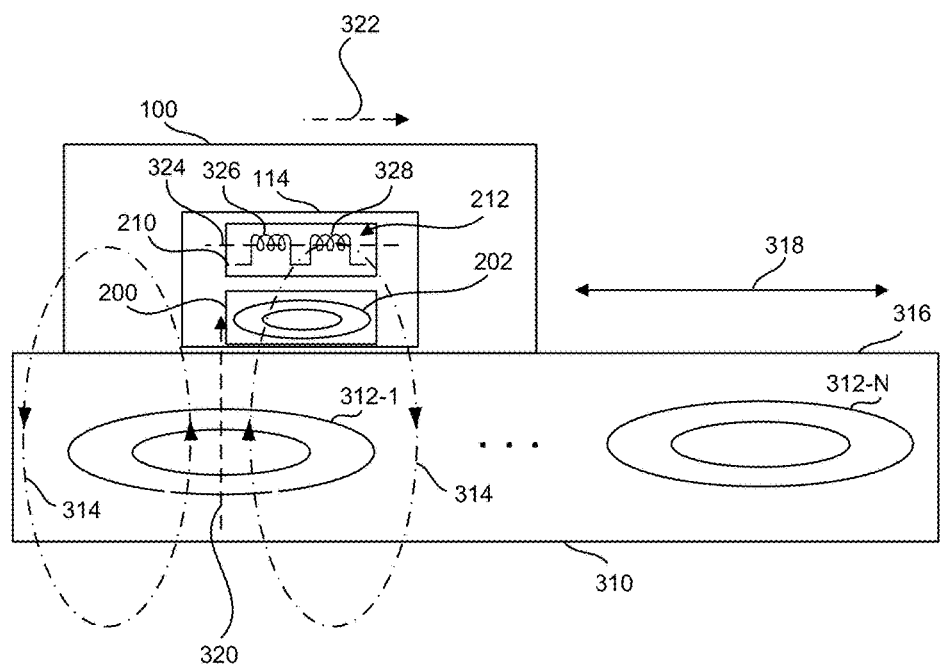
FIG. 3B is a block diagram of a portable electronic device placed against a wireless charging device that is configured to provide power to more than one type of portable electronic device, according to some embodiments of the present disclosure.

FIG. 3B is a block diagram of portable electronic device 100 placed against a wireless charging device 310 that is configured to provide power to more than one type of portable electronic device, according to some embodiments of the present disclosure. Wireless charging device 310 can include N number of transmitter coils ranging from 312-1 to 312-N. Transmitter coils 312-1 to 312-N can be organized as a transmitter coil arrangement that provides a broad charging surface 316 upon which electronic devices can be charged. The broad charging surface allows electronic devices to be charged anywhere within charging surface 316. Thus, portable electronic device 100 can be positioned along any area 318 of charging surface 316 to receive power from wireless charging device 310. Furthermore, the broad charging surface allows more than one electronic device of the same type or different types to charge from wireless charging device 310.

Transmitter coils 312-1 to 312-N can be configured to generate time-varying magnetic field 314 at a secondary frequency, and provide power to a receiving device when the receiving device is resting upon any region of charging surface 316. Thus, in some embodiments, secondary receiving element 210 in device 100 is configured to operate at the secondary frequency and to receive power when it is resting on charging surface 316 in any degree of alignment with transmitter coils 312-1 to 312-N. According to some embodiments, the secondary frequency at which secondary receiving element 210 operates can be different than the primary frequency at which primary receiving element 200 operates. In some embodiments, the secondary frequency is less than the primary frequency. For instance, secondary receiver coil 212 can receive power from time-varying magnetic field 314 at a secondary frequency of between 300 to 400 kHz, particularly approximately 326 kHz in some embodiments. Because the secondary frequency is different than the primary frequency, when secondary receiving element 210 is receiving charge, primary receiving element 200 may not substantially receive charge, and vice versa.

During operation of each transmitter coil, such as transmitter coil 312-1 shown in FIG. 3B, time-varying magnetic field 314 can propagate along field loops around transmitter coil 312-1 as shown in FIG. 3B. The direction of propagation can include vertical components 320 and horizontal components 322 as time-varying magnetic field 314 propagates along the field loops. As can be seen in FIG. 3B, portable electronic device 100 can be positioned on charging surface 316 so that it is not aligned with transmitter coil 312-1. In some embodiments, secondary receiver coil 212 can be configured to receive horizontal components 322 of magnetic field 314, and thus receive power from transmitter coil 312-1. For instance, secondary receiver coil 212 can have a central axis 324 that is parallel to the horizontal direction such that magnetic field propagating in the horizontal direction can induce a corresponding current in secondary receiver coil 212. Field propagating with a degree of vertical movement 320 may not substantially pass through the inner diameter of secondary receiver coil 212 and thus may result in little to no generation of power in secondary receiver coil 212.

In some embodiments, secondary receiver coil 212 can be formed of two sub-coils: a first sub-coil 326 and a second sub-coil 328. Both first and second sub-coils can be wound in the same direction. For instance, both first and second sub-coils can be wound in the clockwise direction or counter-clockwise direction. By winding both first and second sub-coils in the same direction, both sub-coils 326 and 328 can generate power from magnetic fields propagating in the same horizontal direction, thereby increasing the efficiency at which secondary receiver coil 212 receives power. In some embodiments, first and second sub-coils 326 and 328 are electrically coupled together, such as in a series arrangement or a parallel arrangement. When electrically coupled together, power generated in both sub-coils 326 and 328 can aggregate into a larger magnitude of received power. Details regarding the construction of the primary and secondary receiving elements 200 and 210 are discussed further herein with respect to FIGS. 4A-9. In some embodiments, secondary receiver coil 212 can be formed of a single coil. In such instances, secondary receiver coil 212 can be a separate component that winds around a separate ferromagnetic structure, or it can wind around a portion of primary receiver coil 202 as will be discussed further herein with respect to FIGS. 12A-14B.

III. Construction of Primary and Secondary Receiving Elements

As can be understood from FIGS. 3A and 3B, primary receiver coil 202 and secondary receiver coil 212 are designed to operate at different frequencies and different alignment constraints to receive power from different wireless charging devices. This difference in operation can be achieved in part by having different physical constructions and orientations. In some instances, the primary and secondary receiving elements can be separate, individual components positioned at different locations within the portable electronic device. Alternatively, the primary and secondary receiving elements can be part of a single component where the secondary receiver coil winds around a portion of the primary receiver coil. Exemplary constructions of such primary and secondary receiving elements are discussed herein with respect to FIGS. 4A-8 and FIGS. 12A-14B.

A. Primary and Secondary Receiving Elements Constructed as Separate Components

Figure 4A:
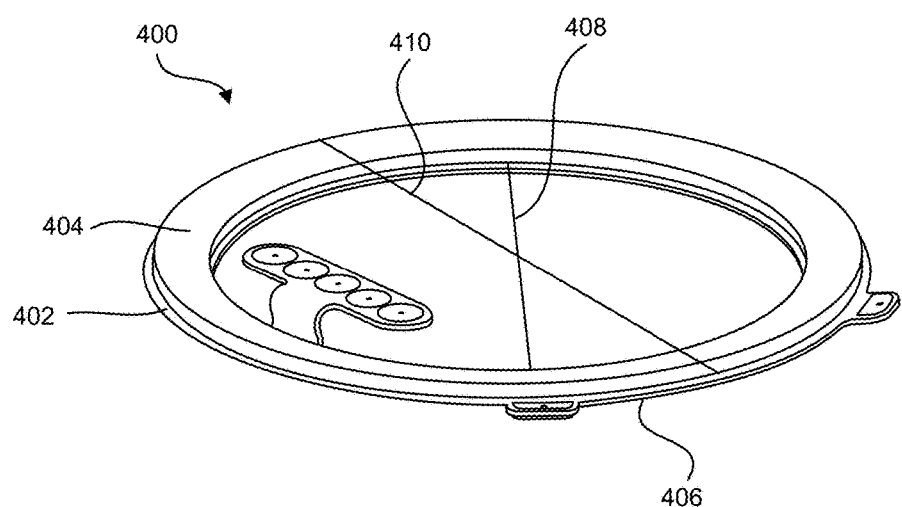
FIG. 4A is a perspective view illustration of an exemplary primary receiving element that includes a primary receiver coil formed as a flex coil, according to some embodiments of the present disclosure.

FIG. 4A illustrates an exemplary primary receiving element 400 that includes a primary receiver coil 402 formed as a flex coil for a receiver system configured to have a separate secondary receiving element, according to some embodiments of the present disclosure. Primary receiving element 400 can include a ferromagnetic shield 404 attached to a first side of primary receiver coil 402 and an electromagnetic shield 406 attached to a second side of primary receiver coil 402 opposite of the first side.

Ferromagnetic shield 404 can help redirect magnetic field through an inner diameter 408 of primary receiver coil 402 to increase efficiency of wireless power transfer and to mitigate stray field from propagating to disturb other electrical components within the electronic device. In some embodiments, ferromagnetic shield 404 has a shape that substantially corresponds with a shape of primary receiver coil 402. For instance, ferromagnetic shield 404 can be in the shape of a circular ring. Ferromagnetic shield 404 can be formed of any suitable material that has magnetic properties and is particularly attractive to magnetic field generated at the primary frequency and less attractive to magnetic field generated at the secondary frequency. For instance, ferromagnetic shield 404 can be particularly attractive to magnetic field generated at a high frequency, such as between 6 to 7 MHz (e.g., the frequency at which wireless charging device 300 operates). For instance, ferromagnetic shield 404 can be formed of a material containing nickel-zinc (NiZn).

Electromagnetic shield 406 can be configured to capture electric fields emanating from primary receiver coil 402 to prevent voltage from generating on a transmitter coil. Voltage built up in electromagnetic shield 406 from exposure to electric fields can be discharged to ground. In some embodiments, electromagnetic shield 406 is formed of a thin layer of conductive material, such as silver. Electromagnetic shield 406 can be positioned closer to the transmitter coil than ferromagnetic shield 404 during wireless power transfer.

Primary receiver coil 402 can be formed of one or more windings of a single length of conductive material patterned on a flexible circuit board. The one or more windings can form a spirally-wound coil that winds between an inner diameter 408 and an outer diameter 410. In some embodiments, primary receiver coil 402 is formed of more than one layer of windings that wind from outer diameter 410 to inner diameter 408 in one layer, and back from inner diameter 408 to outer diameter 410 in an adjacent layer. In other embodiments, primary receiver coil 402 is a symmetrical coil that is formed of a winding having crossing portions, as shown in FIG. 4B.

Figure 4B:
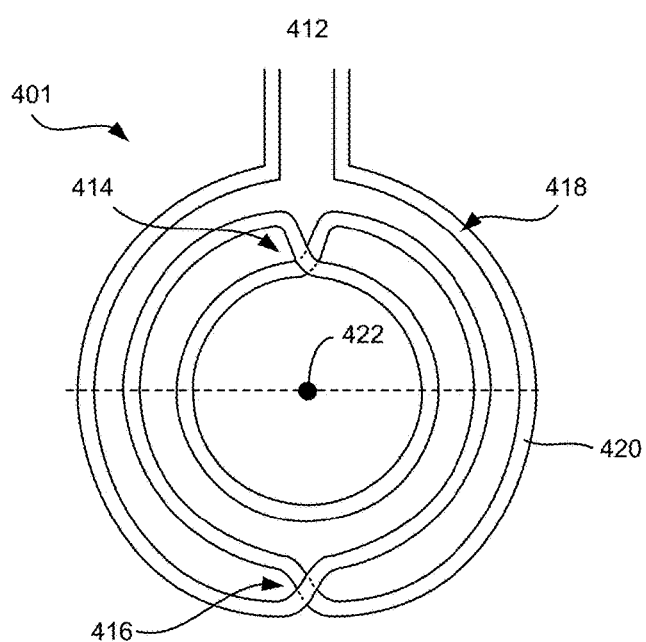
FIG. 4B is a top-down view of an exemplary symmetrical primary receiver coil having symmetric windings, according to some embodiments of the present disclosure.

FIG. 4B is a top-down view of an exemplary symmetrical primary receiver coil 401 having symmetric windings, according to some embodiments of the present disclosure. Winding 420 can begin and end at location 412 and have crossing-over portions 414 and 416 that allow symmetrical primary receiver coil 401 to be symmetrical across a vertical and horizontal axis. The symmetrical profile results in a decrease in capacitive coupling between symmetrical primary receiver coil 401 and a transmitter coil form which it receives power during wireless power transfer. In some embodiments, primary receiver coil 402 includes two layers of coils connected in a parallel configuration. For instance, two layers of coils where each layer is arranged as shown in FIG. 4B can be implemented as primary receiver coil 401. The two layers can be positioned above and below one another such that they share the same central axis 422.

Figure 5A:
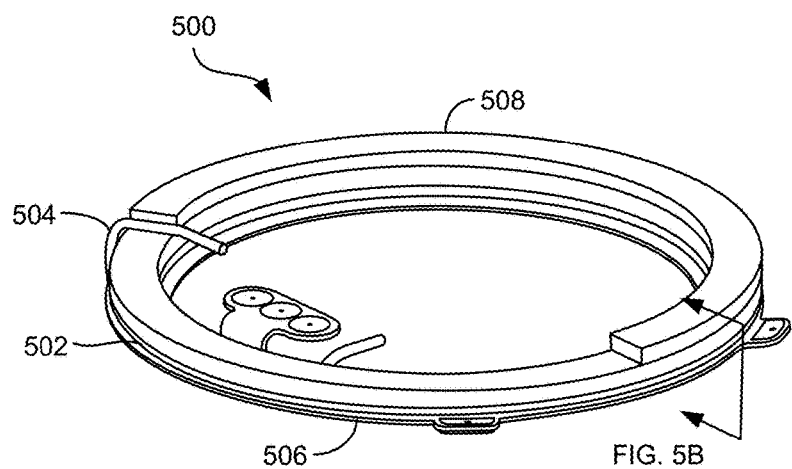
FIG. 5A is a perspective view of an exemplary primary receiving element including a stranded primary receiver coil, according to some embodiments of the present disclosure.
Figure 5B:
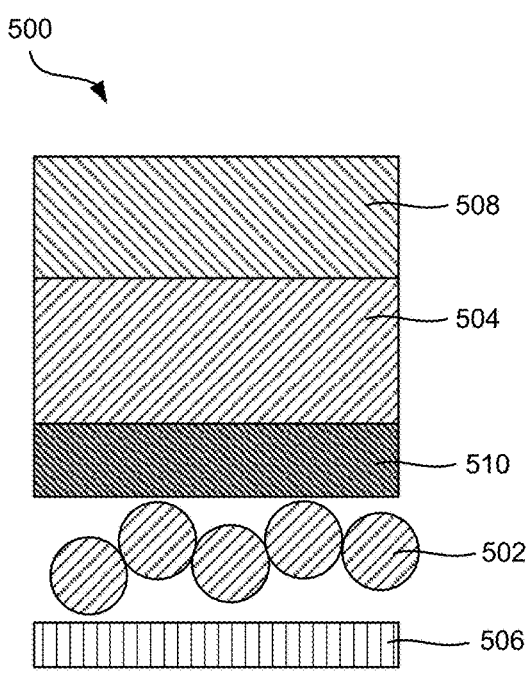
FIG. 5B is a cross-sectional illustration of the primary receiving element illustrated in FIG. 5A, according to some embodiments of the present disclosure.

Although primary receiving element 200 can include a primary receiver coil 202 formed as a flex coil, other embodiments can have receiver coil 202 formed as a stranded coil as shown in FIGS. 5A-5B. FIG. 5A is a perspective view of an exemplary primary receiving element 500 including a stranded primary receiver coil 502, ferromagnetic shield 504, electromagnetic shield 506 and a guide structure 508 for a receiver system configured to have a separate secondary receiving element, according to some embodiments of the present disclosure. Ferromagnetic shield 504 can be disposed above primary receiver coil 502, and electromagnetic shield 506 can be disposed below primary receiver coil 502. Ferromagnetic shield 504 and electromagnetic shield 506 can have similar properties, materials, and functions of ferromagnetic shield 404 and electromagnetic shield 406 discussed herein with respect to FIG. 4.

In some embodiments, primary receiving element 500 can also include a guide structure 508. Guide structure 508 can extend around at least a portion of primary receiving element 500. In particular embodiments, guide structure 508 be a stiff structure that provides structural support for primary receiving element 500 to resist against bending or other physical deformations.

FIG. 5B is a cross-sectional illustration of primary receiving element 500, according to some embodiments of the present disclosure. As shown in FIG. 5B, guide structure 508 and ferromagnetic shield 504 can both be disposed above primary receiver coil 502. In some embodiments, guide structure 508 and ferromagnetic shield 504 can be attached to primary receiver coil 502 by an intermediary layer. For instance, a spacer layer 510 can attach primary receiver coil 502 to ferromagnetic shield 504, and provide a degree of separation between them. In certain embodiments, spacer layer 510 is formed of pressure sensitive adhesive (PSA).

As shown in FIGS. 5A and 5B, ferromagnetic shield 504 can be a structure that is disposed above primary receiver coil 502 and that functions to help redirect magnetic field through primary receiver coil 502. In some cases, the structure of ferromagnetic shield can be modified to improve its ability to redirect magnetic field through primary receiver coil 502 and thus improve wireless charging efficiency. An example of a modified ferromagnetic shield is discussed herein with respect to FIGS. 6A and 6B.

Figure 6A:
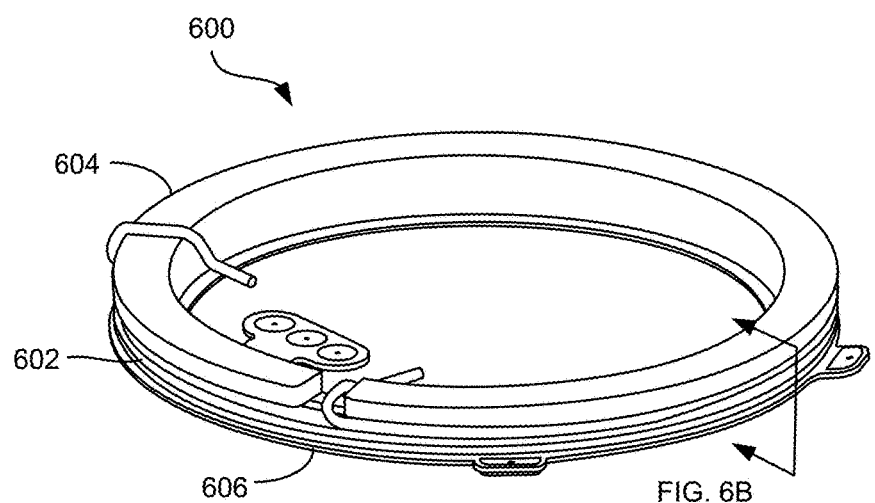
FIG. 6A is a perspective view of an exemplary primary receiving element including a stranded primary receiver coil and a modified ferromagnetic shield, according to some embodiments of the present disclosure.

FIG. 6A is a perspective view of an exemplary primary receiving element 600 including a stranded primary receiver coil 602, a modified ferromagnetic shield 604, and an electromagnetic shield 606, according to some embodiments of the present disclosure.

Ferromagnetic shield 604 and electromagnetic shield 606 can have similar properties, materials, and functions of ferromagnetic shield 404 and electromagnetic shield 406 discussed herein with respect to FIG. 4. As shown in FIG. 6A, ferromagnetic shield 604 may differ from ferromagnetic shield 504 in FIG. 5B in that a portion of modified ferromagnetic shield 604 can extend downward and be positioned lateral to primary receiver coil 602. In some embodiments, the side of primary receiver coil 602 to which modified ferromagnetic shield 604 is laterally disposed is a side that is closest to a center axis of primary receiver coil 602. By positioning modified ferromagnetic shield 604 on that side, it can better assist in redirecting magnetic field through primary receiver coil 602 to increase charging efficiency.

Figure 6B:
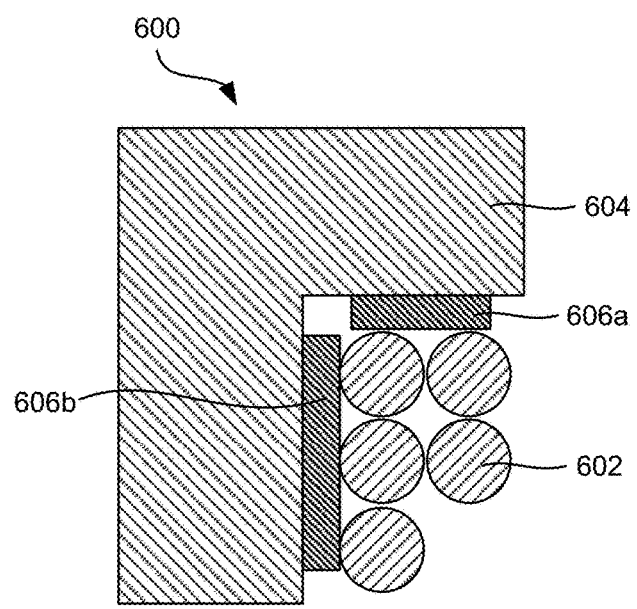
FIG. 6B is a cross-sectional illustration of the primary receiving element illustrated in FIG. 6A, according to some embodiments of the present disclosure.

FIG. 6B is a cross-sectional illustration of primary receiving element 600, according to some embodiments of the present disclosure. As shown in FIG. 6B, modified ferromagnetic shield 604 can be disposed both above and beside primary receiver coil 602. By extending shield 604 downward to a position lateral to receiver coil 602, modified ferromagnetic shield 604 can be positioned closer to the transmitter coil from which it receives magnetic field, and can be better positioned to redirect the received magnetic field through primary receiver coil 602. In some embodiments, modified ferromagnetic shield 604 can be attached to primary receiver coil 602 by at least one intermediate layer, such as spacer layer 606a and 606b. Spacer layer 606a can be positioned to attach a portion of modified ferromagnetic shield 604 disposed above primary receiver coil 602 with a top surface of primary receiver coil 602. Spacer layer 606b can be positioned to attach a portion of modified ferromagnetic shield 604 disposed lateral to primary receiver coil 602 with a side surface of primary receiver coil 602. The side surface can be an inner side surface that is positioned closest to a center axis of primary receiver coil 602. Similar to spacer layer 510, spacer layer 610 can be formed of PSA.

Figure 7:
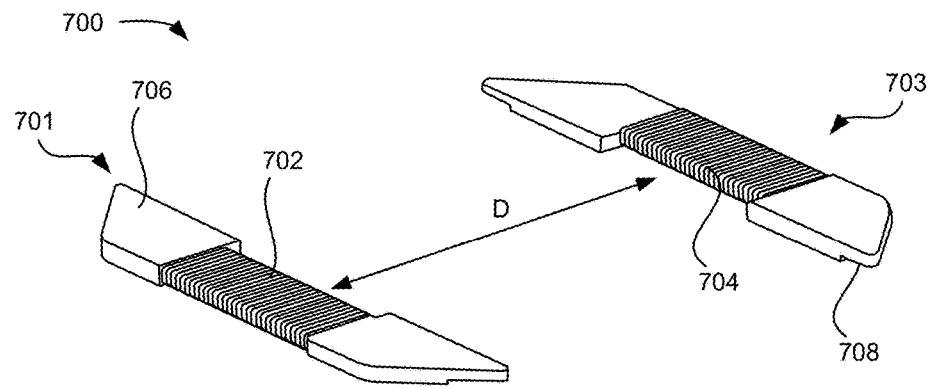
FIG. 7 is a perspective view illustration of an exemplary secondary receiving element, according to some embodiments of the present disclosure.

FIG. 7 illustrates a perspective view of an exemplary secondary receiving element 700, according to some embodiments of the present disclosure. Secondary receiving element 700 can include a secondary receiver coil formed of a first coil subassembly 701 and a second coil subassembly 703. First and second coil subassemblies 701 and 703 can be positioned a distance D away from each other to minimize coupling between the two subassemblies, and to provide space within which other electronic components within the portable electronic device can be positioned.

Each coil subassembly can include multiple parts; for instance, first coil subassembly 701 can include a first sub-coil 702 and a first ferromagnetic structure 706, and second coil subassembly 703 can include a second sub-coil 704 and a second ferromagnetic structure 708. First sub-coil 702 can be wound about a central portion of first ferromagnetic structure 706, and second sub-coil 704 can be wound about a central portion of second ferromagnetic structure 708. By winding sub-coils 702 and 704 around their respective ferromagnetic structures 706 and 708, first and second ferromagnetic structures 706 and 708 can redirect magnetic field through first and second transmitter sub-coils 702 and 704, respectively, and thereby increase power transfer efficiency.

In some embodiments, first and second sub-coils 702 and 704 are coupled together in a series configuration. Thus, power received by both first and second sub-coils 702 and 704 can be inputted into a single rectifier to convert alternating current (AC) power to direct current (DC) power. By coupling the first and second sub-coils 702 and 704 together, secondary receiving element can cover more surface area as it rests on the wireless charging device, thereby allowing the portable electronic device to capture more magnetic field during wireless power transfer and minimizing instances where portable electronic device is not capturing any magnetic field (e.g., sitting in a dead zone). Although it is disclosed that first and second sub-coils 702 and 704 share a single rectifier, embodiments are not so limited. Other embodiments can decouple first and second sub-coils 702 and 704 so that each sub-coil is coupled to its own rectifier. In such instances, each sub-coil can operate independently from each other.

Ferromagnetic structures 706 and 708 can be formed of any suitable material that has magnetic properties and is particularly attractive to magnetic field generated at the secondary frequency and less attractive to magnetic field generated at the primary frequency. In some embodiments, the secondary frequency is lower than the primary frequency. For instance, ferromagnetic structures 706 and 708 can be formed of a material that is particularly attractive to magnetic field generated at a low frequency, such as between 300-400 kHz, particularly 326 kHz (e.g., the frequency at which wireless charging device 310 in FIG. 3B operates). In certain embodiments, the magnetic permeability of the material used to form ferromagnetic structures 706 and 708 in secondary receiving element 700 is substantially larger than the magnetic permeability of the material used to form ferromagnetic shields 404, 504, and 604 in primary receiving elements 400, 500, and 600, respectively. As an example, ferromagnetic structures 706 and 708 are formed of a material having a magnetic permeability of greater than 3000, such as a material containing manganese-zinc (MnZn), while ferromagnetic shields 404, 504, and 604 can be formed of a material having a magnetic permeability of less than 500, such as 200 in some embodiments. Thus, ferromagnetic structures 706 may have greater losses for magnetic fields generated in higher frequencies (e.g., 6-7 MHz) and less losses for magnetic fields generated in lower frequencies (e.g., 300-400 KHz). The opposite can be said for ferromagnetic shields 404, 504, and 604.

Figure 8:
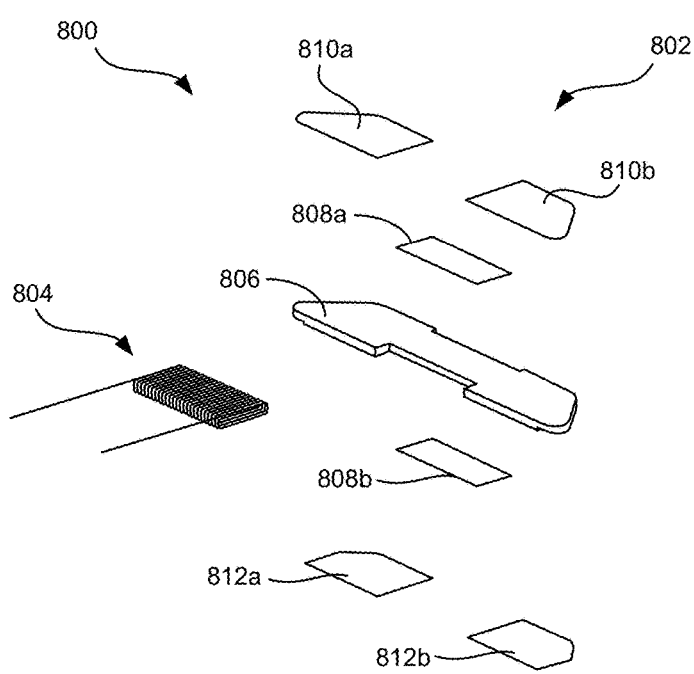
FIG. 8 is an exploded view illustration of an exemplary coil subassembly, according to some embodiments of the present disclosure.

Each ferromagnetic structure 706 or 708 can be formed of a plurality of individual parts. FIG. 8 is an exploded view illustration of an exemplary coil subassembly 800, according to some embodiments of the present disclosure. Coil subassembly 800 can include a ferromagnetic structure 802 and a coil of wire 804. Ferromagnetic structure 802 can include a ferrite body 806 sandwiched between two support layers 808a and 808b. Ferrite body 806 can be a structure that forms the bulk of ferromagnetic structure 802 and includes material suitable for redirecting magnetic field, such as sintered ferrite formed of MnZn. Support layers 808a and 808b can be layers of tape that protect surfaces of ferrite body 806 from physical damage, such as damage from coil of wire 804 when coil of wire 804 is wound around ferrite body 806. Thus, in some embodiments, coil of wire 804 is wound around ferrite body 806 and both support layers 808a and 808b. In some embodiments, support layers 808a and 808b can be disposed on opposite surfaces of ferrite body 806. As an example, support layer 808a can be disposed on a top surface of ferrite body 806, and support layer 808b can be disposed on a bottom surface of ferrite body 806. Support layers 808a and 808b can be formed of any non-conductive material that can withstand physical stresses, such as Polyethylene Terephthalate (PET).

Ferromagnetic structure 802 can also include protective layers 810a and 810b that are attached to a surface of ferrite body 806. For instance, protective layers 810a and 810b can be attached to a top surface of ferrite body 806 where support layer 808a is not positioned. Protective layers 810a and 810b can protect top surfaces of ferrite body 806 from damage during assembly. In some embodiments, protective layers 810a and 810b are also formed of a magnetic material including ferrite.

In some embodiments, adhesive layers 812a and 812b can be disposed on a surface of ferrite body 806. For instance, adhesive layers 812a and 812b can be disposed on a bottom surface of ferrite body 806 where support layer 808b is not positioned. Adhesive layers 812a and 812b can be formed of any suitable material that can attach two structures together, such as a pressure sensitive adhesive (PSA). Adhesive layers 812a and 812b can fix coil subassembly 800 in position when assembled in a portable electronic device. Although FIGS. 7 and 8 show a secondary receiving element formed with two sub-coils, embodiments are not limited to such configurations. Other embodiments can have more or less than two coils wound about respective ferromagnetic structures, such as a single coil wound about a single ferromagnetic structure, or three or more coils wound about three or more respective ferromagnetic structures without departing from the spirit and scope of the present disclosure.

1. Construction of a Portable Electronic Device Having a Secondary Receiving Element Formed of at Least Two Sub Coils The size and shape of primary and secondary receiver elements depend on the amount of available space provided by the other electrical components in the portable electronic device. As can be appreciated by disclosures herein, the size and shape of the receiver elements can be determined by balancing the trade-off between performance of the receiver elements and the performance of other electrical components in the portable electronic device.

Figure 9:
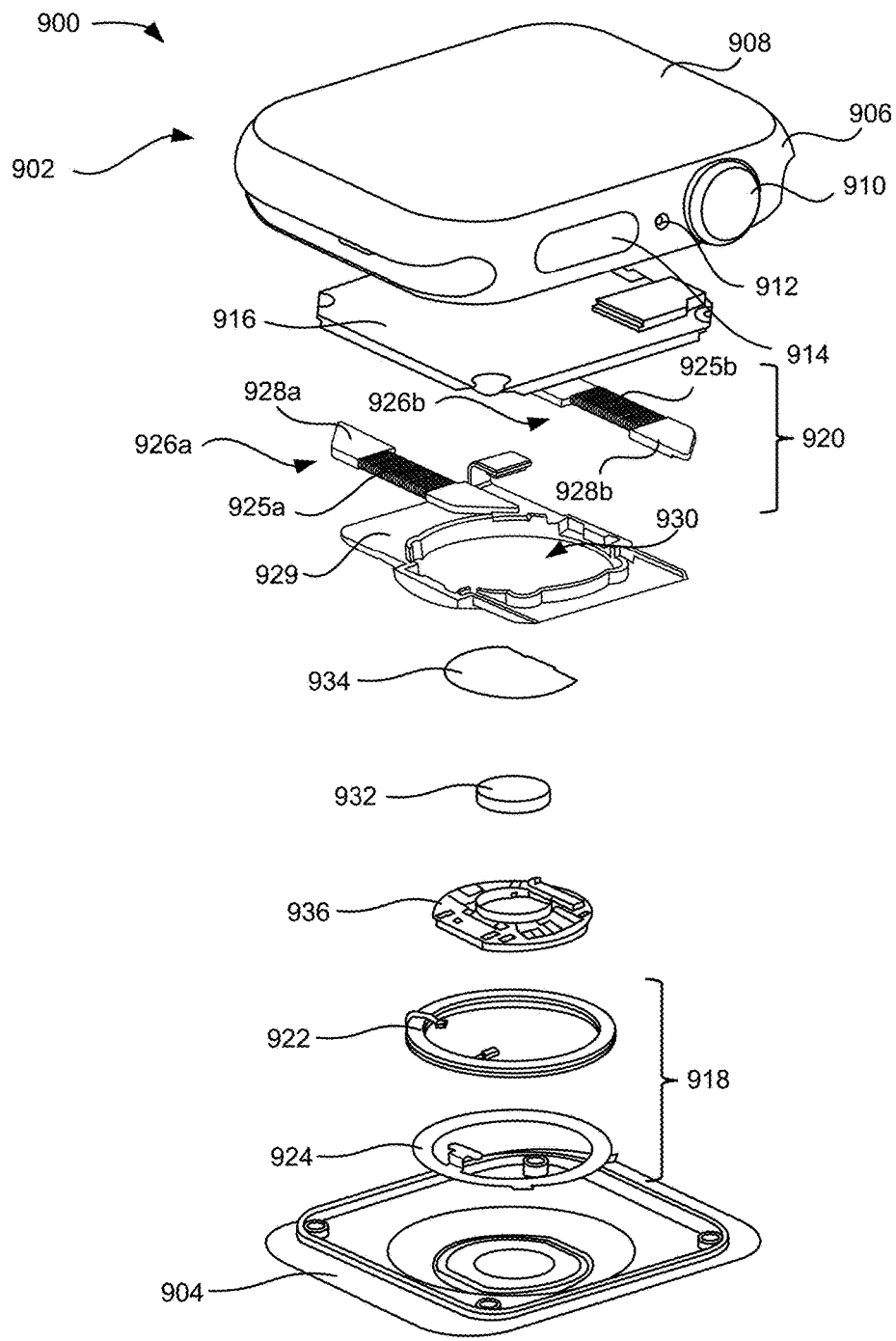
FIG. 9 is an exploded view illustration of an exemplary portable electronic device, according to some embodiments of the present disclosure.

FIG. 9 illustrates an exploded view of an exemplary portable electronic device 900, according to some embodiments of the present disclosure. Portable electronic device 900 can include a top housing portion 902 and a bottom housing portion 904 that can mate to define an interior cavity. Top housing portion 902 can include a device chassis 906 and a transparent panel 908. Transparent panel 908 is a protective, optically transparent structure for a display so that a user can view the display through transparent panel 908 while transparent panel 908 protects the display from damage. Top housing portion 902 can include one or more user interface components, such as a dial 910, microphone 912, power button 914, and any other suitable user interface components.

In some embodiments, dial 910 can be a touch sensitive dial that can act as a contact for performing EKG sensing. Dial 910 can include various components that, when coupled together, form a conductive pathway from an outer surface of dial 910 to inner touch components, which is discussed further herein with respect to FIGS. 35 and 36.

Portable electronic device 900 can further include a system in package (SIP) 916 that is housed within the interior cavity. SIP 916 can be a number of integrated circuits (ICs) enclosed in a single module that can operate to perform several functions of portable electronic device 900. Each IC in SIP 916 can perform one or more different functions, such as performing heart rate monitoring, operating a touch screen display, outputting sound through one or more speakers, processing sound received by microphone 912, managing wireless power transfer, and the like.

According to some embodiments of the present disclosure, portable electronic device 900 can include a primary receiving element 918 and a secondary receiving element 920. Primary and secondary receiving elements 918 and 920 can be positioned within the interior cavity and below SIP 916. As discussed herein, primary receiving element 918 can include a primary receiver coil 922 (shown with a ferromagnetic shield) and an electromagnetic shield 924 that are configured to receive magnetic field generated at a primary frequency and propagating in a vertical direction, as discussed herein with respect to FIGS. 3A and 4A-6B. Secondary receiving element 920 can include first and second coil subassemblies 926a and 926b configured to receive magnetic field generated at a secondary frequency lower than the primary frequency and propagating in a horizontal direction, as discussed herein with respect to FIGS. 3B, 7 and 8. First and second subassemblies 926a and 926b can include first and second ferromagnetic structures 928a and 928b and first and second sub-coils 925a and 925b, respectively.

In some embodiments, portable electronic device 900 can also include an antenna 929 within the interior cavity and below SIP 916. Antenna 929 can include an opening 930 within which one or more other electronic components of portable electronic device 900 can be positioned. For instance, primary receiving element 918 can be disposed within opening 930 and below at least a portion of antenna 929, and secondary receiving element 920 can be positioned above at least a portion of antenna 929. In some embodiments, first and second subassemblies 926a and 926b are positioned on opposite ends of antenna 929. As mentioned herein with respect to FIG. 7, first and second subassemblies 926a and 926b can be separated by a distance D. Accordingly, antenna 929 can be positioned within the space provided by distance D. Further details of their positioning will be discussed herein with respect to FIG. 11. Antenna 929 can be a structure configured to receive and/or send data through radio waves. As an example, antenna 929 can be an antenna configured for long-term evolution (LTE) wireless communications. Such antennas may perform better when their size is maximized, and when conductive electronic components are positioned away from it.

As discussed herein with respect to FIG. 7, the size of ferromagnetic structures 928a and 928b impacts the efficiency at which secondary receiving element 920 receives wireless power. Larger ferromagnetic structures 928a and 928b can increase the efficiency of wireless power transfer because the larger structures can redirect more magnetic field. However, larger ferromagnetic structures take up more space within the portable electronic device and leave less space for antenna 929. Decreasing the amount of space for antenna 929 can negatively affect the performance of antenna 929. Thus, a conflict of interest with respect to component size can exist between antenna 929 and secondary receiving element 920 due to their close proximity with one another. Details of this relationship is discussed further herein with respect to FIGS. 10A-C.

Figure 10:
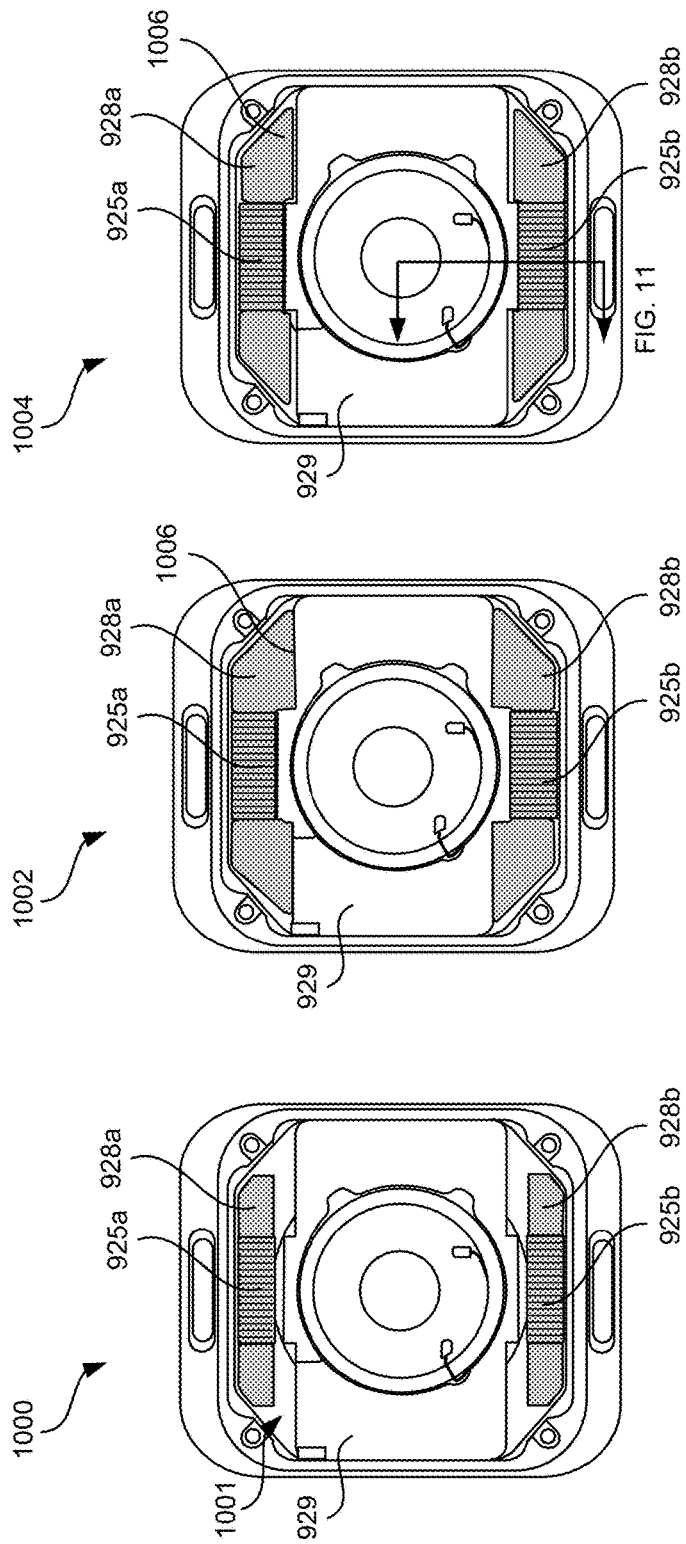
FIGS. 10A-10C are top down view illustrations of different sizing arrangements between secondary receiving elements and an antenna when assembled in a portable electronic device, according to some embodiments of the present disclosure.

FIGS. 10A-10C illustrate top down views of different sizing arrangements between secondary receiving elements 920 and antenna 929 when assembled in a portable electronic device, according to some embodiments of the present disclosure. Specifically, FIG. 10A, illustrates a top-down view of a sizing arrangement 1000 that is more beneficial for antenna 929, FIG. 10B illustrates a top down-view of a sizing arrangement 1002 that is more beneficial for secondary receiving element 920, and FIG. 10C illustrates a top-down view of a sizing arrangement 1004 that strikes a balance between operating efficiencies of both antenna 929 and secondary receiving element 920.

As shown by sizing arrangement 1000 in FIG. 10A, the size of antenna 929 and space 1001 surrounding antenna 929 is enlarged to enhance the operation of antenna 929. This, however, results in a shrinkage of ferromagnetic structures 928a and 928b. Shrinking the size of ferromagnetic structures 928a and 928b decreases wireless charging efficiency because ferromagnetic structures 928a and 928b become smaller and thus less effective at redirecting magnetic field.

On the other hand, enlarging ferromagnetic structures 928a and 928b to maximize charging efficiency can hinder the operation of antenna 929. As shown by sizing arrangement 1002 in FIG. 10B, the size of ferromagnetic structures 928a and 928b can be enlarged to increase the charging efficiency of secondary receiving element 920. One way to enlarge ferromagnetic structures 928a and 928b is to provide protruding portions 1006 that encroach into the space for antenna 929. These protruding portions can extend toward antenna 929 past edges of sub-coils 925a and 925b. Enlarging the size of ferromagnetic structures 928a and 928b however results in a corresponding decrease in the size of antenna 929 and its surrounding space 1001. This decrease in size and space hinders the operation of antenna 929.

Thus, according to some embodiments of the present disclosure, the sizes of ferromagnetic structures 928a and 928b, antenna 929, and space 1001 surrounding antenna 929 can be optimized to achieve acceptable levels of both antenna operation and charging efficiency, as shown in sizing arrangement 1004 in FIG. 10C. The resulting ferromagnetic structures 928a and 928b can still have protruding portions 1006, but the degree at which protruding portions 1006 extend past edges of sub-coils 925a and 925b may be lessened.

With reference back to FIG. 9, portable electronic device 900 can also include an alignment mechanism 932 disposed between a DC shield 934 and a sensor module 936. Alignment module 932 can be a permanent magnet designed to attract another alignment magnet in a wireless charging device for aligning with the wireless charging device, such as wireless charging device 300 in FIG. 3A. Sensor module 936 can be an electrical component that houses and operates one or more sensors for performing one or more functions. For instance, sensor module 936 can be a circuit board (e.g., a printed circuit board (PCB)) that has one or more sensors for sensing heart rate and the like. DC shield 934 can be positioned above alignment module 932 to prevent magnetic fields from alignment module 932 from being exposed to other electrical components within portable electronic device 900, such as SIP 916 and secondary receiving element 920. Sensor module 936 can be attached to a surface of bottom hosing 904, as shown in FIG. 11.

2. Assembled Bottom Housing Portion of a Portable Electronic Device Having a Secondary Receiving Element Formed of at Least Two Sub Coils FIG. 11 illustrates a cross-sectional view of an assembled portion 1100 of portable electronic device 900 to better illustrate the construction of portable electronic device 900 when assembled, according to some embodiments of the present disclosure. The cross-section shown in FIG. 11 can be taken along the line shown in FIG. 10C. Assembled portion 1100 illustrated in FIG. 11 does not include top housing portion 902 for ease of discussion.

Figure 11:
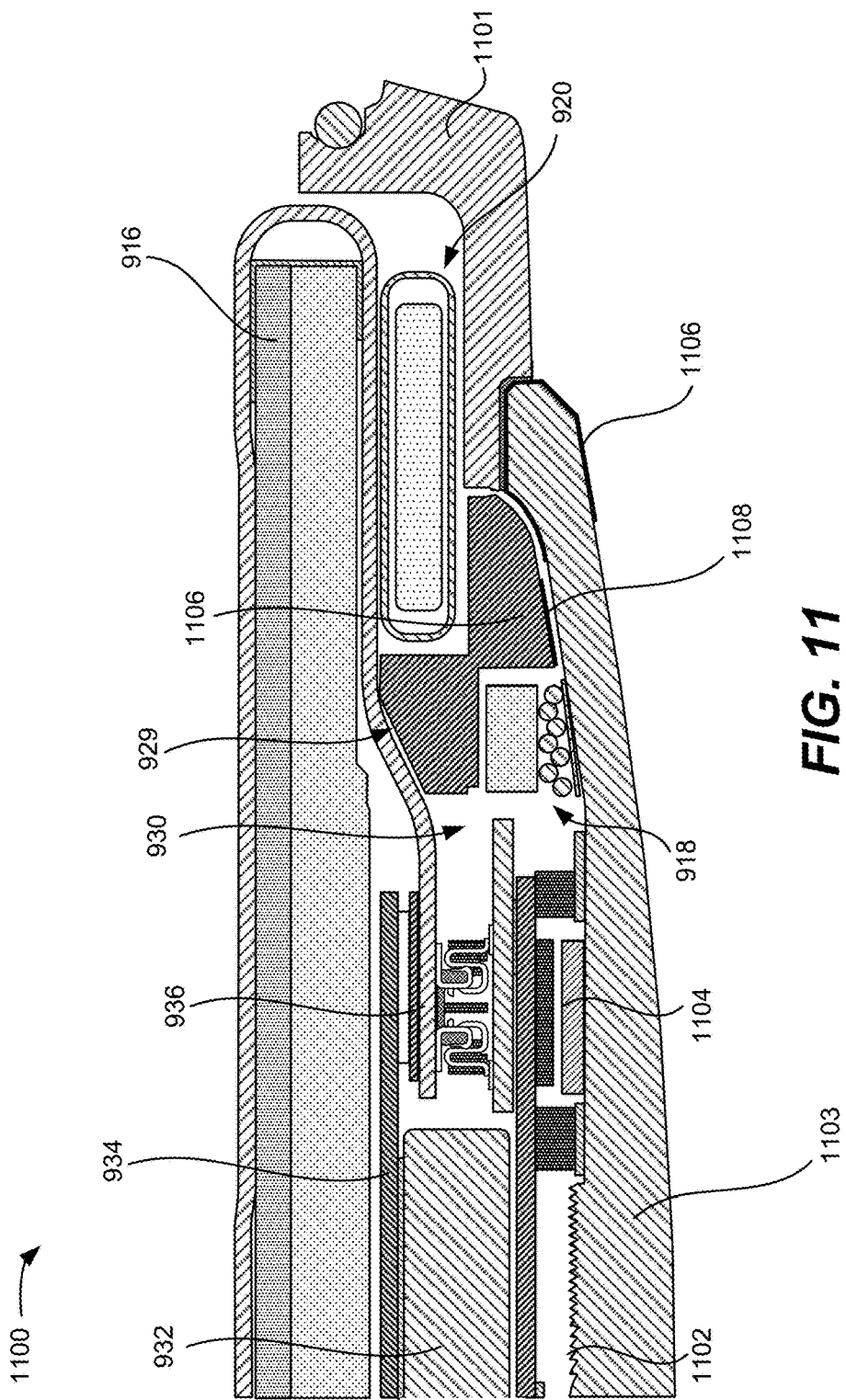
FIG. 11 is a cross-sectional view illustration of an assembled portion of a portable electronic device, according to some embodiments of the present disclosure.

As shown in FIG. 11, sensor module 936 can be mounted on an inner surface of window 1103 of bottom structure body 1101. Sensor module 936 can include a thin heart rate sensor 1102 and one or more photo diodes 1104 for performing sensing functions. Alignment module 932 can be a permanent magnet that is coupled to sensor module 936 and disposed between sensor module 932 and DC shield 934. Second contact 1106 can be positioned on an outer surface of window 1103 and wrap around edges of window 1103 so that it is also positioned on a portion of an inner surface of window 1103. Second contact 1106 can be coupled with sensor module 936 so that sensor module 936 can receive measurements from second contact 1106.

In some embodiments, sensor module 936, alignment module 932, and DC shield 934 are all positioned within opening 930 of antenna 929. As shown in FIG. 11, antenna 929 can be formed of an antenna body 1106 and a conductive layer 1108. Antenna body 1106 can be a support structure upon which conductive layer 1108 can be disposed; and conductive layer 1108 can be a structure that performs the functions of sending and receiving wireless communication through radio waves.

According to some embodiments of the present disclosure, primary receiving element 918 can be disposed within opening 930 and below at least a portion of antenna 929. Furthermore, secondary receiving element 920 can be disposed above at least a portion of antenna 929. Both primary and secondary receiving elements 918 and 920 can be disposed laterally to at least a portion of antenna 929. Primary and secondary receiving elements 918 and 920 can be used to perform wireless charging, as discussed herein with respect to FIGS. 3A and 3B.

B. Primary and Secondary Receiving Elements Constructed as a Single Structure

Although the secondary receiving element can be formed of two sub-coils that are physically separate structures from the primary element as discussed herein with respect to FIGS. 7-9, embodiments are not limited to such configurations. In some embodiments, the secondary receiving element can be formed of a coil wound about a portion of the primary coil such that the structures of the primary receiving element and secondary receiving element are intertwined, as will be discussed herein with respect to FIGS. 12A-12C and 13A-13C.

FIG. 12A is a perspective view illustration of an exemplary wireless charging receiver system 1200 whose primary and secondary receiving elements are formed as a single structure, according to some embodiments of the present disclosure. The primary receiving element can include a primary coil 1202 and a primary ferromagnetic shield 1204, and the secondary receiving element can be formed of a secondary coil 1206 that is wound about a portion of both primary coil 1202 and primary ferromagnetic shield 1204. That is, the axis of secondary coil 1206 can be a curved axis that runs along a length of a turn of wire of primary coil 1202. Details regarding the construction of, and the relationship between, the primary and secondary receiving elements can be better understood with reference to FIGS. 12B-12E.

FIG. 12B is a top-down illustration 1201 of exemplary wireless charging receiver system 1200, and FIG. 12C is a bottom-up illustration 1211 of wireless charging receiver system 1200, according to some embodiments of the present disclosure. Primary coil 1202 can be a stranded coil of wire that has a circular profile centered around a center axis 1208. Ferromagnetic shield 1204 can be configured to overlap a portion of the entire circular profile of primary coil 1202. In some embodiments, ferromagnetic shield 1204 extends between a first radial location 1210 and a second radial location 1212 of primary coil 1202, where the first and second radial locations 1210 and 1212 are different, non-overlapping radial locations. That is, ferromagnetic shield 1204 can be configured to cover only a portion of the entire circumferences of a top surface and two side surfaces of primary coil 1202. Accordingly, ferromagnetic shield 1204 may not cover any surface of a first annular segment 1214 of primary coil 1202. The uncovered area of first annular segment 1214 provides space for the wire of primary coil 1202 to fold over itself so that termination ends 1216 and 1218 can be positioned within an inner diameter of primary coil 1202, as well as space for interconnection structures, such as a flex circuit, to be positioned without significantly affecting the overall z-height. First and second radial locations 1210 and 1212 can form an angle of less than 90 degrees such that ferromagnetic shield 1204 covers an annular section of at least 270 degrees of primary coil 1202. Termination ends 1216 and 1218 are opposite ends of the stranded wire that forms primary coil 1202 where the monolithic structure of the wire physically ends.

In some embodiments, secondary coil 1206 winds around a portion of primary coil 1202 and ferromagnetic shield 1204. For instance, secondary coil 1206 can wrap around a second annular segment 1220 containing overlapping segments of both primary coil 1202 and ferromagnetic shield 1204 such that secondary coil 1206 extends between a third radial location 1222 and a fourth radial location 1224. Winding around ferromagnetic shield 1204 improves the capture of magnetic fields propagating in the horizontal direction because ferromagnetic shield 1204 helps redirect a greater amount of magnetic fields through the inner diameter of secondary coil 1206 than if ferromagnetic shield 1204 was not present. In certain embodiments, first annular segment 1214 and second annular segment 1220 are positioned in a non-overlapping arrangement. That is, secondary coil 1206 does not wind around a portion of first annular segment 1214 where ferromagnetic shield 1204 is not positioned. In some embodiments, first annular segment 1214 and second annular segment 1220 are positioned on opposite halves of receiver system 1200 when drawing a line (not shown) across center axis 1208 of primary coil 1202. As shown in FIGS. 12B and 12C, first and second annular segments 1214 and 1220 are positioned in the top and bottom halves of receiver system 1200, respectively. In some embodiments, termination ends 1219 and 1221 of secondary coil 1206 are positioned within the inner diameter of primary coil 1202. Like termination ends 1216 and 1218, termination ends 1219 and 1221 are opposite ends of the stranded wire that forms secondary coil 1206 where the monolithic structure of the wire physically ends. In certain embodiments, termination ends 1216 and 1218 of primary coil 1202 are positioned adjacent to one another at a location along first annular segment 1214, while termination ends 1219 and 1221 of secondary coil 1206 are positioned on opposite ends of second annular segment 1220.

According to some embodiments of the present disclosure, primary coil 1202 is configured to receive wireless power from magnetic fields propagating in the vertical direction, i.e., into and out of the page, while secondary receiver coil is configured to receive wireless power from magnetic fields propagating in the horizontal direction, i.e., within the plane of the page. Furthermore, primary coil 1202 can be tuned to receive power from time-varying magnetic fields at a first frequency, while secondary coil 1206 can be tuned to receive power from time-varying magnetic fields at a second frequency different from the first frequency. For instance, primary coil 1202 is configured to receive power from magnetic fields at a primary frequency of between 6 to 7 MHz, particularly approximately 6.78 MHz in some embodiments, and secondary coil 1206 is configured to receive power from magnetic fields at a secondary frequency of between 300 to 400 kHz, particularly approximately 326 kHz in some embodiments.

Ferromagnetic shield 1204 can be positioned and configured to improve the efficiency at which primary coil 1202 and secondary coil 1206 receive wireless power. As an example, ferromagnetic shield 1204 can have an outer edge 1226 and an inner edge 1228 when viewed from top-down perspective 1201 and bottom-up perspective 1203 as shown in FIGS. 12B and 12C. Outer edge 1226 can be substantially circular, while inner edge 1228 can include curved and flat edges. For instance, inner edge 1228 can include flat edges 1230 and 1232 that are positioned on opposite halves of receiver system 1200, a curved edge 1229 that extends between flat edges 1230 and 1232, and a curved edge 1231 that extends part of the way between flat edges 1230 and 1232. As shown in FIGS. 12B and 12C, flat edges 1230 and 1232 are positioned at the left and right halves of receiver system 1200. Flat edges 1230 and 1232 can be edge surfaces of respective extended regions 1234 and 1236 of ferromagnetic shield 1204 as shown in FIG. 12C. Extended regions 1234 and 1236 improve the performance of receiver system 1200 by providing shield 1204 more area with which to interact and redirect time-varying magnetic fields generated by a transmitter coil through primary coil 1202 and/or secondary coil 1206. Thus, according to some embodiments, ferromagnetic shield 1204 improves the efficiency of wireless charging for both primary coil 1202 and secondary coil 1206.

As shown in FIG. 12C, extended regions 1234 and 1236 are D-shaped extensions of ferromagnetic shield 1204. Thus, the thickness of a sidewall of ferromagnetic shield 1204 gradually increases from one end to the midpoint of the extended region, and then gradually decreases from the midpoint to the opposite end of the midpoint, as better shown in FIGS. 12D and 12E. FIGS. 12D and 12E are simplified cross-sectional illustrations of ferromagnetic shield 1204 across different planes through extended region 1236, according to some embodiments of the present disclosure. Specifically, FIG. 12D is a simplified cross-sectional illustration of ferromagnetic shield 1204 and primary coil 1202 across the midpoint of extended region 1236, and FIG. 12E is a simplified cross-sectional illustration of ferromagnetic shield 1204 and primary coil 1202 across one end of extended region 1236.

As shown in FIG. 12D, ferromagnetic shield 1204 can be a monolithic structure that includes a back wall 1240 and two sidewalls: an inner sidewall 1242 (i.e., extended region 1236) and an outer sidewall 1244. Both sidewalls 1242 and 1244 can extend away from back wall 1240 toward a transmitter coil (not shown). As further shown in FIG. 12D, primary coil 1202 can include a top surface 1203, a bottom surface 1205, inner side surface 1207, and outer side surface 1209, where both side surfaces 1207 and 1209 are vertically positioned between top surface 1203 and the bottom surface 1205. In some embodiments, ferromagnetic shield 1204 covers three side surfaces of primary coil 1202. That is, back wall 1240 can cover top surface 1203, inner sidewall 1242 can cover inner side surface 1207, and outer sidewall 1244 can cover outer side surface 1207. Accordingly, bottom surface 1205 of primary coil 1202 may not be covered by ferromagnetic shield 1204 and may be oriented away from back wall 1240 toward the transmitter coil to improve the propagation of magnetic fields between primary coil 1202 and the transmitter coil. Inner sidewall 1242 can form inner edge 1228 (including flat edges 1232) of ferromagnetic shield 1204, and outer sidewall 1244 can form outer edge 1226. As discussed herein with respect to FIGS. 12B and 12C, inner edge 1228 can include flat edge 1232 that is formed as part of extended region 1236. Thus, as shown in FIG. 12D, inner sidewall 1242 can have a thickness T2 that is greater than a thickness T1 of outer sidewall 1244, and the left surface of inner sidewall 1242 can be a part of flat edge 1232. With reference to FIG. 12E, as you move toward the end of extended region 1236 (i.e., the beginning of curved edge 1229), thickness T2 of inner sidewall 1242 gradually decreases to thickness T3. In some embodiments, thickness T3 of inner sidewall 1242 at the end of extended region 1236—and throughout the regions outside of extended regions 1236 and 1234 that can include curved edge 1229—can be substantially equal to thickness T1 of outer sidewall 1224. It is to be appreciated that the cross-sections shown in FIGS. 12D and 12E can be present in other points round receiver system 1200, as one skilled in the art can deduce with reference to FIGS. 12B-12E

Figure 13:
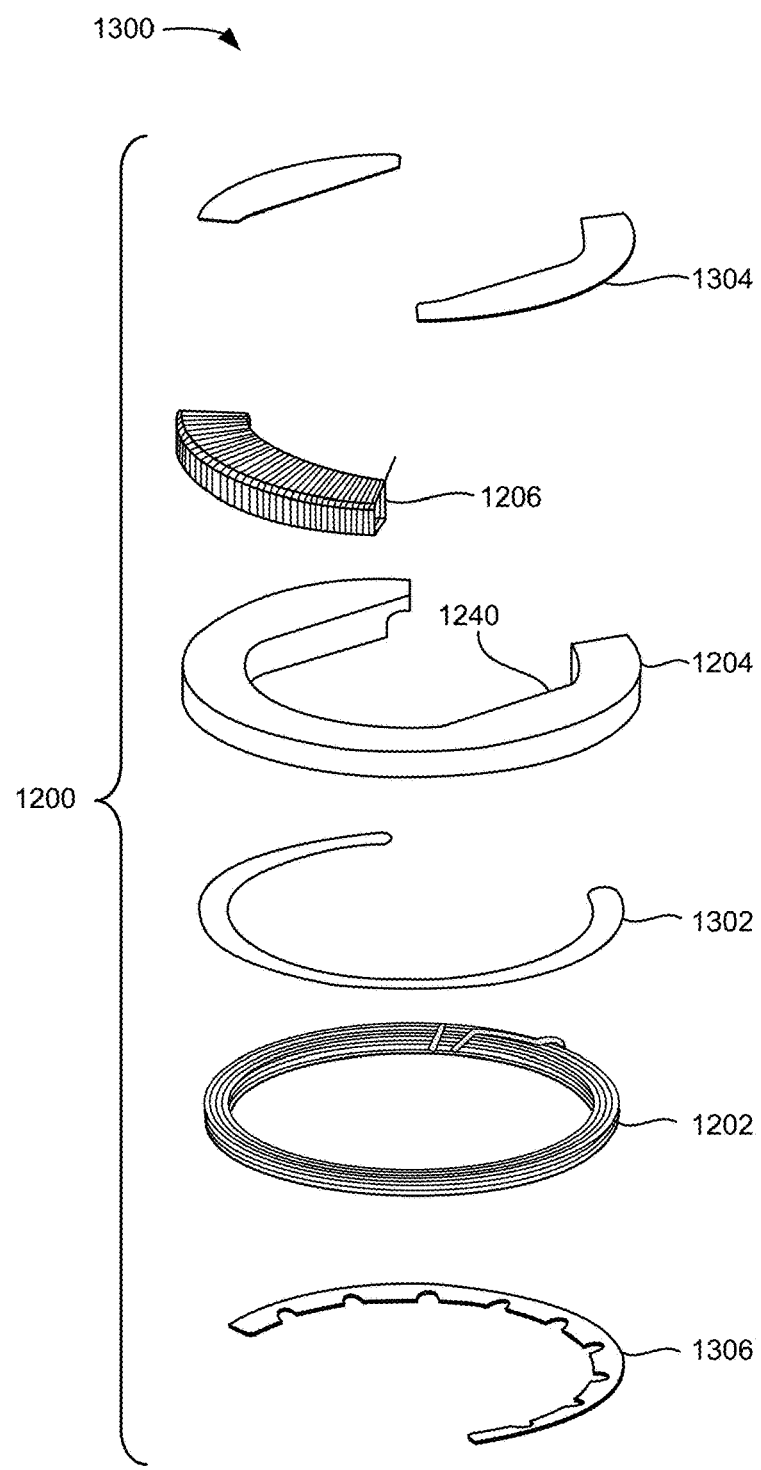
FIG. 13 is an exploded view illustration of the wireless charging receiver system shown in FIGS. 12A-12C, according to some embodiments of the present disclosure.

FIG. 13 is an exploded view illustration 1300 of wireless charging receiver system 1200, according to some embodiments of the present disclosure. Wireless charging receiver system 1200 can include primary coil 1202 attached to ferromagnetic shield 1204. Primary coil 1202 can be a substantially circular coil formed of stranded wire, such as stranded copper wire. An adhesive layer 1302 can be positioned between primary coil 1202 and ferromagnetic shield 1204 to attach primary coil 1202 to ferromagnetic shield 1204. In some embodiments, adhesive layer 1302 is directly positioned between a top surface of primary coil 1202 and a portion, i.e., back wall 1240, of ferromagnetic shield 1204. Adhesive layer 1302 can be substantially circular like the circular profile of primary coil 1202 and only extend along a portion of the top surface of primary coil 1202 where ferromagnetic shield 1204 is positioned. That is, adhesive layer 1302 may be positioned against less than an entire circumference of the top surface of primary coil 1202. Adhesive layer 1302 can be formed of any suitable adhesive material such as hot melt glue.

Secondary coil 1206 can be wound around a portion of ferromagnetic shield 1204 and primary coil 1202. In some embodiments, secondary coil 1206 is formed of a stranded coil of wire, such as stranded copper wire. Portions of back wall 1240 of ferromagnetic shield 1204 that are not covered by secondary coil 1206 can be attached to a pair of ferrite sheets 1304. Ferrite sheets 1304 can be ferromagnetic structures that are formed of a ferromagnetic material different from the ferromagnetic material forming ferromagnetic shield 1204. For instance, ferrite sheets 1304 can be formed of EMFS-C, while ferromagnetic shield 1204 is formed of Mn—Zn. Utilizing ferrite sheets 1304 can increase the magnetic permeability of ferromagnetic structure and thus improve the ability of ferromagnetic shield 1204 to redirect magnetic field through secondary coil 1206. In some embodiments, receiver system 1200 can also include a shim 1306 attached to a bottom surface of primary coil 1202. Shim 1306 can only extend along a portion of a bottom surface of primary coil 1202 where secondary coil 1206 is not positioned. Shim 1306 can provide structural support for primary coil 1202 and thus be formed of any suitable stiff and non-conductive material.

The specific configuration of the structure and position of each layer of receiver system 1200 can be designed to achieve maximum functionality with minimal footprint. In some instances, however, other components within the portable electronic device (e.g., an antenna) can constrain the space available for the receiver system. Thus, the construction of one or more components of wireless charging receiver system 1200 can be modified to have a minimal footprint to enable proper operation of other internal components, as will be discussed further herein with respect to FIGS. 14A-14C.

FIG. 14A is a perspective view illustration of an exemplary wireless charging receiver system 1400 whose primary and secondary receiving elements are formed as a single structure but altered to minimize its size, according to some embodiments of the present disclosure. The primary receiving element can include a primary coil 1402 and a ferromagnetic shield 1404, and the secondary receiving element can be formed of a secondary coil 1406 that is wound about a portion of both primary coil 1402 and ferromagnetic shield 1404. That is, primary coil 1402 can be wound around a primary axis, and secondary coil 1406 can be wound around a secondary axis positioned along a circumference around and centered to the primary axis. In some embodiments, the secondary axis can be a curved axis that runs along a length of a turn of wire of primary coil 1402. When compared to receiver system 1200 in FIGS. 12A-12E, receiver system 1400 can have corresponding components, but some of which may have different construction and dimensions. Details regarding the construction of, and the relationship between, the primary and secondary receiving elements for receiver system 1400, as well as the differences between receiver system 1400 when compared to receiver system 1200, can be better understood with reference to FIGS. 14B-14E.

FIG. 14B is a top-down illustration 1401 of exemplary wireless charging receiver system 1400, and FIG. 14C is a bottom-up illustration 1413 of wireless charging receiver system 1400, according to some embodiments of the present disclosure. Like primary coil 1202, primary coil 1402 can be a stranded coil of wire wound about a center axis 1408 and formed of a conductive material, such as copper. However, unlike primary coil 1202 which has a circular profile, primary coil 1402 can have an oblong profile. For instance, as shown in FIG. 14C, primary coil 1402 can be a coil of wire whose windings form a profile that includes two straight segments 1403 and 1405 and two curved segments 1407 and 1409 positioned between straight segments 1403 and 1405. Configuring primary coil 1402 to have an oblong profile provides more space beside coil 1402 for another component, such as an antenna, to be positioned as will be discussed further herein.

Ferromagnetic shield 1404 can be configured to overlap a portion of the entire oblong profile of primary coil 1402. Ferromagnetic shield 1404 can be configured to extend between a first radial location 1410 and a second radial location 1412 of primary coil 1402, where the first and second radial locations 1410 and 1412 are non-overlapping. That is, ferromagnetic shield 1404 can be configured to cover only a portion of the entire circumference of a top surface and an inner side surface of primary coil 1402. Accordingly, a first annular segment 1414 of primary coil 1402 may not be covered by ferromagnetic shield 1404. The uncovered area of first annular segment 1414 provides space for the wire of primary coil 1402 to fold over itself so that termination ends 1416 and 1418 can be positioned within an inner diameter of primary coil 1402, as well as space for interconnection structures, such as a flex circuit, to be positioned without significantly affecting the overall z-height. First and second radial locations 1410 and 1412 can form an angle of less than 90 degrees such that ferromagnetic shield 1404 covers an annular region of at least 270 degrees of primary coil 1402. In some embodiments, ferromagnetic shield 1404 can include a flat outer bottom edge 1411 positioned at a bottom of primary coil 1402 between straight segments 1403 and 1405. Flat outer bottom edge 1411 may not have a curved edge that follows the profile of primary coil 1402, but may instead straighten out and align with the bottom edge of primary coil 1402 such that the outer surface of ferromagnetic shield 1404 at the center of flat outer bottom edge 1411 is substantially coplanar with the bottommost edge of primary coil 1402, thereby reducing the amount of overhang of ferromagnetic shield 1404 with respect to primary coil 1402.

Secondary coil 1406 can be similar in construction and function as secondary coil 1206. That is, secondary coil 1406 can wind around a second annular segment 1420 containing overlapping segments of both primary coil 1402 and ferromagnetic shield 1404 such that secondary coil 1406 extends between a third radial location 1422 and a fourth radial location 1424. Additionally, in some embodiments, first annular segment 1414 and second annular segment 1420 can be positioned on opposite halves (e.g., top and bottom halves) of receiver system 1400, and secondary coil 1406 can have termination ends 1419 and 1421 that are positioned within the inner diameter of primary coil 1402. By winding around ferromagnetic shield 1404, secondary coil 1406 can have improved power transfer efficiency as shield 1404 can help redirect and increase an amount of flux through the inner diameter of secondary coil 1406.

However, unlike secondary coil 1206 for receiver system 1200 in FIG. 12, secondary coil 1406 for receiver system 1400 can also include a flat region that overlaps and follows flat outer bottom edge 1411 of ferromagnetic shield 1404. By reducing the amount of overhang between ferromagnetic shield 1404 and primary coil 1402 and winding secondary coil 1406 around flat outer bottom edge 1411, more vacant space can be provided between the bottom of secondary coil 1406 and another component, such as an antenna, to provide more electrical isolation between secondary coil 1406 and the antenna to minimize electrical interference with the operation of the antenna as will be discussed further herein.

Ferromagnetic shield 1404 can be positioned and configured to improve the efficiency at which primary coil 1402 and secondary coil 1406 receive wireless power, and can also be constructed to maximize space for other components of the portable electronic device. As an example, ferromagnetic shield 1404 can have an outer edge 1426 and an inner edge 1428 when viewed from top-down perspective 1401 and bottom-up perspective 1403 as shown in FIGS. 14B and 14C. Unlike outer and inner edges 1226 and 1228 of ferromagnetic shield 1204, both outer edge 1426 and inner edge 1428 of ferromagnetic shield 1404 can have substantially oblong profiles. For instance, outer edge 1426 can include flat outer side edges 1450 and 1452 that are positioned on opposite halves of receiver system 1400, flat outer bottom edge 1411 positioned on a bottom region of receiver system 1400, curved edges 1456 and 1458 that extend between flat outer bottom edge 1411 and both flat outer side edges 1450 and 1452, and a curved edge 1460 that extends part of the way between flat outer side edges 1450 and 1452. And, inner edge 1428 can include flat edges 1430 and 1432 that are positioned on opposite halves of receiver system 1400, a curved edge 1429 that extends between flat edges 1430 and 1432, and a curved edge 1431 that extends part of the way between flat edges 1430 and 1432. By flattening outer surfaces of ferromagnetic shield 1404, more space can be provided for other electrical components and greater electrical isolation can be provided between the other electrical components and secondary coil 1406.

In some embodiments, flat outer side edges 1450 and 1452 can have an edge that is coplanar with respective edges of straight segments 1403 and 1405. For instance, flat outer side edge 1450 can be coplanar with the outermost left edge of straight segment 1403 of primary coil 1402, and flat edge 1452 can be coplanar with the outermost right edge of straight segment 1405 of primary coil 1402. By arranging flat outer side edges 1450 and 1452 to be coplanar with respective edges of straight segments 1403 and 1405, overhang of ferromagnetic shield 1404 with respect to primary coil 1402 can be minimized, thereby providing more space for other components, e.g., an antenna, to be positioned. Additionally, flat outer bottom edge 1411 can be coplanar with a bottommost edge of primary coil 1402. By arranging flat outer bottom edge 1411 to be coplanar with bottommost edge of primary coil 1402, overhang of ferromagnetic shield 1404 with respect to primary coil 1402 can be minimized, thereby providing more electrical isolation between secondary coil 1406 and other components e.g., an antenna, within the portable electronic device. A better view of such relationships between ferromagnetic shield 1404 and primary coil 1402 can be seen in FIGS. 14D and 14E.

FIGS. 14D and 14E are simplified cross-sectional illustrations of ferromagnetic shield 1404 across different planes through straight segment 1405, according to some embodiments of the present disclosure. Specifically, FIG. 14D is a simplified cross-sectional illustration of ferromagnetic shield 1404 and primary coil 1402 across the midpoint of straight segment 1405, and FIG. 14E is a simplified cross-sectional illustration of ferromagnetic shield 1404 and primary coil 1402 across one end of straight segment 1405.

As shown in FIG. 14D, ferromagnetic shield 1404 can be a monolithic structure that includes a back wall 1440 and an inner sidewall 1442 for covering two side surfaces of primary coil 1402. Specifically, back wall 1440 can cover a back surface 1441 of primary coil 1402 and inner sidewall 1442 can cover an inner surface 1443 of primary coil 1402. Two sides of primary coil 1402 may not be covered by ferromagnetic shield 1404, but inner sidewall 1442 may extend away from back wall 1440 toward a transmitter coil (not shown) to improve the propagation of magnetic fields between primary coil 1402 and the transmitter coil. As discussed herein with respect to FIGS. 14B and 14C, outer edge 1426 can include flat edge 1452 that is coplanar with the rightmost edge of straight segment 1405 of primary coil 1402. Thus, as shown in FIG. 14D, flat edge 1452 can be coplanar with the rightmost edge 1462 of straight segment 1405 of primary coil 1402. With reference to FIG. 14E, as you move toward the end of straight segment 1405 (i.e., the beginning of curved edge 1458), curved edge 1458 gradually extends away from edge 1464 of primary coil 1402, thereby creating an overhang 1466. It is to be appreciated that the cross-sections shown in FIGS. 14D and 14E can be present in other points round receiver system 1400, as one skilled in the art can deduce with reference to FIGS. 14B-14E. Flat edges 1450, 1452, and 1411 can all be a part of back wall 1440.

Figure 15:
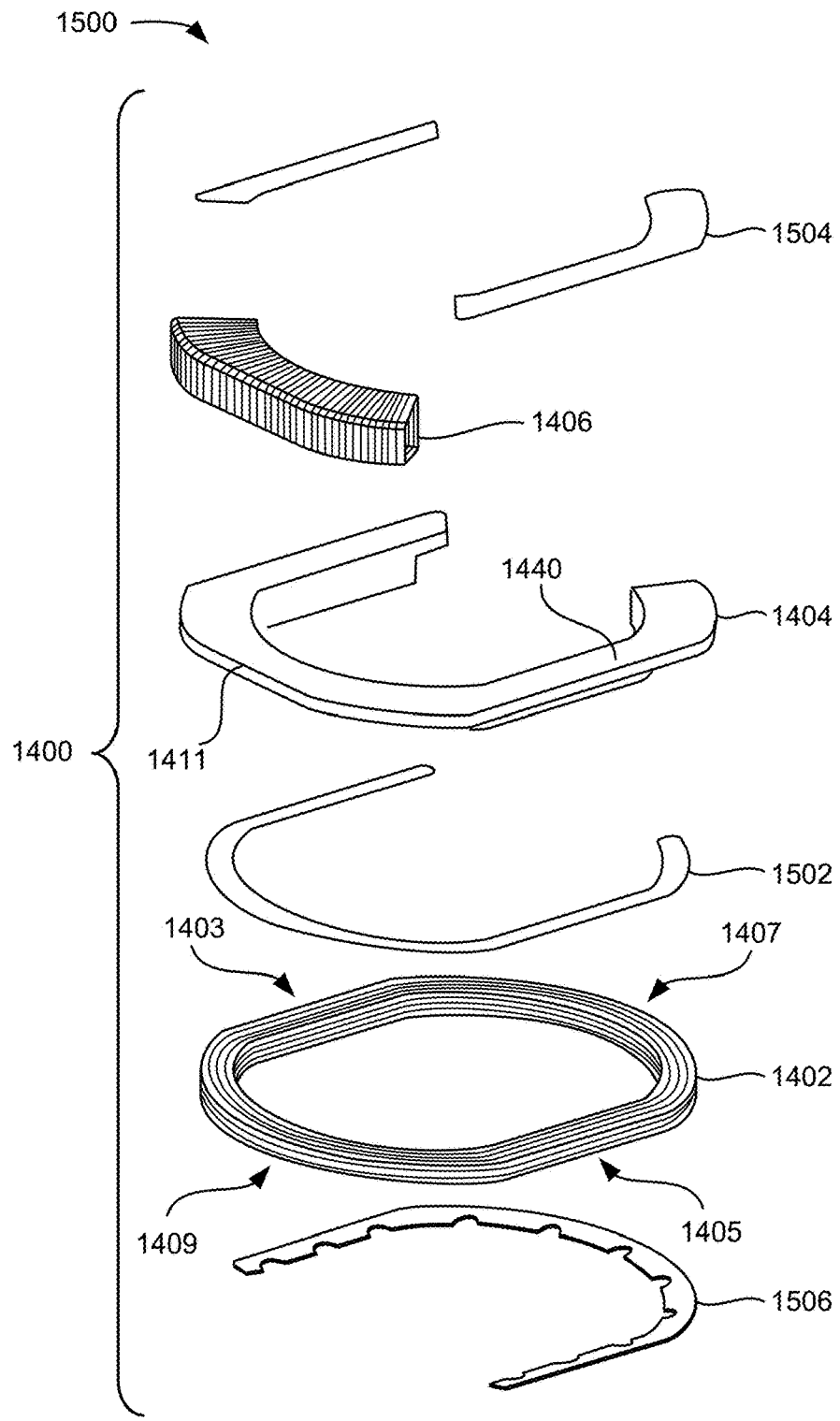
FIG. 15 is an exploded view illustration of the wireless charging receiver system shown in FIGS. 14A-14C, according to some embodiments of the present disclosure.

FIG. 15 is an exploded view illustration 1500 of wireless charging receiver system 1400, according to some embodiments of the present disclosure. Wireless charging receiver system 1400 can include primary coil 1402 attached to ferromagnetic shield 1404. Primary coil 1402 can be a substantially oblong coil formed of stranded wire, such as stranded copper wire, and include straight segments 1403 and 1405 and curved segments 1407 and 1409 positioned between straight segments 1403 and 1405. An adhesive layer 1502 can be positioned between primary coil 1402 and ferromagnetic shield 1404 to attach primary coil 1402 to ferromagnetic shield 1404. In some embodiments, adhesive layer 1502 is directly positioned between a top surface of primary coil 1402 and a portion, i.e., back wall 1440, of ferromagnetic shield 1404. Adhesive layer 1502 can be substantially oblong in shape like primary coil 1402 and only extend along a portion of the top surface of primary coil 1402 where ferromagnetic shield 1404 is positioned. That is, adhesive layer 1502 may be positioned against less than an entire circumference of the top surface of primary coil 1402. Adhesive layer 1502 can be formed of any suitable adhesive material such as hot melt glue.

Secondary coil 1406 can be wound around a portion of ferromagnetic shield 1404 and primary coil 1402. In some embodiments, secondary coil 1406 is formed of a stranded coil of wire, such as stranded copper wire. Portions of back wall 1440 of ferromagnetic shield 1404 that are not covered by secondary coil 1406 can be attached to a pair of ferrite sheets 1504, which can be ferromagnetic structures that are formed of a ferromagnetic material different from the ferromagnetic material forming ferromagnetic shield 1404. For instance, ferrite sheets 1504 can be formed of EMFS-C, while ferromagnetic shield 1404 is formed of Mn—Zn. Utilizing ferrite sheets 1504 can increase the magnetic permeability of ferromagnetic structure and thus improve the ability of ferromagnetic shield 1404 to redirect magnetic field through secondary coil 1406. In some embodiments, receiver system 1400 can also include a shim 1506 attached to a bottom surface of primary coil 1402. Shim 1506 can only extend along a portion of a bottom surface of primary coil 1402 where secondary coil 1406 is not positioned. Shim 1506 can provide structural support for primary coil 1402 and thus be formed of any suitable stiff and non-conductive material.

1. Construction of a Portable Electronic Device Having Secondary Receiving Element Formed of a Coil Wound about a Portion of the Primary Coil As mentioned herein, the size and shape of primary and secondary receiver elements can affect the amount of available space for other electrical components in the portable electronic device, while also enabling the portable device to achieve a compact size and high functionality. As can be appreciated by disclosures herein, the size and shape of the receiver elements can be determined by balancing the trade-off between performance of the receiver elements and the performance of other electrical components in the portable electronic device.

a) Top Housing Portion

Figure 16:
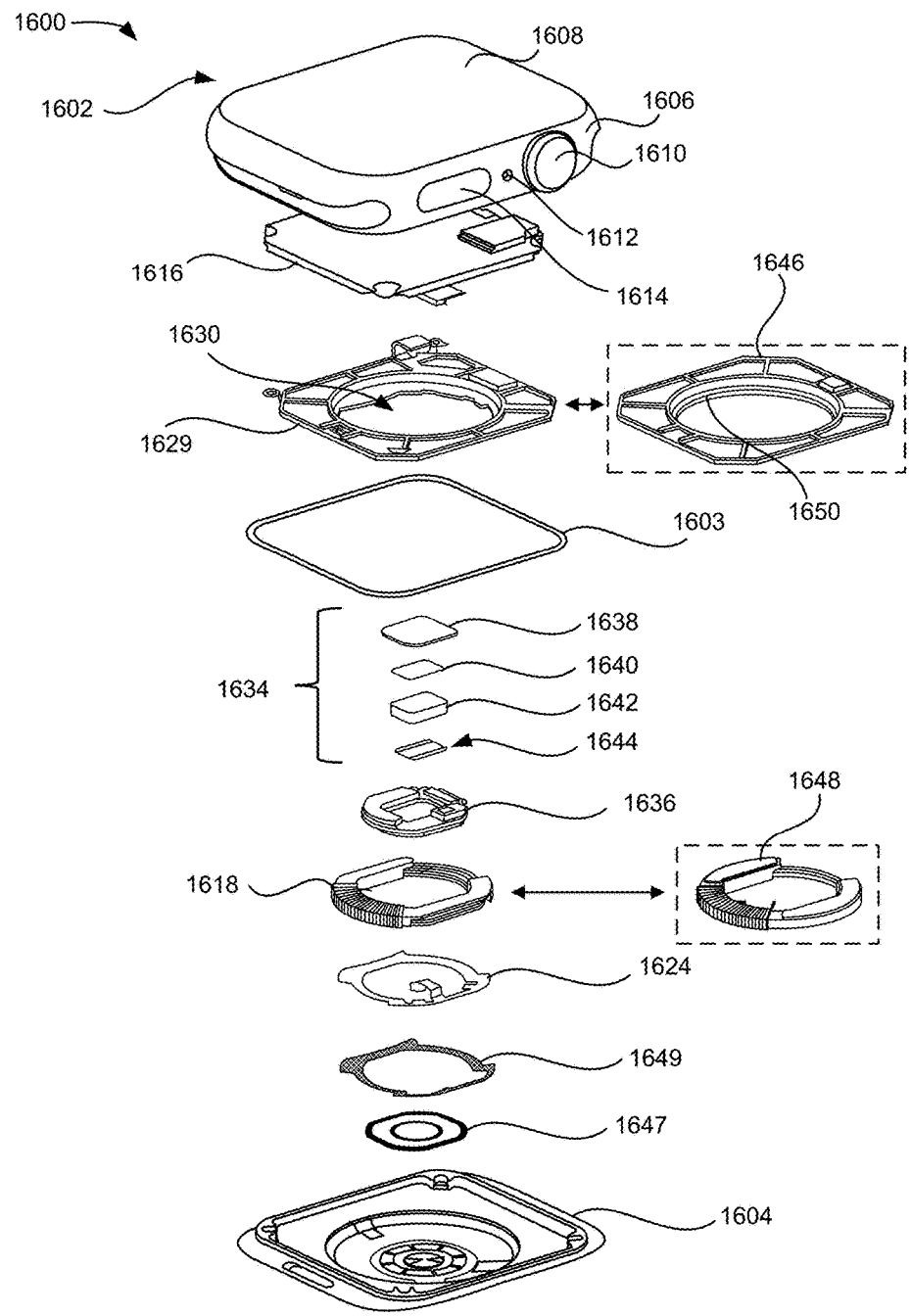
FIG. 16 is an exploded view illustration of an exemplary portable electronic device, according to some embodiments of the present disclosure.

FIG. 16 illustrates an exploded view of an exemplary portable electronic device 1600, according to some embodiments of the present disclosure. Portable electronic device 1600 can include a top housing portion 1602 and a bottom housing portion 1604 that can mate to define an interior cavity. A sealing component 1603 can be positioned at the interface between top housing portion 1602 and bottom housing portion 1604 to seal the interior cavity from the external environment. Sealing component 1603 can be any suitable component that can hermetically seal an interface between two structures such as an O-ring formed of silicone. Top housing portion 1602 can include a device chassis 1606 and a transparent panel 1608. Transparent panel 1608 is a protective, optically transparent structure for a display so that a user can view the display through transparent panel 1608 while transparent panel 1608 protects the display from damage. Top housing portion 1602 can include one or more user interface components, such as a dial 1610, microphone 1612, power button 1614, and any other suitable user interface components. The compact size and unique arrangement of the internal components of portable electronic device 1600 can enable microphone 1612 to be positioned on the same side of device chassis 1606 as dial 1610.

In some embodiments, dial 1610 can be a touch sensitive dial that can act as a contact for performing EKG sensing. Dial 1610 can include various components that, when coupled together, form a conductive pathway from an outer surface of dial 1610 to inner touch components, which is discussed further herein with respect to FIGS. 35 and 36. Portable electronic device 1600 can further include a system in package (SIP) 1616 that is housed within the interior cavity. SIP 1616 can be a number of integrated circuits (ICs) enclosed in a single module that can operate to perform several functions of portable electronic device 1600. Each IC in SIP 1616 can perform one or more different functions, such as performing heart rate monitoring, operating a touch screen display, outputting sound through one or more speakers, processing sound received by microphone 1612, managing wireless power transfer, and the like.

Portable electronic device 1600 can also include an alignment module 1632 and a sensor module 1636. Sensor module 1636 can be an electrical component that houses and operates one or more sensors for performing one or more functions. For instance, sensor module 1636 can be a circuit board (e.g., a printed circuit board (PCB)) that has one or more sensors for sensing heart rate and the like. Sensor module 1636 can be attached to a surface of bottom housing portion 1604 via adhesive layer 1647, which can be formed of PSA.

b) Alignment Module

Alignment module 1632 can be disposed between SIP 1616 and sensor module 1636 as shown in FIG. 16. Alignment module 1632 can include a permanent magnet 1642 and a DC shield 1638 positioned above magnet 1642 that are coupled together via a magnet adhesive 1640. Magnet 1642 can be designed to attract another alignment magnet in a wireless charging device for aligning with the wireless charging device, such as wireless charging device 300 in FIG. 3A. DC shield 1638 can be positioned above alignment module 1632 to prevent magnetic fields generated by alignment module 1632 from being exposed to other electrical components within portable electronic device 1600, such as SIP 1616. Alignment module 1632 can also include a module adhesive layer 1644 for coupling alignment module 1632 to sensor module 1636. In some embodiments, module adhesive layer 1644 can be formed of multiple parts, as better illustrated in FIG. 17.

Figure 17:
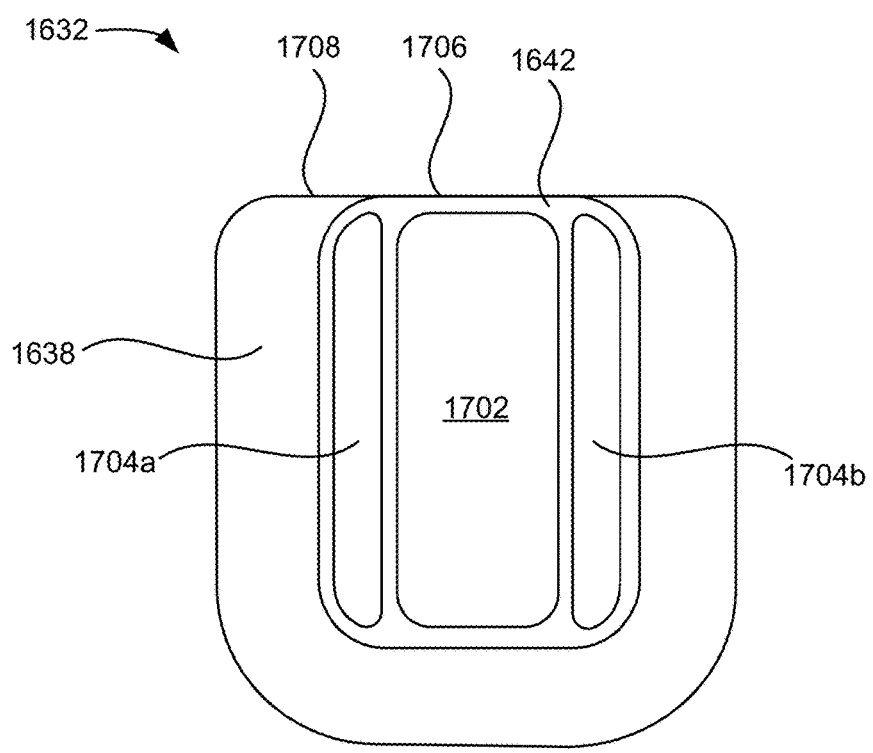
FIG. 17 is a bottom-up view illustration of an alignment module, according to some embodiments of the present disclosure.

FIG. 17 is a bottom-up view illustration of alignment module 1632, according to some embodiments of the present disclosure. As shown in FIG. 17, module adhesive layer 1644 can be formed of a first adhesive 1702 laterally positioned between second adhesive 1704a and third adhesive 1704b. First, second, and third adhesives 1702, 1704a, and 1704b can all be adhered to and extend across an entire length of a bottom surface of permanent magnet 1642. First adhesive 1702 can be formed of a material different from the material used to form second and third adhesives 1704a-b. For instance, first adhesive 1702 can be formed of hot melt glue, while second and third adhesives 1704a-b are formed of PSA.

Figure 18:
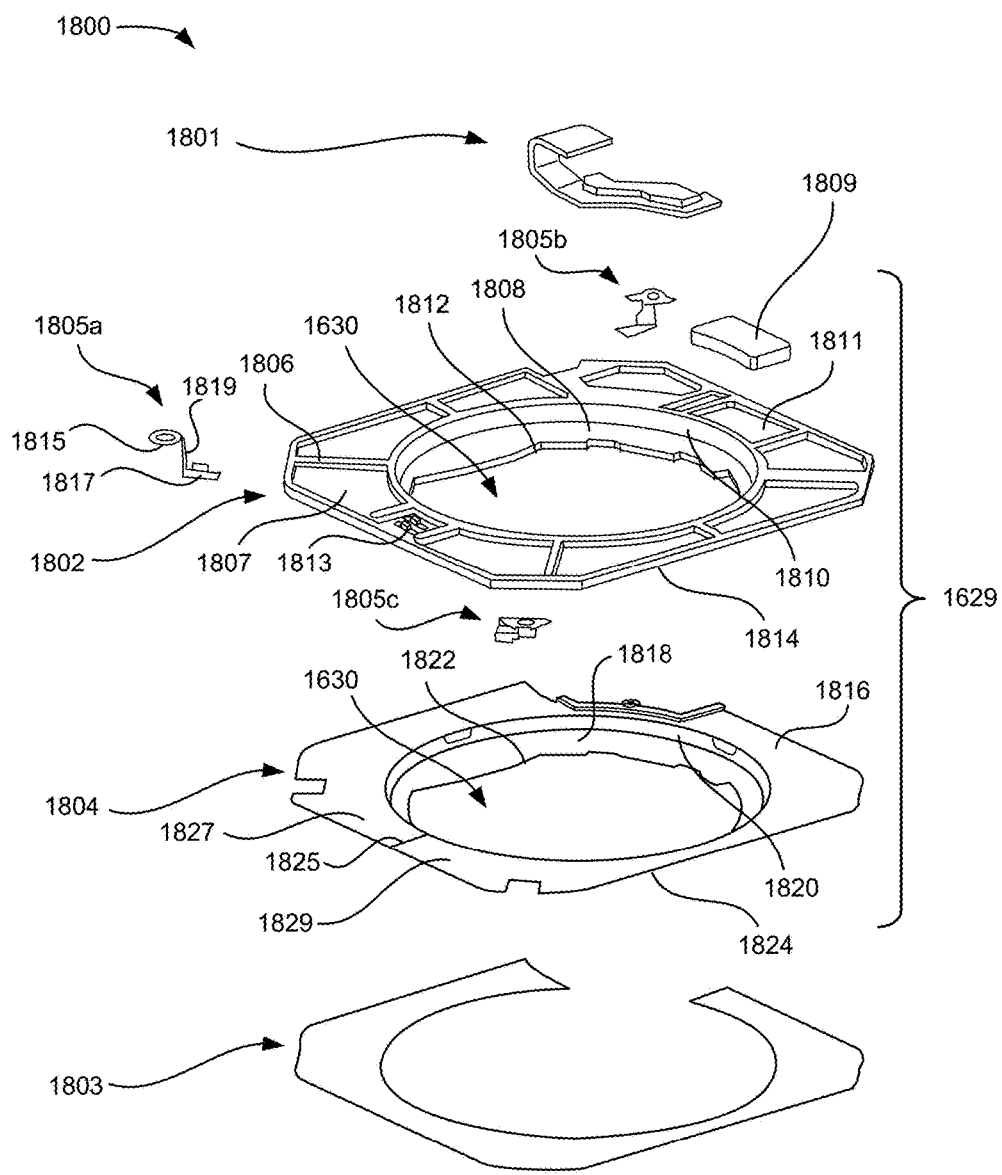
FIG. 18 is an exploded view diagram of an antenna system, according to some embodiments of the present disclosure.

As further shown in FIG. 17, a top edge 1706 of permanent magnet 1642 can be coplanar with a top edge 1708 of DC shield 1638, while other edges of DC shield 1638 overhang from corresponding edges of magnet 1642. Having both top edges 1706 and 1708 be coplanar can enable more space to be provided for other components on sensor module 1636, such as a connector for coupling with a flex circuit as shown in FIG. 18, thereby enabling more components to be assembled within the portable electronic device and assist with decreasing its overall size.

c) Wireless Charging Receiver System

With reference back to FIG. 16, portable electronic device 1600 can include a wireless charging receiver system 1618 formed of a single structure having a primary receiving element and a secondary receiving element, according to some embodiments of the present disclosure. The primary receiving element can include a primary coil and a ferromagnetic structure, and the secondary receiving element can include a secondary coil wound around a portion of the primary receiving element. The specific configuration of receiver system 1618 is better discussed herein with respect to FIGS. 14A-14E and 15. Portable electronic device 1600 can also include an electromagnetic shield 1624 disposed between receiver system 1618 and bottom housing portion 1604. Electromagnetic shield 1624 can intercept electric fields generated during wireless power transfer and discharge the accumulated voltage from the electric fields to ground. Electromagnetic shield 1624 and receiver system 1618 can be attached to bottom housing portion 1604 by an adhesive layer 1649, which can be formed of any suitable adhesive such as PSA. In some embodiments, wireless charging receiver system 1618 can receive wireless power from time-varying magnetic fields generated from one or more transmitter coils in a wireless charging device, e.g., device 300 or 310 in FIGS. 3A and 3B. Specifically, time-varying magnetic flux generated by transmitter coil 302 in FIG. 3A can propagate through bottom housing portion 1604 at a first frequency and interact with the primary coil, e.g., primary coil 1202 in FIG. 12 or primary coil 1402 in FIG. 14, of wireless charging receiver system 1618 which can be specifically tuned to operate at the first frequency and receive fields propagating in the vertical direction. Furthermore, time-varying magnetic flux generated by transmitter coil 312-1 in FIG. 3B can propagate through bottom housing portion 1604 at a second frequency and interact with the secondary coil, e.g., secondary coil 1206 in FIG. 12 or secondary coil 1406 in FIG. 14, of wireless charging receiver system 1618 which can be specifically tuned to operate at the second frequency and receive fields propagating in the horizontal direction.

d) Antenna

Portable electronic device 1600 can be configured to perform wireless communication through radio waves, e.g., LTE, GSM, CDMA, and the like, while other variations of portable electronic device 1600 can be configured to not have this functionality. To enable wireless communication functionality, portable electronic device 1600 can include an antenna 1629 within the interior cavity and below SIP 1616, as shown in FIG. 16. Antenna 1629 can include an opening 1630 within which one or more other electronic components of portable electronic device 1600 can be positioned. For instance, wireless charging receiver system 1618 and alignment module 1634 can be disposed within opening 1630. Antenna 1629 can be a structure configured to receive and/or send data through radio waves, as discussed further herein with respect to FIG. 18.

FIG. 18 is an exploded view diagram of an antenna system 1800 including antenna 1629, according to some embodiments of the present disclosure. In addition to antenna 1629, antenna system 1800 can include an antenna interconnection structure 1801 for coupling antenna 1629 to a controller, such as a processor in communication system 108 in FIG. 1, and an adhesive layer 1803 for attaching antenna 1629 to bottom housing portion 1604. Interconnection structure 1801 can be formed of any suitable flexible interconnection structure such as a flexible printed PCB, and adhesive layer 1803 can be formed of any suitable adhesive material such as PSA.

As further shown in FIG. 18, antenna 1629 can be formed of an antenna element 1802 and a conductive antenna body 1804 attached to a bottom surface of antenna element 1802. Antenna element 1802 can be a non-conductive structure that provides structural support for conductive antenna body 1804, which can be formed of a thin conductive material that can transmit and receive radio waves. Antenna element 1802 can be formed of any suitable non-conductive material such as glass-filled LCP resin, and conductive antenna body 1804 can be formed of any suitable conductive material such as copper. In some embodiments, conductive antenna body 1804 can be grounded via one or more grounding brackets 1805a-c. Details of the construction and function of grounding brackets 1804a-c is discussed further herein with respect to FIGS. 19A-19D. Antenna element 1802 can also include a slit (not shown) at a bottom region of antenna element 1802 and one or more capacitors 1813 that bridge the gap created by the slit, as will be discussed further herein.

As shown in FIG. 18, antenna element 1802 can include a top level 1806, a bottom level 1808, and a step region 1810 between top and bottom levels 1806 and 1808. Top and bottom levels 1806 and 1808 can be substantially planar structures that are positioned in different parallel but non-intersecting planes, and step region 1810 can be a vertical bridging portion between top and bottom levels 1806 and 1808. Top level 1806, bottom level 1808, and step region 1810 can together form a monolithic structure that forms antenna element 1802. In some embodiments, top level 1806 can include a plurality of recessed areas 1807 within which one or more foam pads can be positioned. For instance, foam pad 1809 can be positioned within a recessed area 1811 near the top edge of antenna element 1802. Foam pad 1809 can press up against a flexible PCB (not shown) that couples with electrical components (not shown) within opening 1630.

In some embodiments, step region 1810 creates open space within which at least some parts of other electrical components of the portable electronic device, such as wireless charging receiver system 1618, alignment module 1634, and sensor module 1636 in FIG. 16, can be positioned to minimize z-height. When positioned within the open space, wireless charging receiver system 1618 and alignment module 1634 can be substantially coplanar with antenna 1629. In certain embodiments, an inner edge 1812 of antenna element 1802 can be a part of bottom level 1808 that conforms to the outer profile of receiver system 1618. Accordingly, inner edge 1812 can have an oblong profile that conforms to an outer edge of wireless charging receiver system 1618. In some embodiments, an outer edge 1814 of antenna element 1802 can be a part of top level 1806 that conforms to the inner profile of bottom housing portion 1604. Accordingly, outer edge 1814 can have a substantially rectangular profile with beveled corners, as shown in FIG. 18. While inner edge 1812 has an oblong profile and outer edge 1814 has a rectangular profile with beveled edges, step region 1810 can have a different profile than both inner edge 1812 and outer edge 1814 such as a substantially circular profile for providing separation between antenna 1629 and any electrical components positioned within opening 1630.

As shown in FIG. 18, conductive antenna body 1804 can conform to a bottom surface of antenna element 1802 and thus also include a top level 1816, bottom level 1818, step region 1820, inner edge 1822, and outer edge 1824 that are substantially similar in structure to corresponding parts of antenna element 1802. That is, top level 1816 can be positioned below top level 1806, bottom level 1818 can be positioned below bottom level 1808, step region 1820 can be positioned beside step region 1810, inner edge 1822 can have an oblong profile that conforms to an outer edge of wireless charging receiver system 1618, and outer edge 1824 can have a substantially rectangular profile with beveled corners.

In some embodiments, conductive antenna body 1804 can include a slit 1825 that cuts through a section of conductive antenna body 1804 to separate the section into two parts: a first part 1827 and a second part 1829. Even though the section is divided into first and second parts 1827 and 1829, conductive antenna body 1804 can still be a single monolithic structure that has a discontinuous oblong structure, instead of a continuous oblong structure in instances where slit 1825 is not present. In some embodiments, capacitors 1813 disposed on top level 1806 of antenna element 1802 can extend through top level 1806 and bridge across slit 1825 to electrically couple the two parts of conductive antenna body 1704 together. The capacitance of capacitors 1813 can be configured to enable conductive antenna body 1804 to appear electrically as a single continuous body at the antenna's operating frequency but appear electrically disconnected at the receiver system's operating frequency, which can be different from the antenna's operating frequency. In such embodiments, the capacitors can be configured to electrically couple first and second parts 1827 and 1829 together when conductive antenna body 1704 is exposed to electrical signals at a first frequency and electrically disconnect first and second parts 1827 and 1829 from one another when conductive antenna body 1704 is exposed to time-varying magnetic fields at a second frequency different from the first frequency to minimize the generation of eddy currents in conductive antenna body 1704. Without slit 1825, large eddy currents can be generated in conductive antenna body 1804 and create heat that can negatively impact the power transfer efficiency of receiver system 1618. That way, both antenna 1629 and receiver system 1618 can coexist without significantly affecting each other's performance.

It is to be appreciated that larger coils and ferromagnetic structures of a receiver system can improve the efficiency at which the portable electronic device receives charge, as mentioned herein with respect to FIG. 12A-12E. However, increasing the size of these structures reduces the amount of space for the antenna, thereby negatively affecting the antenna's performance. Thus, a conflict of interest with respect to component size can exist between antenna 1629 and receiver system 1618 due to their close proximity with one another. Accordingly, the structure of the receiver system and the antenna can be optimized to achieve acceptable levels of both antenna operation and charging efficiency. Details of this relationship is discussed further herein with respect to FIG. 19.

Figure 19:
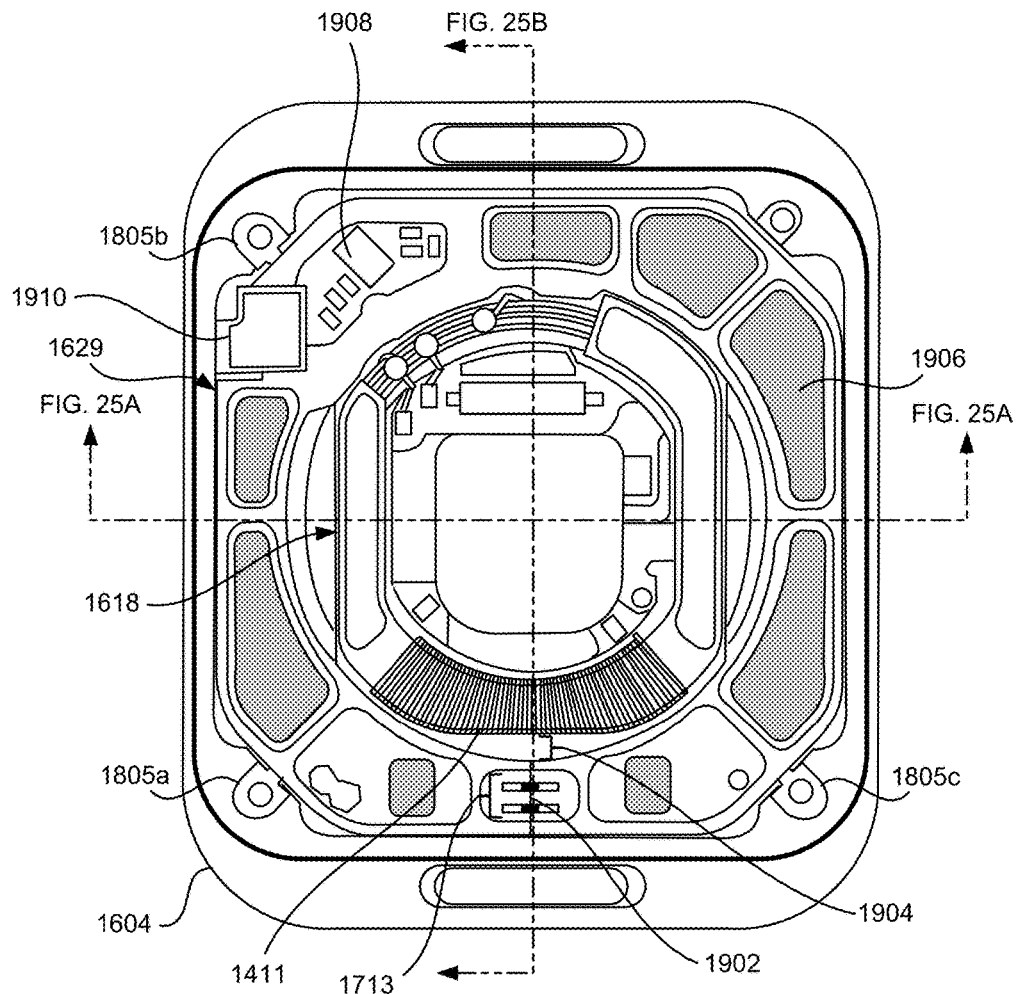
FIG. 19 is a top-down illustration of a partially assembled portion of portable electronic device, according to some embodiments of the present disclosure.

FIG. 19 is a top-down illustration of a partially assembled portion of portable electronic device 1600, according to some embodiments of the present disclosure. Specifically, FIG. 19 shows a portion of device 1600 that includes receiver system 1618, antenna 1629, and bottom housing portion 1604. Receiver system 1618 is shown positioned within the opening (which is not shown because it is occupied by receiver system 1618) of antenna 1629, both of which are assembled into bottom housing portion 1604. The surface area of antenna 1629 (and thus conductive antenna body 1804) can be tailored to achieve a certain degree of antenna performance. For instance, larger surface areas can improve the signal receiving and transmitting performance of antenna 1629. As such, receiver system 1618 can include flat outer side edges, e.g., flat outer side edges 1450 and 1452 discussed herein with respect to FIG. 14, so that antenna 1629 can have more surface area. The structure of conductive antenna body 1804 can be configured to maximize the use of space provided between receiver system 1618 and bottom housing portion 1604 by fitting in available space between them.

In some embodiments, the antenna element, e.g., antenna element 1802, of antenna 1629 can include a plurality of recessed areas, e.g., recessed areas 1807. These recessed areas can be regions where components can be positioned. For instance, a plurality of foam structures 1906 can be positioned within the recessed areas to protect antenna 1629 from physical damage. Furthermore, one or more electrical components 1908 can be positioned with a recessed area. Electrical components 1908 can be configured to operate antenna 1629, and be coupled to a communication system via interconnection 1910, which can be a flex circuit. Utilizing the space provided by the recessed areas maximizes the use of the limited space within the portable electronic device without having to increase the size of the portable electronic device.

As briefly discussed herein, antenna 1629 can have a slit 1902 that extends from the inner diameter to the outer diameter of antenna 1629 and through conductive antenna body 1804 such that the bottom section of conductive antenna body 1804 is divided in half lengthwise. Secondary coil of receiver system 1618 can overlap at least a portion of slit 1902. Separating the continuity of antenna 1629 can minimize eddy current generation when receiver system 1618 (more particularly the secondary coil of receiver system 161) is operating, thereby minimizing excessive heat generation which can negatively affect the performance of receiver system 1618. However, separating the continuity of antenna 1629 can hinder the performance of antenna 1629. Thus, in some embodiments, one or more capacitors 1813 can be implemented in antenna 1629 to electrically bridge the two halves of the bottom section of antenna 1629. The capacitance of capacitors 1813 can be tailored such that antenna 1629 appears electrically as a single continuous body at the operating frequency of antenna 1629, but appear separated at the operating frequency of receiver system 1618, which can be different from the operating frequency of antenna 1629. That way, both antenna 1629 and receiver system 1618 can coexist without significantly affecting each other's performance.

Evident in FIG. 19, the bottom edge of wireless charging receiver system 1618 can be separated from the step region of antenna 1629 by a distance 1904. Because both the secondary coil of receiver system 1618 and the conductive antenna body of antenna 1629 are formed of a conductive material, the two components can interfere with each other's performance the closer they are to one another. Thus, larger distances 1904 can improve the electrical isolation between the two components, and thus help ensure that both components work properly. In some embodiments, the flat bottom edge of receiver system 1618 (e.g., flat bottom surface of secondary coil 1406 created by winding around flat outer bottom edge 1411 of ferromagnetic shield 1404 as discussed herein with respect to FIG. 14) can increase distance 1904, thereby improving the electrical isolation between receiver system 1618 and antenna 1629.

According to some embodiments of the present disclosure, antenna 1629 can be coupled to ground via any one or more grounding brackets 1805a-c. With brief reference back to FIG. 18, each grounding bracket 1805a-c can be a monolithic structure formed of an anchor 1815, an interface 1817, and a connecting portion 1819 that couples anchor 1815 to interface 1817. Anchor 1815 can include a hole through which one or more mechanical fasteners, e.g., a bolt, screw, and the like, can tunnel to clamp grounding bracket 1805a to bottom housing portion 1604. When clamped, anchor 1815 can couple to both SIP 1616 and top housing portion 1602 in FIG. 16 so that any device, such as antenna 1629, contacting interface 1817 can be coupled to ground in embodiments where ground is formed by top and bottom housing portions 1602 and 1604. A better understanding of how anchor 1815 couples to top and bottom housing portions 1602 and 1604 can be ascertained with reference to FIGS. 20A-20D.

Figure 20B:
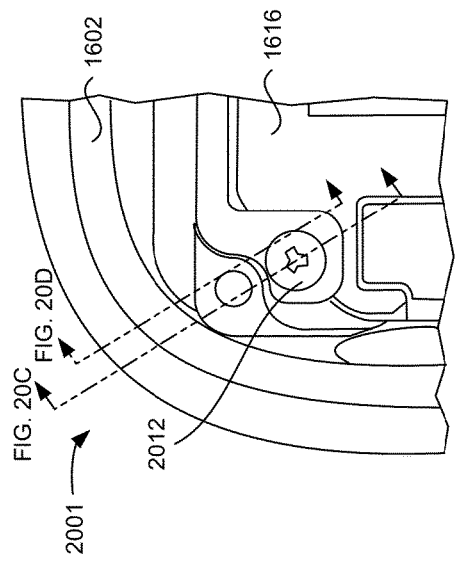
FIGS. 20A-20D are various top-down and cross-sectional views of a grounding bracket, according to some embodiments of the present disclosure.
Figure 20D:
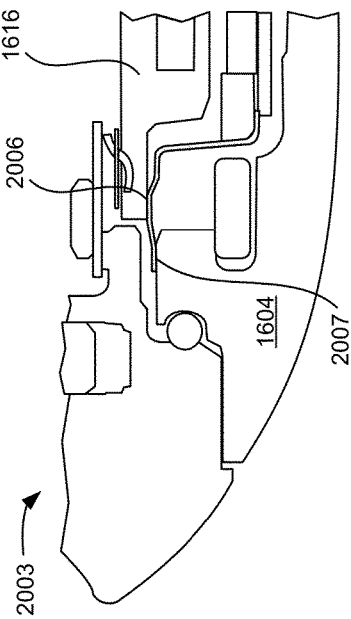
Figure 20A:
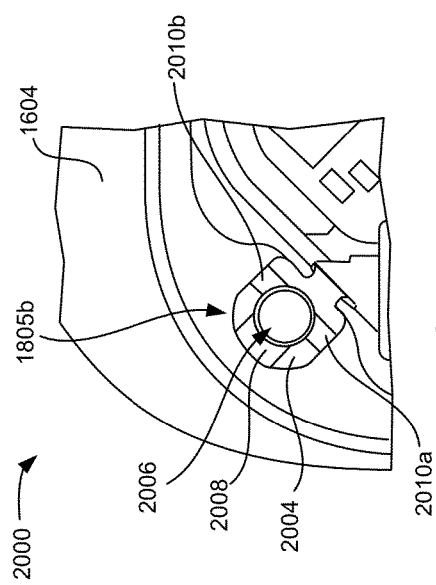
Figure 20C:
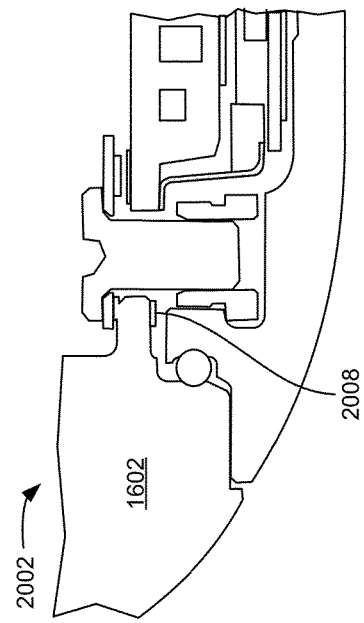

FIGS. 20A-20D are various top-down and cross-sectional views of a grounding bracket, e.g., any of grounding brackets 1805a-c, according to some embodiments of the present disclosure. Specifically, FIG. 20A is a close-up top-down view 2000 of an anchor 2004 of grounding bracket 1805b that is placed against bottom housing 1604, FIG. 20B is a top-down view 2001 of a bolt 2012 fastening top housing portion 1602 to bottom housing portion 1604 while clamping down against anchor 2004 of grounding bracket 1805b and SIP 1616, FIG. 20C is a cross-sectional view 2002 across anchor 2004 to show how anchor 2004 is coupled to top housing portion 1602, and FIG. 20D is a cross-sectional view 2003 across anchor 2004 to show how anchor 2004 is coupled to bottom housing portion 1604 and SIP 1616. It is to be appreciated that the disclosure with respect to grounding bracket 1805b in FIGS. 20A-20D can apply to all other grounding brackets, 1805a and 1508c.

As shown in FIG. 20A, anchor 2004 can be a conductive plate that includes a hole 2006 and a plurality of dimples including a housing dimple 2008 and two SIP dimples 2010a-b. Hole 2006 can be a vacant space through which bolt 2012 can thread to fasten top housing portion 1602 and SIP 1616 to bottom housing portion 1604, as shown in FIG. 20B while clamping down against anchor 2004 of grounding bracket 1805b. Each dimple can be a deflection of a section of anchor 2004 that has an arch structure forming a crest for making contact with other structures (see grounding bracket 1805b in FIG. 18 for a better perspective). For instance, as shown in FIG. 20C, housing dimple 2008 can have a crest that makes contact with top housing portion 1602; and, as shown in FIG. 20D, SIP dimples 2010a-b can have respective crests that make contact with SIP 1616 and bottom housing portion 1604. Thus, anchor 2004 can be a single structure that simultaneously contacts a plurality of physically distinct structures, i.e., top housing portion 1602, bottom housing portion 1604, and SIP 1616. Furthermore, by design of dimples 2008 and 2010a-b, anchor 2004 of grounding bracket 1805b can contact the structures via discrete contact locations instead of a broad interface surface across the entire surface area of anchor 2004. Dimples 2008 and 2010a-b of anchor 2004 are simple in design/manufacturability and can enable grounding bracket 1805 to provide a more robust and reliable connection with top housing portion 1602 and SIP 1616 by applying a constant contact pressure against top and bottom housing portions 1602 and 1604 and SIP 1616 due to the curved structure of dimples 2008 and 2010a-b.

e) Spacer and Wireless Charging Receiver System

In some embodiments, a portable electronic device can have different architectural configurations. For instance, with reference back to FIG. 16, one or more components of portable electronic device 1600 can be altered to provide different functionality. In one instance, antenna 1629 can be replaced with a spacer 1646, and receiver system 1618 can be replaced with a different receiver system 1648 so that portable electronic device 1600 is not capable of performing wireless telecommunication through radio waves but may have slightly improved inductive power transfer efficiency. Spacer 1646 can have a construction substantially similar to that of antenna 1629 except that spacer 1646 may not include a conductive body or grounding brackets, and an inner edge 1650 of spacer 1646 may not be oblong in shape. Instead, spacer 1646 may be completely formed of an insulating material, such as PSA, and inner edge 1650 can have a substantially circular profile that conforms to the outer profile of receiver system 1648, which may be configured according to receiver system 1200 discussed herein with respect to FIGS. 12A-12E. In some embodiments, both spacer 1646 and receiver system 1648 are implemented in portable electronic device 1600 and not only one without the other.

Figure 21:
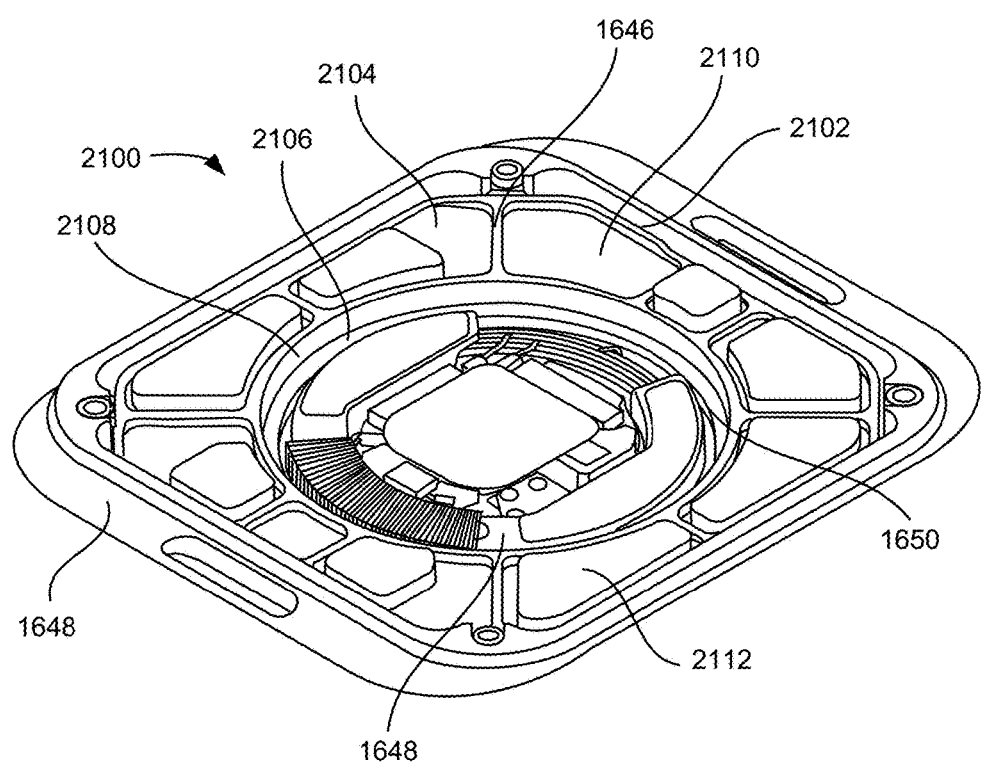
FIG. 21 is a perspective view of a partially assembled portable electronic device including a spacer and a receiver system, according to some embodiments of the present disclosure.

FIG. 21 is a perspective view of a partially assembled portable electronic device 2100 including spacer 1646 and receiver system 1648, according to some embodiments of the present disclosure. Similar to antenna 1629 in FIG. 16, the structure of spacer 1646 can be configured to maximize the use of space provided between receiver system 1648 and bottom housing portion 1604 by fitting in available space between them. Accordingly, spacer 1646 can have an outer edge 2102 that conforms to an inner edge of bottom housing 1604, and an inner edge 1650 that conforms to the outer circular profile of receiver system 1648. As such, both inner edge 1650 and step region 2108 can have a circular profile instead of only configuring step region 2108 to have a circular profile as discussed herein with respect to FIGS. 18 and 19. In some embodiments, spacer 1646 can include a top level 2104, a bottom level 2106, and a step region 2108 coupled between top level 2104 and bottom level 2106. As can be seen in FIG. 21, spacer 1646 can also include a plurality of recessed areas 2110, of which some are filled with foam structures 2112. Components of spacer 1646 that correspond with respective components of antenna 1629 can be substantially similar in construction and material, and thus details of such components can be referenced in the disclosure with respect to FIGS. 18 and 19.

According to some embodiments of the present disclosure, unlike antenna 1629 which includes a non-conductive element and a conductive body attached to the element, spacer 1646 may be completely formed of a non-conductive material and may not include a conductive body attached to it. Thus, spacer 1646 can be configured to occupy space between bottom housing 1604 and receiver system 1618 to confine receiver system 1618 in position within the portable electronic device and help keep receiver system 1618 in place. By using spacer 1646 when the portable electronic device is not configured to need an antenna to perform wireless communication through radio waves, the architecture of the portable electronic device will not need to be completely altered, thereby saving manufacturing time and cost as the configurations of the vast majority of the other electrical components, e.g., those components other than receiver system 1618, can be used for both embodiments without modification to their structure/size.

f) Bottom Housing Portion

As briefly mentioned herein with respect to FIG. 16, a bottom housing portion can mate with a top housing portion to form an interior cavity within which electronic components can be positioned. The bottom housing portion can include a window through which one or more electrical signals can be transmitted to enable certain functionality of the portable electronic device. A better understanding of the construction of the bottom housing portion can be ascertained with reference to FIG. 22.

Figure 22:
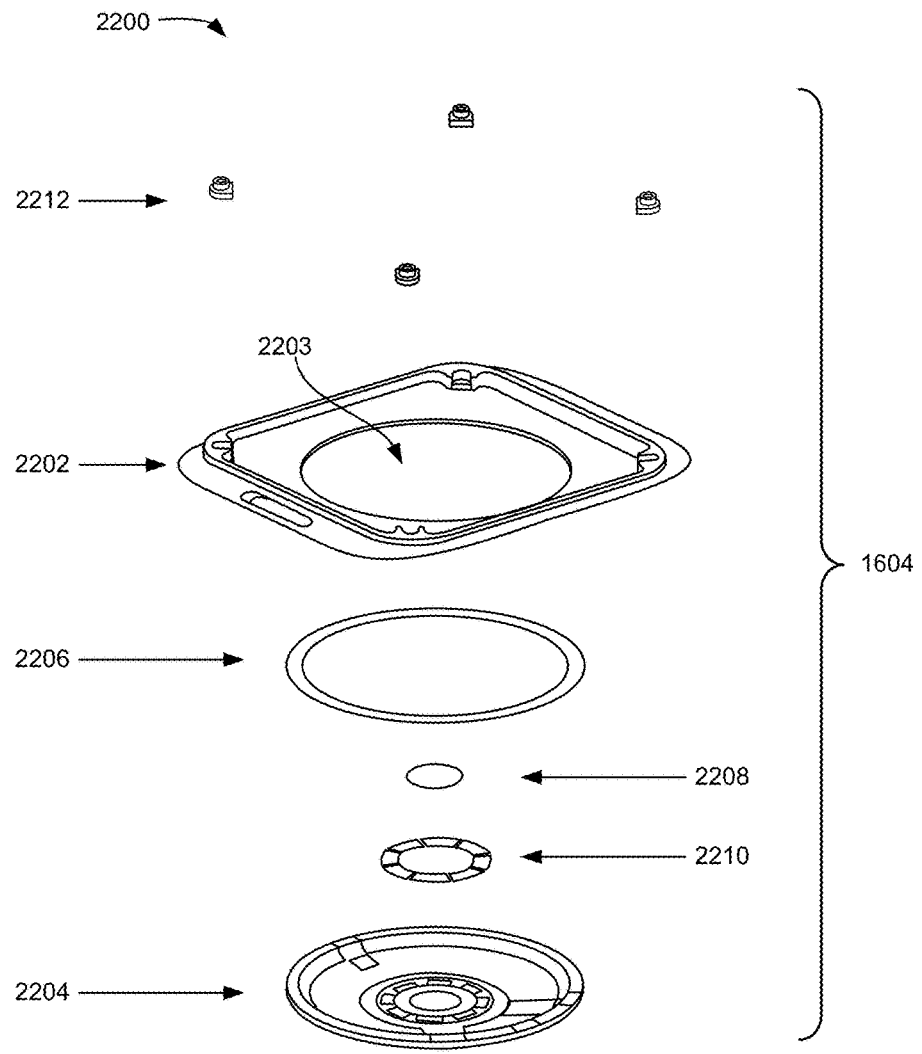
FIG. 22 is an exploded view of a bottom housing portion for a portable electronic device, according to some embodiments of the present disclosure.

FIG. 22 is an exploded view 2200 of bottom housing portion 1604 for a portable electronic device, e.g., portable electronic device 1600 in FIG. 16, according to some embodiments of the present disclosure. Bottom housing portion 1604 can also include a plurality of fastening mechanisms 2212 positioned at corners of structure body 2202. Fastening mechanisms 2212 can enable bolts to secure a top housing portion, e.g., top housing portion 1602 in FIG. 16, to bottom housing portion 1604. Fastening mechanisms can be T-nuts having flanges that slide into corresponding undercut regions within bottom structure body 2202. The undercut regions enable the T-nuts to secure top housing portion 1602 to bottom housing portion 1604 without adhesive materials while providing a mechanical interlocking mechanism that substantially prevents separation of the two housings.

In some embodiments, bottom housing portion 1604 can include a structure body 2202 and a window 2204 coupled to a bottom of bottom housing portion 1604 via an adhesive layer 2206. Structure body 2202 can be formed of a stiff material with insulating electrical properties, such as a crystalline structure formed of black zirconia. Structure body 2202 can include a circular opening 2203 at its center where one or more electrical devices can be positioned. In some embodiments, window 2204 is a circular dome-shaped structure that is adhered to the bottom of bottom housing portion 1604 such that the circular edge of window 2204 is adhered along the circular edge of opening 2203. Window 2204 can be formed of any suitable transparent and durable material, such as sapphire crystal. One or more components, such as a Fresnel lens 2208 and a wheel 2210 can be adhered to window 2204 for enabling functionality of one or more sensor components within the portable electronic device, such as sensor module 1636 in FIG. 16, the arrangement of which is better shown in FIG. 23.

Figure 23:
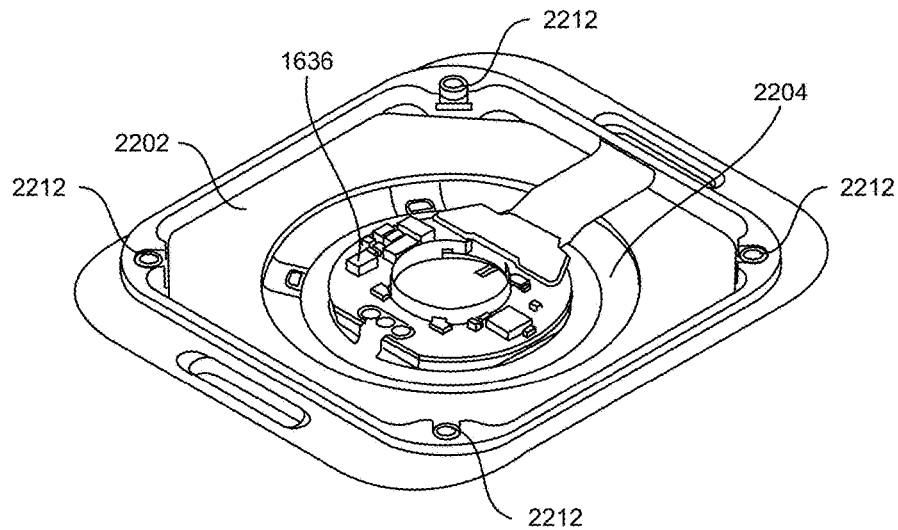
FIG. 23 is a simplified diagram illustrating a perspective view of a sensor module mounted on a bottom housing portion of a portable electronic device, according to some embodiments of the present disclosure.

FIG. 23 is a simplified diagram illustrating a perspective view of sensor module 1636 mounted on bottom housing portion 1604, according to some embodiments of the present disclosure. Sensor module 1636 can be mounted in the center of bottom housing portion 1604 and against window 2204 such that its sensors are also positioned at the center of bottom housing portion 1604. In some instances, a heart rate sensor (e.g., heart rate sensor 1102 in FIG. 11) comprising a thin layer of platinum can be positioned at the center of bottom housing portion 1604. Sensors of sensor module 1636 can perform sensing through window 2204. In some embodiments, fastening mechanisms 2212 can be positioned at each corner of bottom housing portion 1604 to fasten bottom housing portion 1604 with top housing portion 1602.

Figure 24:
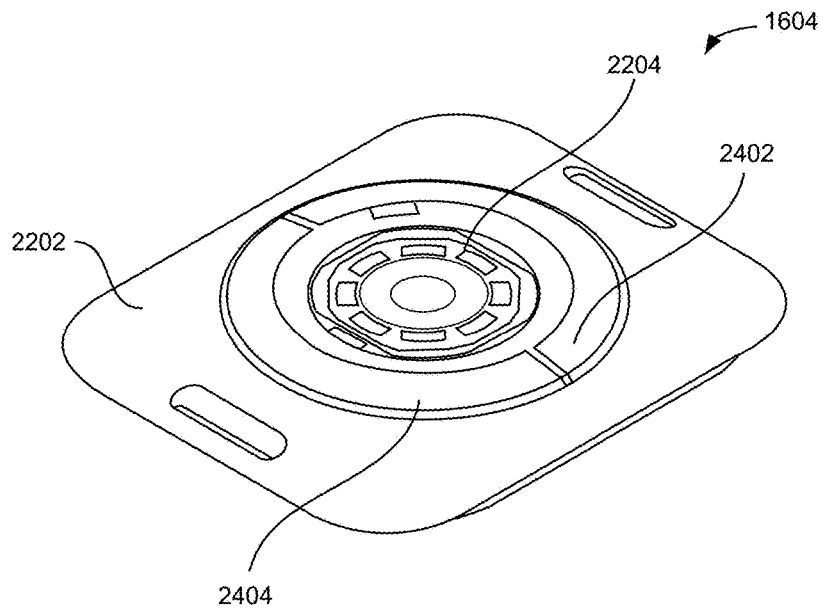
FIG. 24 is a bottom perspective view illustration of a bottom housing portion of a portable electronic device, according to some embodiments of the present disclosure.

FIG. 24 illustrates a bottom perspective view of bottom housing portion 1604, according to some embodiments of the present disclosure. Bottom housing portion 1604 can include window 2204 that provides an avenue through which one or more parameters of an external environment can be monitored by sensors coupled to sensor module 1636. Furthermore, bottom housing portion 1604 can include one or more contacts for making contact with an external surface, such as a user's wrist or arm. For instance, bottom housing portion 1604 can include a first external contact 2402 and a second external contact 2404. According to some embodiments of the present disclosure, first and second external contacts 2402 and 2404 can be utilized to perform EKG sensing of a user's heart. This sensing can be performed by forming a closed-loop circuit through an external structure, such as the user's body. For instance, a closed-loop circuit can be formed when a user touches a dial, such as dial 1610 in FIG. 16. The closed-loop circuit can begin at portable electronic device 1600, then continue into the user's arm through at least one of first and second external contacts 2402 and 2404. The circuit can flow through the user's body and out of the finger on the other arm into dial 1610 when the user touches dial 1610. By forming this closed-loop circuit, one or more processing devices in portable electronic device 1600 can perform EKG measurement functions of a user's body. In some embodiments, first external contact 2402 is used for a ground reference to minimize noise, and second external contact 2404 is used as the contact for sending a signal through the user's body.

2. Assembled Bottom Housing Portion of a Portable Electronic Device Having a Secondary Receiving Element Formed of a Coil Wound about a Portion of the Primary Coil FIGS. 25A-25B are cross-sectional view illustrations of assembled portions of a portable electronic device to show the positional relationship between components within the portable electronic device, according to some embodiments of the present disclosure. Specifically, FIG. 25A is a cross-sectional view illustration 2500 of the assembled portion shown in FIG. 19 across the horizontal cut line, and FIG. 25B is a cross-sectional view illustration 2501 of the assembled portion shown in FIG. 19 across the vertical cut line. The assembled portion does not include a majority of top housing portion 1602 for ease of discussion.

As shown in the horizontal cross-sectional view in FIG. 25A, top housing portion 1602 and bottom housing portion 1604 can be mated to form an internal cavity within which a plurality of internal components can be housed. In some embodiments, SIP 1616 can be positioned near the top of bottom housing portion 1604 and be positioned above a plurality of other internal components within bottom housing portion 1604, such as receiver system 1618, antenna 1629, sensor module 1636, and alignment module 1634. Receiver system 1618 can be positioned within opening 1630 of antenna 1629; and, receiver system 1618 can be positioned coplanar to antenna 1629, meaning receiver system 1618 can be positioned along the same horizontal plane in which antenna 1629 is positioned. In some embodiments, sensor module 1636 can be mounted on an inner surface of window 2204 and positioned within an inner diameter of receiver system 1618. Sensor module 1636 can include a thin heart rate sensor 2502 and one or more photo diodes 2504 for performing sensing functions. Alignment module 1634 can be coupled to a top surface of sensor module 1636 and also be positioned within an inner diameter of receiver system 1618. DC shield 1638 can overhang from lateral edges of magnet 1642.

According to some embodiments of the present disclosure, receiver system 1618, sensor module 1636, and alignment module 1634 are all positioned within opening 1630 of antenna 1629. Although not shown in FIG. 25A, conductive antenna body 1108 can be disposed on the bottom surface of antenna element 1802. As shown in FIG. 25A, antenna 1629 can be vertically positioned over part of bottom housing portion 1604 and window 2204. Specifically, top level 1806 can be vertically positioned over part of bottom housing portion 1604, bottom level 1808 can be vertically positioned over part of window 2204, and step region 1810 can be laterally positioned beside both bottom housing portion 1604 and window 2204. By configuring antenna 1629 to extend over portions of both bottom housing portion 1604 and window 2204, the size of antenna 1629 can be maximized given the limited amount of space within the portable electronic device, thereby improving the operability of antenna 1629.

As shown in the vertical cross-sectional view in FIG. 25B where the top of the device is to the right and the bottom of the device is to the left, ferromagnetic shield 1404 can be positioned over parts of primary coil 1402 near the bottom of the device, while ferromagnetic shield 1404 is not positioned over parts of primary coil 1402 near the top of the device, as discussed herein with respect to FIGS. 14A-14E. Furthermore, secondary coil 1406 can also be positioned near the bottom of the device and not at the top of the device, and be wound around parts of both ferromagnetic shield 1404 and primary coil 1402. Unlike the left and right parts of antenna 1629, at least some top and bottom parts of antenna 1629 may not have a bottom level and/or a step region, as shown in FIG. 25B. Not having the bottom level and/or the step region provides greater electrical isolation between antenna 1629 and receiver system 1618. As further shown in FIG. 25A, capacitors 1813 can be disposed in a recessed area of top level 1806 of antenna 1629 so that capacitors 1813 do not substantially add to the device's z-height.

IV. Coating of the Window for a Portable Electronic Device

In some embodiments, the window of the back housing can include a plurality of coated layers that include ink layers that are either transparent or opaque to infrared (IR) radiation for enabling the sensor devices to measure the outside environment. FIGS. 26A-26D and 27A-27H illustrate different coating configurations of a window, according to some embodiments of the present disclosure. Specifically, FIGS. 26A-26D are a series of illustrations showing how an internal surface of window 2204 can be coated with different layers in a first configuration, and FIGS. 27A-27H are a series of illustrations showing how an internal surface of window 2204 can be coated with different layers in a second configuration. When combined as a multi-layered coating, the different layers can block IR radiation in specific areas of window 2204 while enabling propagation of IR radiation in other areas of the window to enable the operation of one or more sensors of portable electronic device 1600 while minimizing IR radiation leakage out of bottom housing portion 1604 and measurement noise from the external environment.

Figure 26A:
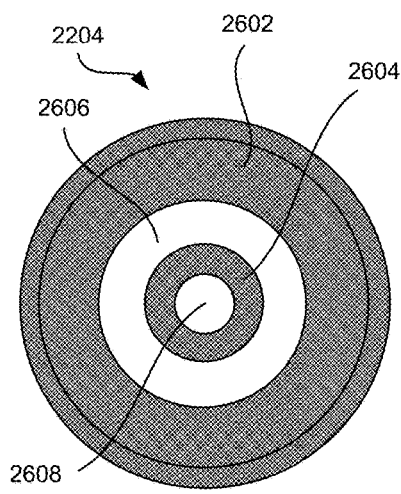
FIGS. 26A-D are illustrations showing the different layers that are coated on a window of a bottom housing portion, according to some embodiments of the present disclosure.
Figure 26B:
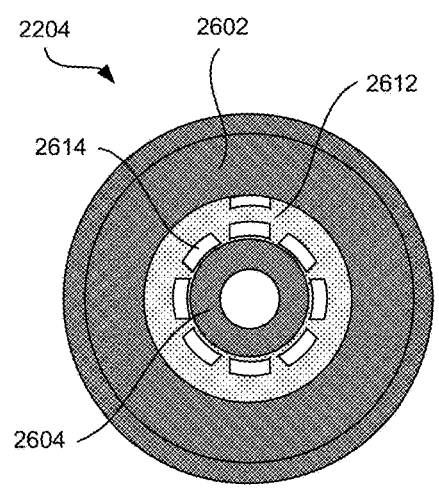

With reference to FIG. 26A illustrating the first configuration of ink coatings on window 2204, IR opaque layers 2602 and 2604 can be coated on select areas of window 2204. IR opaque layers 2602 and 2604 can be formed of IR opaque ink that can substantially resist the transmission of IR radiation such that IR radiation does not substantially transmit through the IR opaque ink. IR opaque layer 2602 can be positioned at an outer region of window 2204, and IR opaque layer 2604 can be positioned at an inner region of window 2204, as shown in FIG. 26A. Both IR opaque layers 2602 and 2604 can be annular in dimension and be positioned spaced apart so that a first uncoated region 2606 is not covered by IR opaque layers 2602 and 2604. Furthermore, IR opaque layer 2604 can be annular so that a second uncoated region 2608 located at the center of window 2204 is also not covered by IR opaque layers 2602 and 2604.

In some embodiments, an IR transparent layer 2612 can be coated on a surface of first uncoated region 2606. IR transparent layer 2612 can be formed of an IR transparent ink that can substantially allow the transmission of IR radiation such that IR radiation can be transmitted through the IR transparent ink without significant resistance. IR transparent layer 2612 can be arranged such that one or more openings 2614 remain in IR transparent layer 2612. One or more openings 2614 can be regions where window 2204 is not covered by IR transparent layer 2612, so that one or more sensors within portable electronic device 1600 can receive input, or send output, signals through window 2204.

In some embodiments, IR transparent layer 2612 may slightly overlap a portion of IR opaque layers 2602 and 2604 at regions where IR transparent layer 2612 meets IR opaque layers 2602 and 2604 to ensure complete coverage of window 2204 at the interface between IR transparent layer 2612 and IR opaque layers 2602 and 2604.

Figure 26C:
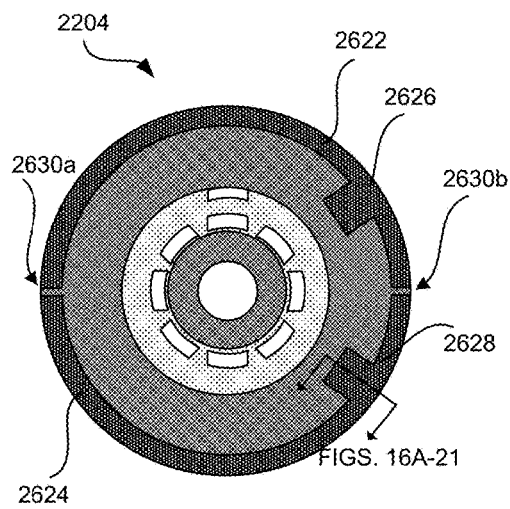
Figure 26D:
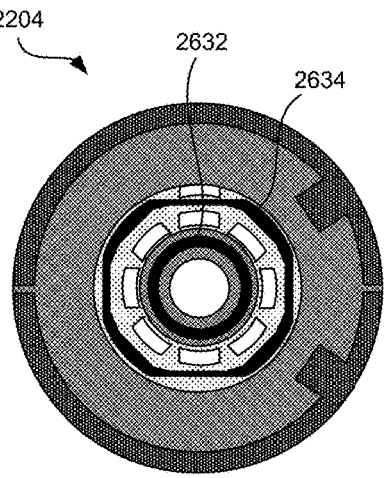

Once the IR opaque and IR transparent layers are coated on window 2204, a contact layer can then be coated on portions of IR opaque layer 2602, as shown in FIG. 26C. In some embodiments, the contact layer includes a first contact 2622 and a second contact 2624. Both first and second contacts 2622 and 2624 can be positioned at the very outer edge of window 2204, and can be electrically separated by gaps 2630*a* and 2630*b*. First and second contacts 2622 and 2624 can wrap around the outer edge of window 2204 so that first and second contacts 2622 and 2624 are also present on the outer surface of window 2204 (see FIG. 24 shown by external contacts 2402 and 2404). Contact pads 2626 and 2628 can be extensions of first and second contacts 2622 and 2624, respectively, that provide contact surfaces with which a sensor device can make contact to receive input signals from first and second contacts 2622 and 2624. The contact layer can be a thin layer of conductive material suitable such as a metal alloy formed of AlTiN or CrSiCN As shown in FIG. 26D, one or more adhesive layers can be coated on the IR opaque and IR transparent coatings. For instance, a first adhesive layer 2632 can be coated on IR opaque layer 2604, and a second adhesive layer 2634 can be coated on IR transparent layer 2612. First and second adhesive layers 2632 and 2634 can secure one or more sensor components, such as sensor module 1636, to window 2204. In some embodiments, first and second adhesive layers 2632 and 2634 can be formed of any suitable material for attaching two structures together, such as pressure sensitive adhesive (PSA).

With reference now to FIG. 27A illustrating the second configuration of ink coatings on window 2204, an external contact layer can be coated directly on an outer surface of window 2204. The contact layer can include a first external contact 2702 and a second external contact 2704 electrically and physically separated by gaps 2706*a* and 2706*b*. In some embodiments, external contacts 2702 and 2704 are conductive ink layers that are coated only on the outer surface of window 2204 and the outer edge of window 2204 and do not extend to an inner surface of window 2204.

In some embodiments, an IR transparent layer 2708 can be coated on an inner surface of window 2204 opposite of the outer surface as shown in FIG. 27B. IR transparent layer 2708 can be formed of an IR transparent ink that can substantially allow the transmission of IR radiation such that IR radiation can be transmitted through the IR transparent ink without significant resistance. IR transparent layer 2708 can have an annular profile and be arranged to include one or more openings 2710. Openings 2710 can be regions where window 2204 is not covered by IR transparent layer 2708, so that one or more sensors of sensor module 1636 within portable electronic device 1600 can receive input, or send output, signals through window 2204. IR transparent layer 2708 can have a diameter smaller than that of, and centered to, window 2204 so that the position of IR transparent layer 2708 results in a first uncovered region 2709 surrounding an outer diameter of IR transparent layer 2708 and a second uncovered region 2711 within an inner diameter of IR transparent layer 2708.

As shown in FIG. 27C, an IR opaque layer including a first portion 2712 and a second portion 2714 can then be coated on select areas of window 2204. First portion 2712 can be coated on first uncovered region 2709 so that it surrounds an outer diameter of IR transparent layer 2708; and second portion 2714 can be coated on second uncovered region 2711 within an inner diameter of IR transparent layer 2708. Both first and second portions 2712 and 2714 can have an annular profile as shown in FIG. 27C. First portion 2712 can abut the outer diameter of IR transparent layer 2708 and be positioned away from the outer edge of window 2204 so that an uncovered region 2720 of window 2204 is present near the outer edge of window 2204. Second portion 2714 can abut the inner diameter of IR transparent layer 2708 and be positioned away from the center of window 2204 so that an uncovered region 2722 is present at the center of window 2204. In some embodiments, first portion 2712 includes an intermittently covered region 2716 that is formed of an alternating pattern of concentric IR opaque rings and uncovered surfaces of window 2204, as shown in FIG. 27C. Intermittently covered region 2716 can abut IR transparent layer 2708. As further shown in FIG. 27C, the IR opaque layer can also include IR opaque patches 2718 and 2719 positioned on the inner surface of window 2204 directly across from gaps 2706*a-b* positioned on the outer surface of window 2204. In some embodiments, some parts of window 2204 may be exposed at regions 2717*a-b* beside IR opaque patches 2718 and 2719. The IR opaque layer can be formed of IR opaque ink that can substantially resist the transmission of IR radiation such that IR radiation does not substantially transmit through the IR opaque ink.

Once the IR opaque layer is formed, a filler layer 2724 can be formed on the uncovered surface of window 2204 in intermittent region 2716. Filler layer 2724 can be a cosmetic layer formed of a material having a pigment that is lighter than that of first portion 2712 of the IR opaque layer, such as a gray highlight ink. It is to be appreciated that any suitable cosmetic ink can be used to form filler layer 2724 such as a material having a pigment that is darker than that of first portion 2712 of the IR opaque layer. Then, as shown in FIG. 27E, an encapsulation layer 2726 can be formed over intermittent region 2716 to cover exposed surfaces of filler layer 2724 to provide IR-resisting functionality over intermittent region 2716. Encapsulation layer 2726 can be formed of the same material as the IR opaque layer.

In some embodiments, IR transparent patches 2728*a-b* can then be formed over the exposed regions 2717*a-b* beside IR opaque patches 2718 and 2719, as shown in FIG. 27F; and then contact extensions 2732 and 2734 can be patterned onto the inner surface of window 2204, as shown in FIG. 27G. Contact extensions 2732 and 2734 can extend from the outer edge of window 2204 toward the center of window 2204 and cover a portion of encapsulation layer 2726. Then, as shown in FIG. 27H, contact pads 2736 and 2738 can be patterned over portions of respective contact extensions 2732 and 2734. For instance, contact pad 2736 can be patterned over a portion of contact extension 2732 such that it covers the end of contact extension 2732 that is closest to the center of window 2204, and likewise for contact pad 2736 with respect to contact extension 2734. Contact pads 2736 and 2738 can provide a contact surface against which one or more electrical components, such as one or more sensing components in sensor module 1636, can couple. Contact pads 2736 and 2738 can be electrically coupled with external contacts 2702 and 2704 shown in FIG. 27A via contact extensions 2732 and 2734. Thus, by coupling to contact pads 2736 and 2738, the one or more sensing components can utilize external contacts 2702 and 2704 to sense the external environment.

Figure 28A:
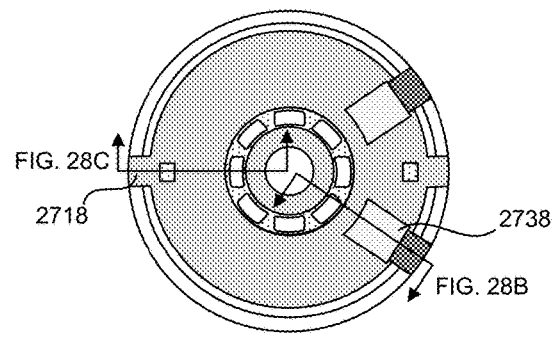
FIG. 28A is a top-down view of a window after all of the layers have been patterned as shown in FIG. 27H to show the two cut lines for the cross-sectional views in FIGS. 28B-28C, according to some embodiments of the present disclosure.

Although various layers shown in FIGS. 27A-27H are shown abutting one another, it is to be appreciated that abutting layers may overlap one another to ensure that no gaps are present between them and to ensure complete coverage of window 2204 at the interfaces. A better perspective of this concept can be appreciated with respect to FIGS. 28A-28C. FIG. 28A is a top-down view of window 2204 after all of the layers have been patterned as shown in FIG. 27H to show the two cut lines for the cross-sectional views in FIGS. 28B-28C. Specifically, FIG. 28B is a cross-sectional view 2800 of window 2204 through contact pad 2738, and FIG. 28C is a cross-sectional view 2801 of window 2204 through opaque patch 2718.

Figure 28B:
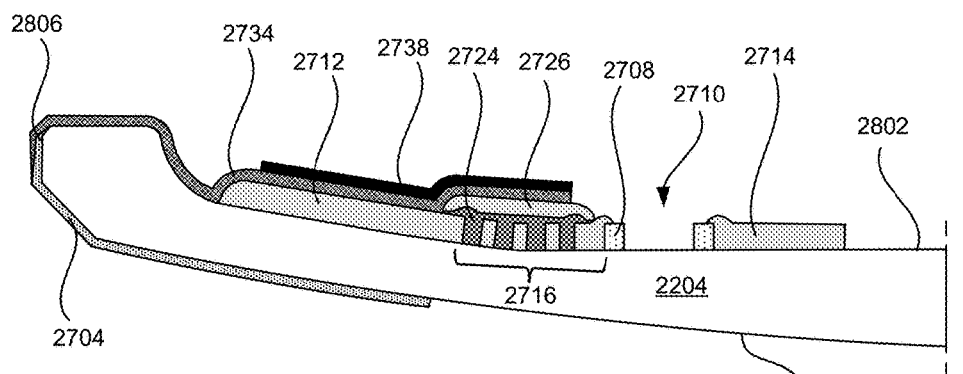
FIG. 28B is a cross-sectional view of a window through a contact pad, according to some embodiments of the present disclosure.

As shown in FIG. 28B, window 2204 can have an inner surface 2802 configured to be positioned inside of the portable electronic device when assembled, an outer surface 2804 configured to be positioned outside of the portable electronic device when assembled, and an outer edge 2806. IR transparent layer 2708 having openings 2710 can be patterned directly on inner surface 2802, and first and second portions 2712 and 2714 of the IR opaque layer can be patterned directly on inner surface 2802 while overlapping a portion of the top surface of IR transparent layer 2708 at its inner and outer diameters, which are shown as left and right edges of IR transparent layer 2708 in FIG. 28B. Filler layer 2724 can be patterned directly on inner surface 2802 while overlapping portions of intermittently covered region 2716 of first portion 2712 of the IR opaque layer; and encapsulation layer 2726 can be patterned over filler layer 2724 and on parts of first portion 2712 abutting filler layer 2724. As further shown in FIG. 28B, external contact 2704 can be patterned on outer surface 2804 and extend over outer edge 2806 of window 2204. Edge 2806 can also be covered by contact extension 2734, which can extend from edge 2806 directly on window 2204, over part of first portion 2712 of the IR opaque layer, and end over encapsulation layer 2726. And, contact pad 2738 can be patterned over a portion of contact extension 2734 such that contact pad 7238 covers the portion of contact extension 2734 that is closest to center 2808 of window 2204.

Figure 28C:
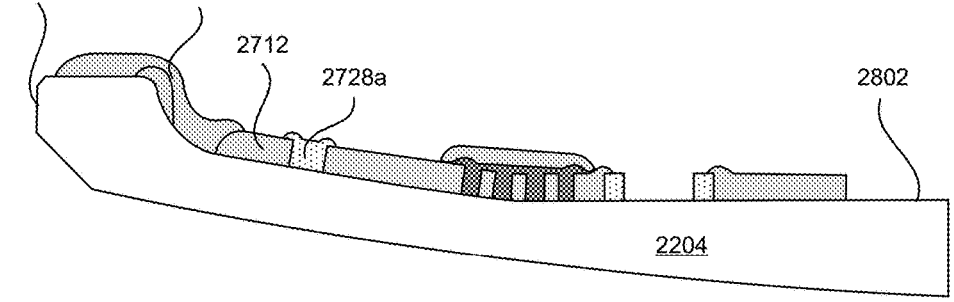
FIG. 28C is a cross-sectional view of a window through an opaque patch, according to some embodiments of the present disclosure.

With reference to FIG. 28C, the cut line may pass directly between both external contacts 2702 and 2704 so no external contact can be seen in cross-sectional view 2801, and since the cut line does not pass through a contact pad, no contact extension 2734 and contact pad 2738 can be seen. What can be seen, however, are IR opaque patch 2718 and IR transparent patch 2728a. As shown, IR opaque patch 2718 can extend very close to, if not all the way to, edge 2806 of window 2204 and overlap a portion of the top surface of first portion 2712 of the IR opaque layer at its inner and outer diameters. IR transparent patch 2728a can be patterned directly on inner surface 2802 while overlapping a portion of the top surface of first portion 2712 of the IR opaque layer. Thus, as can be seen with reference to FIGS. 28B and 28C, no gaps may exist between adjacent layers of IR opaque and IR transparent ink.

As mentioned in FIG. 24, first and second external contacts 2402 and 2404 can be used as contacts for sensing parameters of an external surface, such as user's arm, through physical contact to perform EKG sensing functions. In order for first and second external contacts 2402 and 2404 to sense the external environment and provide the sensed data to components within the portable electronic device, first and second external contacts 2402 and 2404 can be positioned on the outer surface of window 2204, while providing an interface surface on an inner surface of window 2204 to couple with sensor devices, as will be discussed further herein with respect to FIGS. 29A-34.

Figure 29A:
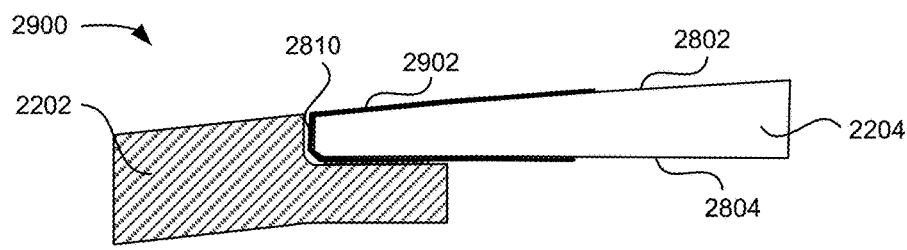
FIG. 29A is a simplified diagram illustrating an exemplary configuration where a contact wraps around an edge of a window, according to some embodiments of the present disclosure.

FIGS. 29A-21 illustrate cross-sectional views across a portion of an external contact, a window, and a structure body for a bottom housing portion (e.g., bottom housing portion 1604), and top down views of an external region of the bottom housing portion, according to some embodiments of the present disclosure. FIGS. 29A-21 show some different ways a contact can extend to an outer surface of a window to sense parameters of external surfaces, while also providing a contact surface to couple with sensor devices inside of a portable electronic device.

FIG. 29A illustrates an exemplary configuration 2900 where an external contact 2902 wraps around edge 2810 of window 2204, according to some embodiments of the present disclosure. As shown, contact 2902 can have portions that are positioned on outer surface 2802, inner surface 2804, and edge 2810 of window 2204. Accordingly, external surfaces contacting external contact 2902 on outer surface 2802 can generate signals that can be measured by contacting with regions of external contact 2902 on inner surface 2804.

Figure 29B:
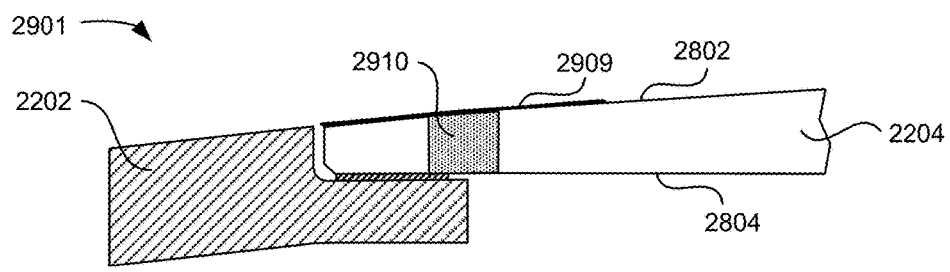
FIG. 29B is a simplified diagram illustrating an exemplary configuration where a contact is coupled to a via, according to some embodiments of the present disclosure.

FIG. 29B illustrates an exemplary configuration 2901 where a contact 2909 is coupled to a via 2910, according to some embodiments of the present disclosure. Contact 2909 can be a layer of conductive material disposed on outer surface 2802 of window 2204. Contact 2909 can be coupled to via 2910 that extends through window 2204 to route signals from contact 2909 to a region of inner surface 2804.

Figure 29C:
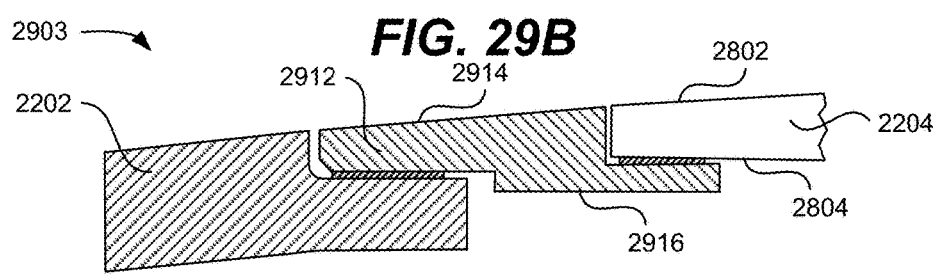
FIG. 29C is a simplified diagram illustrating another exemplary configuration where a contact is configured as a standalone structure that can route signals from an outer surface to an inner surface of a window, according to some embodiments of the present disclosure.

FIG. 29C illustrates another exemplary configuration 2903 where a contact 2912 is configured as a standalone structure that can route signals from an outer surface 2914 to an inner surface 2916 of contact 2912, according to some embodiments of the present disclosure. Contact 2912 can be directly attached to both structure body 2202 and window 2204 so that window 2204 is structurally coupled with structure body 2202. In some embodiments, a bottom surface of contact 2912 can attach to structure body 2202 and a top surface of a ledge of contact 2912 can attach to a bottom surface of window 2204. The structure of contact 2912 allows external surfaces in contact with outer surface 2914 of contact 2912 to generate signals that can be measured by contacting its inner surface 2916.

Figure 30:
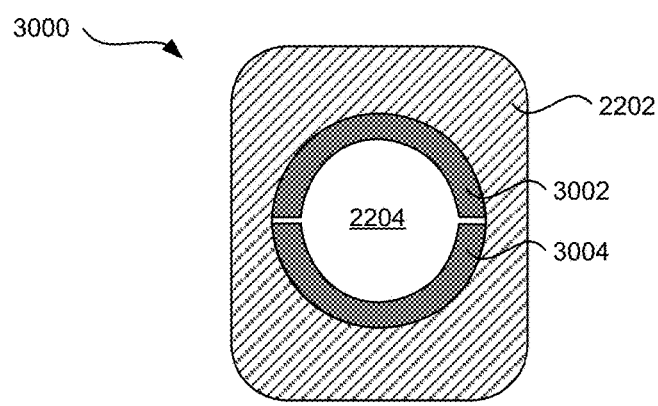
FIG. 30 is a simplified diagram illustrating a top-down view of an external region of a bottom housing portion having first and second contacts and configured as any of the contacts discussed in FIGS. 29A-29C, according to some embodiments of the present disclosure.

FIG. 30 illustrates a top-down view of an external region of a bottom housing portion 3000 having first and second contacts 3002 and 3004 configured as any of the contacts discussed in FIGS. 29A-29C. As shown, first and second contacts 3002 and 3004 can be positioned at the every outer edge of window 2204 such that they abut structure body 2202 of bottom housing portion 3000. Although embodiments described in FIGS. 29A-30 show first and second contacts 3002 and 3004 abutting structure body 2202, embodiments are not so limited. In some embodiments, an intermediate structure can be disposed between first and second contacts 3002 and 3004 and structure body 2202.

Figure 31A:
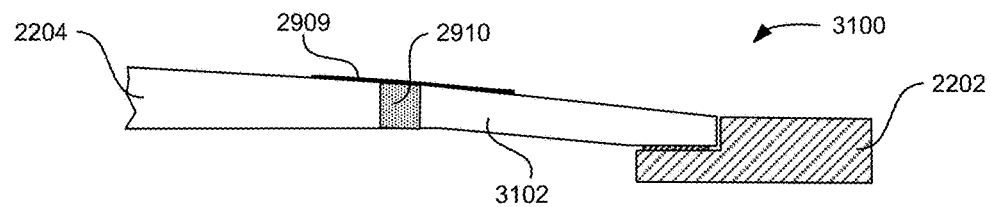
FIG. 31A is a simplified diagram illustrating an exemplary configuration where an intermediate structure is disposed between a via and a structure body, according to some embodiments of the present disclosure.

FIG. 31A illustrates an exemplary configuration 3100 where an intermediate structure 3102 is disposed between via 2910 and structure body 2202, according to some embodiments of the present disclosure. Intermediate structure 3102 can allow contact 2909 and via 2910 to be positioned farther away from structure body 2202 so that one or more sensors can measure an external environment through intermediate structure 3102. Details of contact 2909 and via 2910 can be referenced from disclosures regarding FIG. 29B. As mentioned herein with respect to FIG. 16, sensor module 1636 including one or more sensors, can be attached to window 2204. Thus, in some embodiments, an additional transparent structure (e.g., a flattening insert) can be attached to window 2204 to planarize an inner surface of the bottom housing portion as shown in FIG. 31B.

Figure 31B:
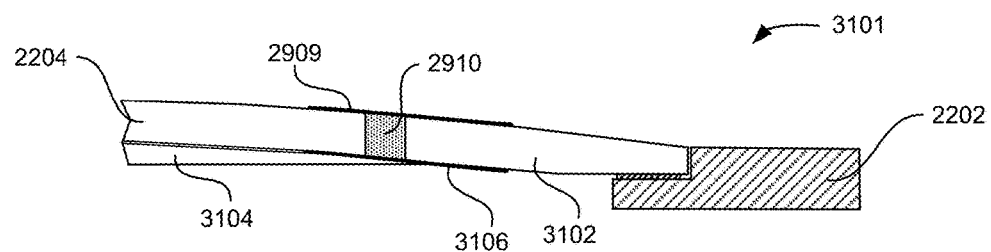
FIG. 31B is a simplified diagram illustrating an exemplary configuration where an inner surface of a window includes a flattening insert, according to some embodiments of the present disclosure.

FIG. 31B illustrates an exemplary configuration 3101 where an inner surface of window 2204 includes a flattening insert 3104, according to some embodiments of the present disclosure. Flattening insert 3104 can have a curved top surface for coupling with window 2204, and a flat bottom surface opposite of the curved top surface upon which sensor module (not shown) can attach. In some embodiments, flattening insert 3104 can be a transparent structure similar to that of window 2204.

Figure 32:
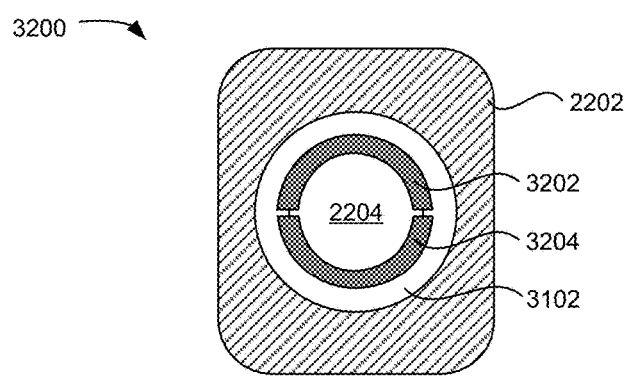
FIG. 32 is a simplified diagram illustrating a top-down view of an external region of a bottom housing portion including an intermediate structure and first and second contacts configured as shown in FIGS. 31A-31B, according to some embodiments of the present disclosure.

FIG. 32 illustrates a top-down view of an external region of a bottom housing portion 3200 including intermediate structure 3102 and first and second contacts 3202 and 3204 configured as shown in FIGS. 31A-31C. Intermediate structure 3102 can be an annular structure positioned between first and second contacts 3202 and 3204 and structure body 2202 so that first and second contacts 3202 and 3204 do not abut structure body 2202. In some embodiments, intermediate structure 3102 does not have to be formed of a transparent structure like window 2204. Instead, intermediate structure 3102 can be formed of a non-transparent structure similar to structure body 2202.

Figure 33A:
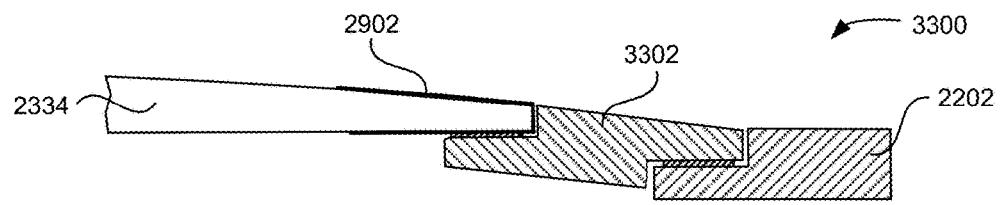
FIG. 33A is a simplified diagram illustrating an exemplary configuration where an intermediate structure is disposed between a contact on a window and a structure body, according to some embodiments of the present disclosure.

FIG. 33A illustrates an exemplary configuration 3300 where an intermediate structure 3302 is disposed between contact 2902 on window 2204 and structure body 2202, according to some embodiments of the present disclosure. Details of contact 2902 can be referenced from disclosures regarding FIGS. 28B and 29A. Intermediate structure 3302 can allow contact 2902 to be positioned farther away from structure body 2202. In some embodiments, intermediate structure 3302 is a separate structure that is attached to contact 2902 and structure body 2202. Intermediate structure 3302 can be designed to extend window 2204, along with contact 2902, farther outward so that a better contact can be made between an external surface and an external surface of contact 2902, and so that intermittent contact between the external surface and structure body 2202 is minimized (this may be desirable because noise can be generated in the system's ground when the external surface makes contact with structure body 2202, i.e., bottom housing portion 1604). In some embodiments, intermediate structure 3302 can be formed of the same material as structure body 2202, such as zirconia.

Figure 33B:
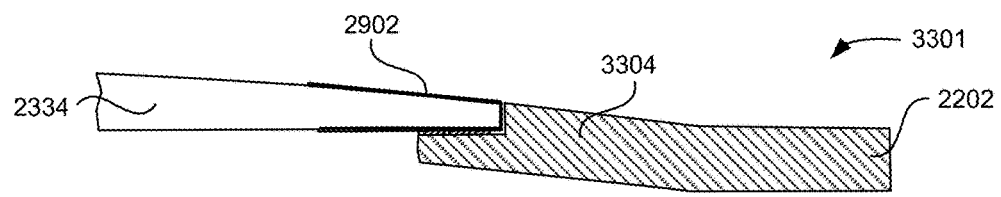
FIG. 33B is a simplified diagram illustrating an exemplary configuration where an intermediate structure is formed as part of a structure body, according to some embodiments of the present disclosure.

Although FIG. 33A illustrates intermediate structure 3302 as a separate structure, embodiments are not so limited. FIG. 33B illustrates an exemplary configuration 3301 where intermediate structure 3304 is formed as part of structure body 2202, according to some embodiments of the present disclosure. In such embodiments, intermediate structure 3302 and structure body 2202 can form a monolithic structure and be formed of the same material.

Figure 34:
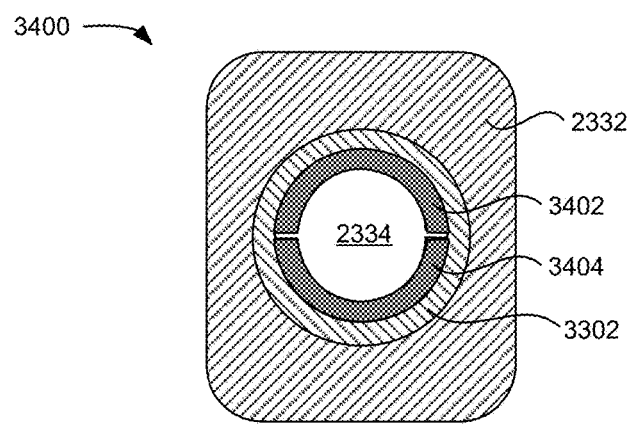
FIG. 34 is a simplified diagram illustrating a top-down view of an external region of a bottom housing portion including an intermediate structure and first and second contacts configured as shown in FIGS. 33A-33B, according to some embodiments of the present disclosure.

FIG. 34 illustrates a top-down view of an external region of a bottom housing portion 3400 including intermediate structure 3302 and first and second contacts 3402 and 3404 configured as shown in FIGS. 33A-33C. Intermediate structure 3302 can be an annular structure positioned between first and second contacts 3402 and 3404 and structure body 2202 so that first and second contacts 3402 and 3404 extend farther outward to make better contact with an external surface.

V. Touch-Sensitive Crown Dial for Portable Electronic Devices

As discussed herein with respect to FIG. 16, a top housing portion can include a dial. The dial can be a touch sensitive dial that can act as a contact for performing EKG sensing. The dial can include various components that, when coupled together, form a conductive pathway from an outer surface of the dial to inner touch components, as discussed herein with respect to FIGS. 35 and 36.

Figure 35:
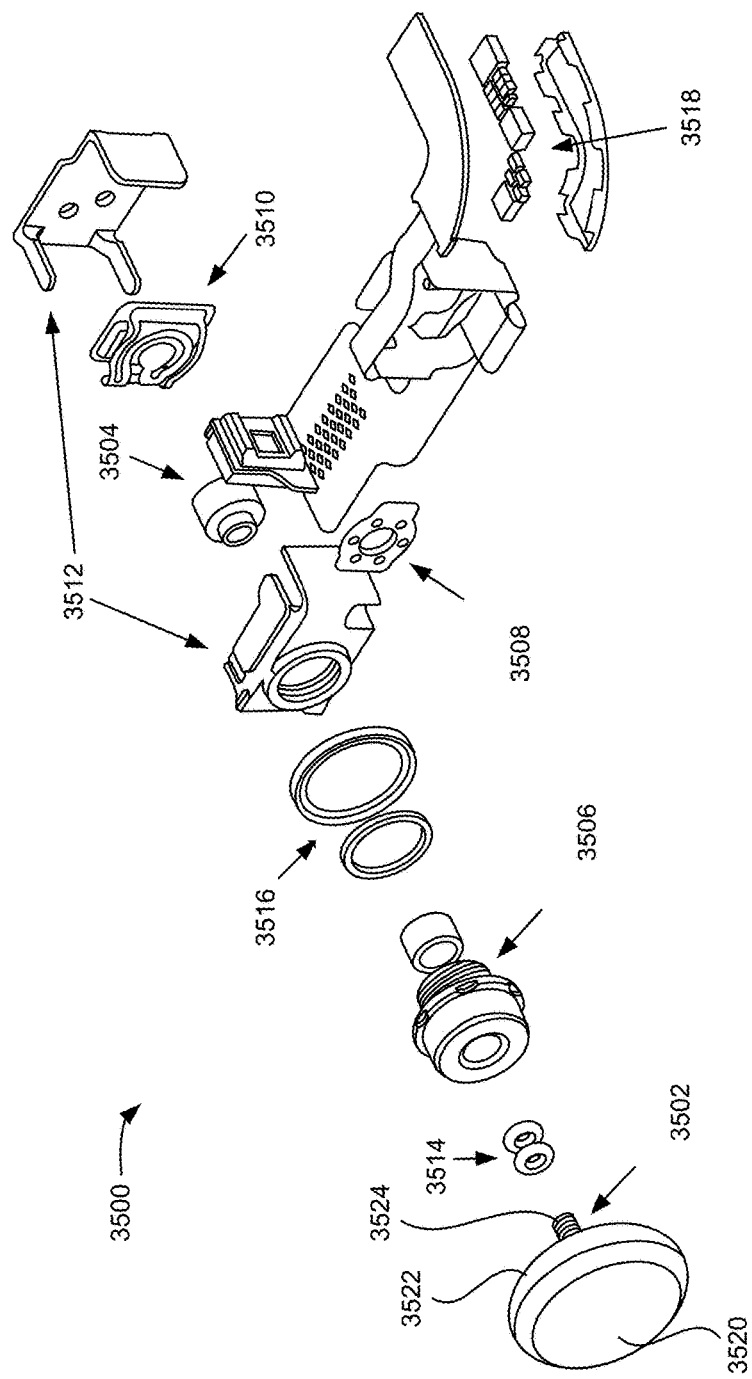
FIG. 35 is a simplified diagram illustrating an exploded view of an exemplary touch-sensitive dial, according to some embodiments of the present disclosure.

FIG. 35 is a simplified diagram illustrating an exploded view of an exemplary touch-sensitive dial 3500, according to some embodiments of the present disclosure. Dial 3500 can include a crown dial 3502 coupled to a threaded seat 3504. Crown dial 3502 can include a face contact 3520 and a periphery contact 3522 for receiving one or more inputs by contacting with external entities, such as a user's finger, and a threaded insert 3524. Threaded insert 3524 can be inserted through a crown collar 3506, an insert plate 3508, and an opening of a switch bracket 3512 to couple with threaded seat 3504. Switch bracket 3512 can house threaded seat 3504 and a shear plate 3510 against which threaded seat 3504 is attached. Shear plate 3510 can be coupled to capacitive touch components 3518, which can include a plurality of electrical routing components for routing electrical signals from dial 3500 to inner components of the portable electronic device. An example of an electrical pathway through dial 3500 is illustrated in FIG. 36.

Figure 36:
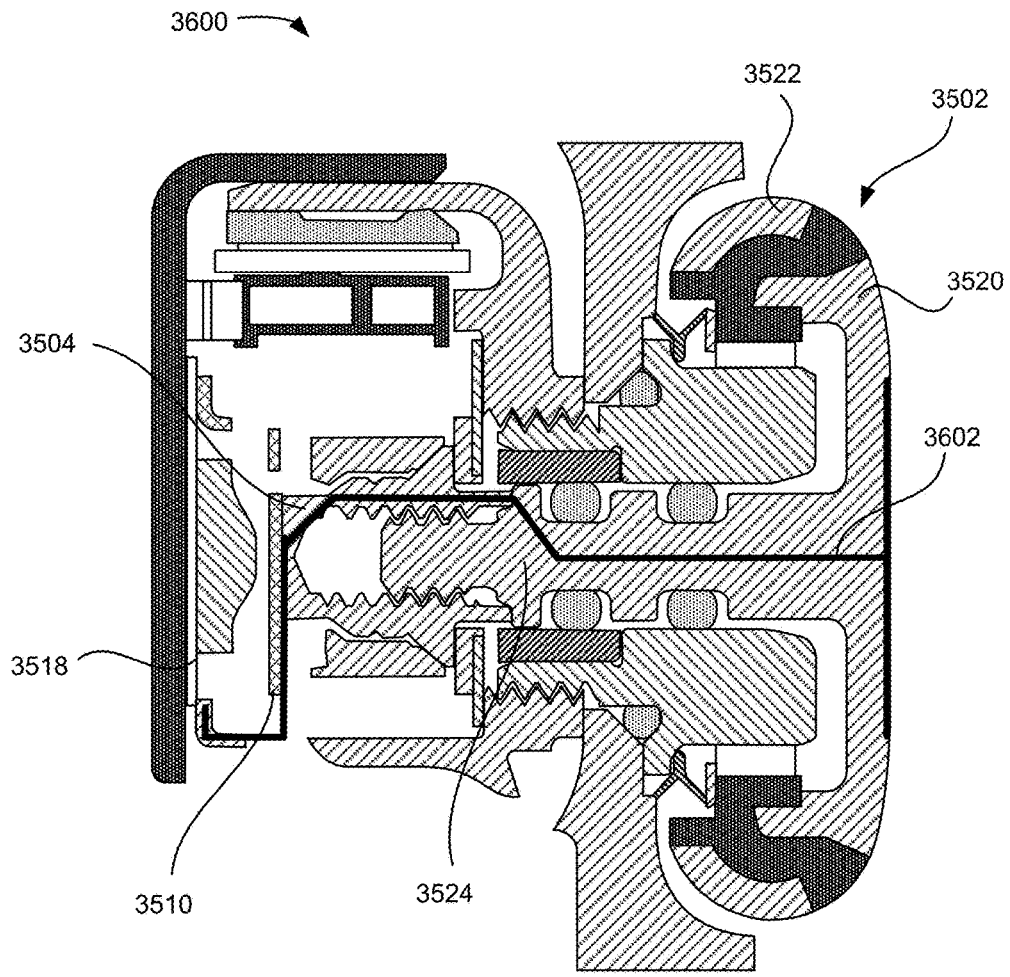
FIG. 36 is a cross-sectional illustration of an exemplary electrical pathway through a dial, according to some embodiments of the present disclosure.

FIG. 36 is a cross-sectional view illustration 3600 of dial 3500 to show an exemplary electrical pathway 3602 through dial 3500, according to some embodiments of the present disclosure. In some instances, electrical pathway 3602 can begin from face contact 3520 of crown dial 3502, such as when a user's finger touches face contact 3520. Electrical pathway 3602 can then continue through threaded insert 3524 and into threaded seat 3504. Once at threaded seat 3504, electrical pathway 3602 can continue through shear plate 3510 and end at capacitive touch components 3518. Thus, an electrical input signal can route through dial 3500 to enable the portable electronic device to perform one or more functions, such as EKG sensing.

Although the invention has been described with respect to specific embodiments, it will be appreciated that the invention is intended to cover all modifications and equivalents within the scope of the following claims.

What is claimed is:

1. A portable electronic device, comprising:
   a housing comprising a top portion including a display and a bottom portion including a window, the bottom portion is configured to mate with the top portion to form an internal cavity;
   an antenna disposed within the internal cavity and comprising an antenna element and a conductive antenna body coupled to a bottom surface of the antenna element, the antenna having an opening disposed at the center of the antenna and defined by an inner edge of the antenna;
   a wireless charging receiver system disposed within the internal cavity and the antenna opening, the wireless charging receiver system comprising a primary coil having an inner diameter and an outer diameter, a ferromagnetic shield covering a portion of at least two surfaces of the primary coil, and a secondary coil wound about overlapping portions of the primary coil and the ferromagnetic shield; and
   a sensor module disposed within the internal cavity and the inner diameter of the primary coil, the sensor module comprising at least one sensing device configured to measure a parameter of an environment external to the portable electronic device.

2. The portable electronic device of claim 1, wherein the primary coil is configured to receive time-varying magnetic flux propagating in a first direction and at a first frequency, and wherein the secondary coil is configured to receive time-varying magnetic flux propagating in a second direction different from the first direction and at a second frequency different from the first frequency.

3. The portable electronic device of claim 1, wherein the conductive antenna body is a layer of conductive material that conforms to the bottom surface of the antenna element and is configured to send and receive communication signals through radio waves.

4. The portable electronic device of claim 1, wherein the ferromagnetic shield extends from a first radial location to a second radial location different from the first radial location.

5. The portable electronic device of claim 1, wherein the inner edge of the antenna conforms to an outer profile of the wireless charging receiver system.

6. The portable electronic device of claim 1, wherein the sensor module is configured to measure the parameter of the environment through the window of the bottom portion of the housing.

7. The portable electronic device of claim 1, wherein the antenna comprises:
    a top level forming the outer edge of the antenna;
    a bottom level forming the antenna opening and the inner edge of the antenna; and
    a step region disposed between the top level and the bottom level.

8. The portable electronic device of claim 7, wherein the top level and the bottom level are each planar structures that are oriented along separate but parallel planes, and the step region is a vertical portion of the antenna that has a circular profile and couples the top level to the bottom level.

9. A portable electronic device, comprising:
    a housing comprising a top portion including a display and a bottom portion including a window, the bottom portion is configured to mate with the top portion to form an internal cavity, wherein the window includes a plurality of ink layers coated on portions of an inner surface and an outer surface of the window;
    a spacer disposed within the internal cavity and comprising a non-conductive material, the spacer having an opening disposed at the center of the spacer and defined by an inner edge of the spacer;
    a wireless charging receiver system disposed within the internal cavity and the opening, the wireless charging receiver system comprising a primary coil having an inner diameter and an outer diameter, a ferromagnetic shield covering a portion of at least two surfaces of the primary coil, and a secondary coil wound about overlapping portions of the primary coil and the ferromagnetic shield;
    a sensor module disposed within the internal cavity and the inner diameter of the primary coil, the sensor module comprising at least one sensing device configured to measure a parameter of an environment external to the portable electronic device;
    an alignment module coupled to the sensor module, the alignment module comprising an alignment magnet and a DC shield attached to a top surface of the alignment magnet; and
    an electromagnetic shield layer positioned between the wireless charging receiver system and the window of the bottom portion of the housing.

10. The portable electronic device of claim 9, wherein the at least one IR transparent layer and at least one IR opaque layer are coated on a portion of the inner surface of the window such that the center of the window is uncovered by the plurality of ink layers.

11. The portable electronic device of claim 9, wherein at least one conductive ink layer is coated on a portion of the outer surface of the window such that the center of the window is uncovered by the at least one conductive ink layer.

12. The portable electronic device of claim 9, further comprising a system-in-package disposed between the top portion of the housing and the spacer.

13. The portable electronic device of claim 9, wherein the spacer comprises:
    a top level forming the outer edge of the spacer;
    a bottom level forming the opening and the inner edge of the spacer; and
    a step region disposed between the top level and the bottom level.

14. The portable electronic device of claim 13, wherein the inner edge of the spacer and the step region both have circular profiles.

15. A wireless charging system, comprising:
    a first wireless charging transmitter comprising:
        a first housing having a first charging surface; and
        at least one first transmitter coil formed of a plurality of turns of stranded wire disposed within the first housing and below the first charging surface, the at least one first transmitter coil configured to generate first time-varying magnetic fields through and above the first charging surface; and
    a wireless charging receiver comprising:
        a housing comprising a top portion including a display and a bottom portion including a window, the bottom portion is configured to mate with the top portion to form an internal cavity;
        an antenna disposed within the internal cavity and comprising an antenna element and a conductive antenna body coupled to a bottom surface of the antenna element, the antenna having an opening disposed at the center of the antenna and defined by an inner edge of the antenna;
        a wireless charging receiver system disposed within the internal cavity and the antenna opening, the wireless charging receiver system comprising a primary receiver coil having an inner diameter and an outer diameter and configured to receive the first time-varying magnetic fields generated by the at least one first transmitter coil, a ferromagnetic shield covering a portion of at least two surfaces of the primary receiver coil, and a secondary receiver coil wound about overlapping portions of the primary receiver coil and the ferromagnetic shield; and
        a sensor module disposed within the internal cavity and the inner diameter of the primary receiver coil, the sensor module comprising at least one sensing device configured to measure a parameter of an environment external to the portable electronic device.

16. The wireless charging system of claim 15, wherein the at least one transmitter coil is configured to generate the time-varying magnetic fields in the first direction at the first frequency.

17. The wireless charging system of claim 15, further comprising a second wireless charging transmitter comprising:
    a second housing having a second charging surface; and
    at least one second transmitter coil formed of a plurality of turns of stranded wire disposed within the second housing and below the second charging surface, the at least one second transmitter coil configured to generate second time-varying magnetic fields through and above the second charging surface and in a second direction different from the first direction at a second frequency different from the first frequency.

18. The wireless charging system of claim 17, wherein the secondary receiver coil is configured to receive the second time-varying magnetic fields generated by the at least one second transmitter coil of the second wireless charging transmitter.

19. The wireless charging system of claim 15, wherein the antenna comprises:
   a top level forming the outer edge of the antenna;
   a bottom level forming the antenna opening and the inner edge of the antenna; and
   a step region disposed between the top level and the bottom level.

20. The wireless charging system of claim 15, wherein the conductive antenna body is a layer of conductive material that conforms to the bottom surface of the antenna element and is configured to send and receive communication signals through radio waves.

* * * * *